US008105550B2

(12) United States Patent
Quan et al.

(10) Patent No.: US 8,105,550 B2
(45) Date of Patent: Jan. 31, 2012

(54) METHOD AND SYSTEM FOR MICROFLUIDIC DEVICE AND IMAGING THEREOF

(75) Inventors: Emerson Chueng Quan, South San Francisco, CA (US); Colin Jon Taylor, Burlingame, CA (US); Michael Lee, Lake Oswego, OR (US); Christopher G. Cesar, Sunnyvale, CA (US); Greg Harris, Longmont, CO (US); Gang Sun, Cupertino, CA (US)

(73) Assignee: Fluidigm Corporation, South San Francisco, CA (US)

( * ) Notice: Subject to any disclaimer, the term of this patent is extended or adjusted under 35 U.S.C. 154(b) by 218 days.

(21) Appl. No.: 12/645,396

(22) Filed: Dec. 22, 2009

(65) Prior Publication Data
US 2010/0166608 A1 Jul. 1, 2010

Related U.S. Application Data

(62) Division of application No. 10/851,777, filed on May 20, 2004, now Pat. No. 7,695,683.

(60) Provisional application No. 60/490,666, filed on Jul. 28, 2003, provisional application No. 60/490,584, filed on Jul. 28, 2003, provisional application No. 60/472,226, filed on May 20, 2003.

(51) Int. Cl.
*G01N 33/00* (2006.01)
(52) U.S. Cl. .......... 422/500; 422/50; 422/68.1; 436/43; 436/63
(58) Field of Classification Search .......... 422/500, 422/50, 68.1; 436/43, 63
See application file for complete search history.

(56) References Cited

U.S. PATENT DOCUMENTS

| | | | |
|---|---|---|---|
| 3,570,515 | A | 3/1971 | Kinner |
| 3,747,628 | A | 7/1973 | Holster et al. |
| 4,046,159 | A | 9/1977 | Pegourie |
| 4,119,368 | A | 10/1978 | Yamazaki |
| 4,153,855 | A | 5/1979 | Feingold |
| 4,245,673 | A | 1/1981 | Bouteille et al. |
| 4,373,527 | A | 2/1983 | Fischell |

(Continued)

FOREIGN PATENT DOCUMENTS
EP 0 592 094 A2 4/1994
(Continued)

OTHER PUBLICATIONS

"Last Chance for Micromachines," The Economist Technology Quarterly, 8 pages, Dec. 7, 2000.

(Continued)

*Primary Examiner* — Sam P Siefke
(74) *Attorney, Agent, or Firm* — Kilpatrick Townsend & Stockton LLP

(57) ABSTRACT

A biological substrate, e.g., microfluidic chip. The substrate includes a rigid substrate material, which has a surface region capable of acting as a handle substrate. The substrate also has a deformable fluid layer coupled to the surface region. One or more well regions are formed in a first portion of the deformable fluid layer and are capable of holding a fluid therein. The one or more channel regions are formed in a second portion of the deformable fluid layer and are coupled to one or more of the well regions. An active region is formed in the deformable fluid layer. At least three fiducial markings are formed within the non-active region and disposed in a spatial manner associated with at least one of the well regions. A control layer is coupled to the fluid layer.

19 Claims, 28 Drawing Sheets

U.S. PATENT DOCUMENTS

| | | | |
|---|---|---|---|
| 4,434,704 | A | 3/1984 | Surjaatmadja |
| 4,575,681 | A | 3/1986 | Grosso et al. |
| 4,662,710 | A | 5/1987 | ten Berge |
| 4,797,842 | A | 1/1989 | Nackman et al. |
| 4,898,582 | A | 2/1990 | Faste |
| 4,992,312 | A | 2/1991 | Frisch |
| 5,085,562 | A | 2/1992 | Van Lintel |
| 5,088,515 | A | 2/1992 | Kamen |
| 5,096,388 | A | 3/1992 | Weinberg |
| 5,126,115 | A | 6/1992 | Fujita et al. |
| 5,164,558 | A | 11/1992 | Huff et al. |
| 5,171,132 | A | 12/1992 | Miyazaki |
| 5,224,843 | A | 7/1993 | Van Lintel |
| 5,259,737 | A | 11/1993 | Kamisuki et al. |
| 5,265,327 | A | 11/1993 | Faris et al. |
| 5,290,240 | A | 3/1994 | Horres, Jr. |
| 5,336,062 | A | 8/1994 | Richter |
| 5,346,372 | A | 9/1994 | Naruse et al. |
| 5,375,979 | A | 12/1994 | Trah |
| 5,376,252 | A | 12/1994 | Ekstrom |
| 5,400,741 | A | 3/1995 | DeTitta et al. |
| 5,423,287 | A | 6/1995 | Usami et al. |
| 5,500,071 | A | 3/1996 | Kaltenbach et al. |
| 5,529,465 | A | 6/1996 | Zengerle et al. |
| 5,571,410 | A | 11/1996 | Swedberg et al. |
| 5,574,893 | A | 11/1996 | Southgate et al. |
| 5,588,430 | A | 12/1996 | Bova et al. |
| 5,593,130 | A | 1/1997 | Hansson et al. |
| 5,642,015 | A | 6/1997 | Whitehead et al. |
| 5,659,171 | A | 8/1997 | Young et al. |
| 5,660,370 | A | 8/1997 | Webster |
| 5,665,070 | A | 9/1997 | McPhee |
| 5,681,024 | A | 10/1997 | Lisec et al. |
| 5,705,018 | A | 1/1998 | Hartley |
| 5,759,014 | A | 6/1998 | Van Lintel |
| 5,775,371 | A | 7/1998 | Pan et al. |
| 5,788,468 | A | 8/1998 | Dewa et al. |
| 5,836,750 | A | 11/1998 | Cabuz |
| 5,842,787 | A | 12/1998 | Kopf-Sill et al. |
| 5,854,684 | A | 12/1998 | Stabile et al. |
| 5,875,817 | A | 3/1999 | Carter |
| 5,876,187 | A | 3/1999 | Afromowitz |
| 5,885,470 | A | 3/1999 | Parce et al. |
| 5,932,799 | A | 8/1999 | Moles |
| 5,942,443 | A | 8/1999 | Parce et al. |
| 6,007,309 | A | 12/1999 | Hartley |
| 6,043,080 | A | 3/2000 | Lipshutz et al. |
| 6,048,498 | A | 4/2000 | Kennedy |
| 6,123,769 | A | 9/2000 | Sanjoh |
| 6,132,685 | A | 10/2000 | Kercso et al. |
| 6,155,282 | A | 12/2000 | Zachary et al. |
| 6,167,910 | B1 | 1/2001 | Chow |
| 6,174,365 | B1 | 1/2001 | Sanjoh |
| 6,246,330 | B1 | 6/2001 | Nielsen |
| 6,296,673 | B1 | 10/2001 | Santarsiero et al. |
| 6,321,791 | B1 | 11/2001 | Chow |
| 6,345,502 | B1 | 2/2002 | Tai et al. |
| 6,358,387 | B1 | 3/2002 | Kopf-Sill et al. |
| 6,375,871 | B1 | 4/2002 | Bentsen et al. |
| 6,376,971 | B1 | 4/2002 | Petrine et al. |
| 6,409,832 | B2 | 6/2002 | Weigl et al. |
| 6,508,988 | B1 | 1/2003 | Van Dam et al. |
| 6,520,936 | B1 | 2/2003 | Mann |
| 6,540,895 | B1 | 4/2003 | Spence et al. |
| 6,667,124 | B2 | 12/2003 | Suenaga et al. |
| 6,713,327 | B2 | 3/2004 | Leedy |
| 6,765,279 | B2 | 7/2004 | Leedy |
| 6,767,706 | B2 | 7/2004 | Quake et al. |
| 6,829,753 | B2 | 12/2004 | Lee et al. |
| 6,847,153 | B1 | 1/2005 | Balizer |
| 6,885,982 | B2 | 4/2005 | Harris et al. |
| 6,951,632 | B2 | 10/2005 | Unger et al. |
| 7,042,649 | B2 | 5/2006 | Quake et al. |
| 7,059,348 | B2 | 6/2006 | Nat |
| 7,062,418 | B2 | 6/2006 | Lee et al. |
| 7,097,809 | B2 | 8/2006 | Dam et al. |
| 7,161,736 | B2 | 1/2007 | Legrand et al. |
| 7,192,629 | B2 | 3/2007 | Lammertink et al. |
| 7,217,367 | B2 | 5/2007 | Huang et al. |
| 7,232,109 | B2 | 6/2007 | Driggs et al. |
| 7,248,413 | B2 | 7/2007 | Quake et al. |
| 7,262,923 | B2 | 8/2007 | Quake et al. |
| 7,279,146 | B2 | 10/2007 | Nassef |
| 7,291,512 | B2 | 11/2007 | Unger |
| 7,294,503 | B2 | 11/2007 | Quake et al. |
| 7,368,163 | B2 | 5/2008 | Huang et al. |
| 7,442,556 | B2 | 10/2008 | Manger et al. |
| 7,476,363 | B2 | 1/2009 | Unger et al. |
| 7,526,741 | B2 | 4/2009 | Lee et al. |
| 7,604,965 | B2 | 10/2009 | McBride et al. |
| 7,666,361 | B2 | 2/2010 | McBride et al. |
| 7,678,547 | B2 | 3/2010 | Eyal et al. |
| 7,691,333 | B2 | 4/2010 | McBride et al. |
| 7,749,737 | B2 | 7/2010 | McBride et al. |
| 7,792,345 | B2 | 9/2010 | Taylor et al. |
| 7,815,868 | B1 | 10/2010 | Jones et al. |
| 7,820,427 | B2 | 10/2010 | Unger et al. |
| 7,833,708 | B2 | 11/2010 | Enzelberger et al. |
| 7,837,946 | B2 | 11/2010 | McBride et al. |
| 2001/0027745 | A1 | 10/2001 | Weigl et al. |
| 2001/0041357 | A1 | 11/2001 | Fouillet et al. |
| 2002/0014673 | A1 | 2/2002 | Leedy |
| 2002/0037499 | A1 | 3/2002 | Quake et al. |
| 2002/0045297 | A1 | 4/2002 | Leedy |
| 2002/0108096 | A1 | 8/2002 | Lee et al. |
| 2003/0008308 | A1 | 1/2003 | Enzelberger et al. |
| 2003/0080442 | A1 | 5/2003 | Unger |
| 2003/0134129 | A1 | 7/2003 | Lammertink et al. |
| 2004/0072278 | A1 | 4/2004 | Chou et al. |
| 2004/0180377 | A1 | 9/2004 | Manger et al. |
| 2004/0248167 | A1 | 12/2004 | Quake et al. |
| 2005/0037471 | A1 | 2/2005 | Liu et al. |
| 2005/0053952 | A1 | 3/2005 | Hong et al. |
| 2005/0065735 | A1 | 3/2005 | Lee et al. |
| 2005/0084421 | A1 | 4/2005 | Unger et al. |
| 2005/0129581 | A1 | 6/2005 | McBride et al. |
| 2005/0197652 | A1 | 9/2005 | Nat |
| 2006/0172408 | A1 | 8/2006 | Quake et al. |
| 2006/0233674 | A1 | 10/2006 | Nelson |
| 2006/0281183 | A1 | 12/2006 | Sun et al. |
| 2007/0134807 | A1 | 6/2007 | Bao et al. |
| 2007/0224617 | A1 | 9/2007 | Quake et al. |
| 2007/0248971 | A1 | 10/2007 | Maerkl et al. |
| 2008/0050283 | A1 | 2/2008 | Chou et al. |
| 2008/0075380 | A1 | 3/2008 | Dube et al. |
| 2008/0108063 | A1 | 5/2008 | Lucero et al. |
| 2008/0129736 | A1 | 6/2008 | Sun et al. |
| 2008/0176211 | A1 | 7/2008 | Spence et al. |
| 2008/0223721 | A1 | 9/2008 | Cohen et al. |
| 2008/0230387 | A1 | 9/2008 | McBride et al. |
| 2008/0264863 | A1 | 10/2008 | Quake et al. |
| 2008/0274493 | A1 | 11/2008 | Quake et al. |
| 2008/0281090 | A1 | 11/2008 | Lee et al. |
| 2008/0292504 | A1 | 11/2008 | Goodsaid et al. |
| 2009/0018195 | A1 | 1/2009 | Balagadde |
| 2009/0069194 | A1 | 3/2009 | Ramakrishnan |
| 2009/0142236 | A1 | 6/2009 | Unger et al. |
| 2009/0147918 | A1 | 6/2009 | Fowler et al. |
| 2009/0168066 | A1 | 7/2009 | Hansen et al. |
| 2009/0239308 | A1 | 9/2009 | Dube et al. |
| 2009/0291435 | A1 | 11/2009 | Unger et al. |
| 2010/0104477 | A1 | 4/2010 | Liu et al. |
| 2010/0120018 | A1 | 5/2010 | Quake et al. |
| 2010/0120077 | A1 | 5/2010 | Daridon |
| 2010/0154890 | A1 | 6/2010 | Maerkl et al. |
| 2010/0166608 | A1 | 7/2010 | Quan et al. |
| 2010/0171954 | A1 | 7/2010 | Quake et al. |
| 2010/0183481 | A1 | 7/2010 | Facer et al. |
| 2010/0184202 | A1 | 7/2010 | McBride et al. |
| 2010/0187105 | A1 | 7/2010 | Unger et al. |
| 2010/0196892 | A1 | 8/2010 | Quake et al. |
| 2010/0197522 | A1 | 8/2010 | Liu et al. |
| 2010/0200782 | A1 | 8/2010 | Unger et al. |
| 2010/0230613 | A1 | 9/2010 | Pieprzyk et al. |
| 2010/0263732 | A1 | 10/2010 | Hansen et al. |

| | | | |
|---|---|---|---|
| 2010/0263757 | A1 | 10/2010 | Fernandes et al. |
| 2010/0311060 | A1 | 12/2010 | Facer et al. |
| 2010/0320364 | A1 | 12/2010 | Unger et al. |

FOREIGN PATENT DOCUMENTS

| | | |
|---|---|---|
| EP | 0 703 364 A1 | 3/1996 |
| EP | 0 706 004 A2 | 4/1996 |
| EP | 0 779 436 A2 | 6/1997 |
| EP | 0 829 360 A2 | 3/1998 |
| EP | 0 845 603 A1 | 6/1998 |
| EP | 0 999 055 A2 | 5/2000 |
| GB | 2 155 152 A | 9/1985 |
| GB | 2 308 460 A | 6/1997 |
| JP | 2000-508961 | 7/2000 |
| JP | 2002-526773 | 8/2002 |
| WO | WO 98/07069 A1 | 2/1998 |
| WO | WO 99/00655 A2 | 1/1999 |
| WO | WO 99/04361 A1 | 1/1999 |
| WO | WO 99/17093 A1 | 4/1999 |
| WO | WO 99/52633 A1 | 10/1999 |
| WO | WO 00/00678 A1 | 1/2000 |
| WO | WO 00/43748 A1 | 7/2000 |
| WO | WO 00/60345 A1 | 10/2000 |
| WO | WO 01/04613 A1 | 1/2001 |
| WO | WO 01/06529 A1 | 1/2001 |
| WO | WO 01/06575 A1 | 1/2001 |
| WO | WO 01/09595 A2 | 2/2001 |
| WO | WO 01/09595 A3 | 2/2001 |
| WO | WO 01/67369 A2 | 9/2001 |
| WO | WO 02/082047 A2 | 10/2002 |
| WO | WO 2007/033385 A2 | 3/2007 |
| WO | WO 2007/044091 A2 | 4/2007 |
| WO | WO 2008/043046 A2 | 4/2008 |
| WO | WO 2009/100449 A1 | 8/2009 |
| WO | WO 2010/011852 A1 | 1/2010 |
| WO | WO 2010/017210 A1 | 2/2010 |
| WO | WO 2010/077618 A1 | 7/2010 |

OTHER PUBLICATIONS

"The Liver Chip," Technology Review, pp. 64-67, Mar. 2003.
"Biochips," Nature Biotechnology, vol. 18, Supplement 2000, pp. IT43-IT44, 2000.
"Chapter 9: Microfluidic Devices," Micromachined Transducers Sourcebook, pp. 779-882, 1998.
Affholter, Joseph et al., "Engineering a Revolution," Chemistry in Britain, pp. 48-51, Apr. 1999.
Ahn, Chong H. et al., "Fluid Micropumps Based on Rotary Magnetic Actuators," Proceedings of 1995 IEEE Micro Electro Mechanical Systems Workshop (MEMS '95), Amsterdam, Netherlands, pp. 408-412, Jan. 29-Feb. 2, 1995.
Anderson, Janelle R. et al., "Fabrication of Topologically Complex Three-Dimensional Microfluidic Systems in PDMS by Rapid Prototyping," Analytical Chemistry, vol. 72, No. 14, pp. 3158-3164, Jul. 15, 2000.
Anderson, Rolfe C. et al., "Microfluidic Biochemical Analysis System," Transducers '97, 1997 International Conference on Solid-State Sensors and Actuators, Chicago, Illinois, pp. 477-480, Jun. 16-19, 1997.
Angell, James B. et al., "Silicon Micromechanical Devices," Scientific American, pp. cover, 44-55, Apr. 1983.
Armani, Deniz et al., "Re-Configurable Fluid Circuits by PDMS Elastomer Micromachining," IEEE Int. Conf. Micro Electro Mech. Syst. Tech. Digest, vol. 12, pp. 222-227, 1999.
Arnold, Frances H., "Design by Directed Evolution," Accounts of Chemical Research, vol. 31, No. 3, pp. 125-131, 1998.
Ashkin, A. et al., "Optical Trapping and Manipulation of Single Cells Using Infrared Laser Beams," Nature, vol. 330, No. 24, pp. 769-771, Dec. 31, 1987.
Ashkin, A. et al., "Optical Trapping and Manipulation of Viruses and Bacteria," Science, vol. 235, pp. 1517-1520, Mar. 20, 1987.
Ballantyne, J. P. et al., "Selective Area Metallization by Electron-Beam Controlled Direct Metallic Deposition," J. Vac. Sci. Technol., vol. 10, No. 6, pp. 1094-1097, Nov. 1973.
Belgrader, Phillip et al., "Rapid Pathogen Detection Using a Microchip PCR Array Instrument," Clinical Chemistry, vol. 44, No. 10, pp. 2191-2194, 1998.

Benard, W. L. et al., "A Titanium-Nickel Shape-Memory Alloy Actuated Micropump," Transducers '97, 1997 International Conference on Solid-State Sensors and Actuators, Chicago, Illinois, pp. 361-364, Jun. 16-19, 1997.
Black, Harvey, "Tiny Technology Promises Tremendous Profits," The Scientist, vol. 15, No. 21, 4 pages, Oct. 29, 2001.
Blanch, Harvey W. et al., Biochemical Engineering, pp. 2 cover pages and 305, 1996.
Blankenstein, Gert et al., "Modular Concept of a Laboratory on a Chip for Chemical and Biochemical Analysis," Biosensors & Bioelectronics, vol. 13, Nos. 3-4, pp. 427-438, 1998.
Bloomstein, T. M. et al., "Laser-Chemical Three-Dimensional Writing for Microelectromechanics and Application to Standard-Cell Microfluidics," J. Vac. Sci. Technol. B, vol. 10, No. 6, pp. 2671-2674, Nov. 1992.
Bousse, Luc et al., "Electrokinetically Controlled Microfluidic Analysis Systems," Annu. Rev. Biophys. Biomol. Struct., vol. 29, pp. 155-181, 2000.
Brechtel, R. et al., "Control of the Electroosmotic Flow by Metal-Salt-Containing Buffers," Journal of Chromatography A, vol. 716, pp. 97-105, 1995.
Brush, Michael, "Automated Laboratories," The Scientist, vol. 13, No. 4, 10 pages, Feb. 15, 1999.
Bryzek, Janusz et al., "Micromachines on The March", IEEE Spectrum, vol. 31, No. 5, pp. 20-31, May 1994.
Buchaillot, Lionel et al., "Silicon Nitride Thin Films Young's Modulus Determination by an Optical Non Destructive Method," Jpn. J. Appl. Phys., vol. 36, Part 2, No. 6B, pp. L794-L797, Jun. 15, 1997.
Buican, Tudor N. et al., "Automated Single-Cell Manipulation and Sorting by Light Trapping," Applied Optics, vol. 26, No. 24, pp. 5311-5316, Dec. 15, 1987.
Burbaum, Jonathan J. et al., "New Technologies for High-Throughput Screening," Current Opinion in Chemical Biology, vol. 1, pp. 72-78, 1997.
Calkins, Kathryn, "Mycometrix: Rubber Chips," BioCentury, 2 pages, Oct. 16, 2000.
Chan, Jason H. et al., "Microfabricated Polymer Devices for Automated Sample Delivery of Peptides for Analysis by Electrospray Ionization Tandem Mass Spectrometry," Analytical Chemistry, vol. 71, No. 20, pp. 4437-4444, Oct. 15, 1999.
Chang, Jun Keun et al., "Functional Integration of Serial Dilution and Capillary Electrophoresis on a PDMS Microchip," Biotechnology and Bioprocess Engineering, vol. 8, No. 4, pp. 233-239, 2003.
Chen, Chihchen et al., "Gray-Scale Photolithography Using Microfluidic Photomasks," PNAS, vol. 100, No. 4, pp. 1499-1504, Feb. 18, 2003.
Chiang, Yuh-Min et al., "Characterizing the Process of Cast Molding Microfluidic Systems," SPIE, vol. 3877, pp. 303-311, Sep. 1999.
Chiu, Daniel T. et al., "Patterned Deposition of Cells and Proteins Onto Surfaces by Using Three-Dimensional Microfluidic Systems," PNAS, vol. 97, No. 6, pp. 2408-2413, Mar. 14, 2000.
Chou, Hou-Pu et al., "A Microfabricated Device for Sizing and Sorting DNA Molecules," Proc. Natl. Acad. Sci., vol. 96, pp. 11-13, Jan. 1999.
Chou, Hou-Pu et al., "A Microfabricated Rotary Pump," Biomedical Microdevices, vol. 3, No. 4, pp. 323-330, 2001.
Chou, Hou-Pu et al., "Integrated Elastomer Fluidic Lab-on-a-Chip-Surface Patterning and DNA Diagnostics," Proceedings of the Solid State Actuator and Sensor Workshop, Hilton Head, South Carolina, 4 pages, 2000.
Chou, Hou-Pu et al., "Multiple Disease Diagnostics on a Single Chip," Biophysics Lab, Caltech, pp. 1-4, Mar. 1, 2000.
Cowen, S. et al., "An On-Chip Miniature Liquid Chromatography System: Design, Construction and Characterization," Micro Total Analysis Systems, Proceedings of the µTAS '94 Workshop, University of Twente, the Netherlands, pp. 2 cover pages and 295-298, 1995.
Delamarche, Emmanuel et al., "Patterned Delivery of Immunoglobulins to Surfaces Using Microfluidic Networks," Science, vol. 276, pp. 779-781, May 2, 1997.
Dharmatilleke, Saman et al., "Three-Dimensional Silicone Device Fabrication and Interconnection Scheme for Microfluidic Applications Using Sacrificial Wax Layers," Micro-Electro-Mechanical Systems (MEMS), vol. 2, pp. 413-418, 2000.

Duffy, David C. et al., "Patterning Electroluminescent Materials With Feature Sizes as Small as 5 μm Using Elastomeric Membranes as Masks for Dry Lift-Off," Advanced Materials, vol. 11, No. 7, pp. 546-552, 1999.

Duffy, David C. et al., "Rapid Prototyping of Microfluidic Switches in Poly(dimethyl siloxane) and Their Actuation by Electro-Osmotic Flow," J. Micromech. Microeng., vol. 9, pp. 211-217, 1999.

Duffy, David C. et al., "Rapid Prototyping of Microfluidic Systems in Poly(dimethylsiloxane)," Analytical Chemistry, vol. 70, No. 23, pp. 4974-4984, Dec. 1, 1998.

Effenhauser, Carlo S. et al., "Integrated Capillary Electrophoresis on Flexible Silicone Microdevices: Analysis of DNA Restriction Fragments and Detection of Single DNA Molecules on Microchips," Analytical Chemistry, vol. 69, No. 17, pp. 3451-3457, Sep. 1, 1997.

Effenhauser, Carlo S. et al., "Integrated Chip-Based Capillary Electrophoresis," Electrophoresis, vol. 18, pp. 2203-2213, 1997.

Effenhauser, Carlo S. et al., "Miniaturizing a Whole Analytical Laboratory Down to Chip Size," American Laboratory, vol. 26, No. 14, pp. cover, 15, 16, 18, 1994.

Effenhauser, Carlo S., "Integrated Chip-Based Microcolumn Separation Systems," Topics in Current Chemistry, vol. 194, pp. cover, 52-82, 1998.

Ericson, Christer et al., "Electroosmosis- and Pressure-Driven Chromatography in Chips Using Continuous Beds," Analytical Chemistry, vol. 72, No. 1, pp. 81-87, Jan. 1, 2000.

Eyal, Shulamit et al., "Velocity-Independent Microfluidic Flow Cytometry," Electrophoresis, vol. 23, pp. 2653-2657, 2002.

Fahrenberg, J. et al., "A Microvalve System Fabricated by Thermoplastic Molding," J. Micromech. Microeng., vol. 5, pp. 169-171, 1995.

Fettinger, J. C. et al., "Stacked Modules for Micro Flow Systems in Chemical Analysis: Concept and Studies Using an Enlarged Model," Sensors and Actuators B, vol. 17, pp. 19-25, 1993.

Figeys, Daniel et al., "An Integrated Microfluidics-Tandem Mass Spectrometry System for Automated Protein Analysis," Analytical Chemistry, vol. 70, No. 18, pp. 3728-3734, Sep. 15, 1998.

Figeys, Daniel et al., "Nanoflow Solvent Gradient Delivery From a Microfabricated Device for Protein Identifications by Electrospray Ionization Mass Spectrometry," Analytical Chemistry, vol. 70, No. 18, pp. 3721-3727, Sep. 15, 1998.

Fitzgerald, Deborah A., "Making Every Nanoliter Count," The Scientist, vol. 15, No. 21, 8 pages, Oct. 29, 2001.

Folch, A. et al., "Molding of Deep Polydimethylsiloxane Microstructures for Microfluidics and Biological Applications," Journal of Biomechanical Engineering, vol. 121, pp. 28-34, Feb. 1999.

Fu, Anne Y. et al., "A Microfabricated Fluorescence-Activated Cell-Sorter," Nature Biotechnology, vol. 17, pp. 1109-1111, Nov. 1999.

Galambos, Paul et al., "Electrical and Fluidic Packaging of Surface Micromachined Electro-Microfluidic Devices," 8 pages, no date.

Gao, Jun et al., "Integrated Microfluidic System Enabling Protein Digestion, Peptide Separation, and Protein Identification," Analytical Chemistry, vol. 73, No. 11, pp. 2648-2655, Jun. 1, 2001.

Garno, Jayne C. et al., "Production of Periodic Arrays of Protein Nanostructures Using Particle Lithography," Langmuir, vol. 18, No. 21, pp. 8186-8192, 2002.

Gass, V. et al., "Integrated Flow-Regulated Silicon Micropump," Sensors and Actuators A, vol. 43, pp. 335-338, 1994.

Gerlach, Torsten, "Pumping Gases by a Silicon Micro Pump With Dynamic Passive Valves," Transducers '97, 1997 International Conference on Solid-State Sensors and Actuators, Chicago, Illinois, pp. 357-360, Jun. 16-19, 1997.

Goll, C. et al., "Microvalves With Bistable Buckled Polymer Diaphragms," J. Micromech. Microeng., vol. 6, pp. 77-79, 1996.

Gravesen, Peter et al., "Microfluidics—A Review," J. Micromech. Microeng., vol. 3, pp. 168-192, 1993.

Greene, Ghana, "Characterizing the Properties of PDMS," pp. 1-11, Summer 2000.

Grover, William H. et al., "Monolithic Membrane Valves and Diaphragm Pumps for Practical Large-Scale Integration Into Glass Microfluidic Devices," Sensors and Actuators B, vol. 89, pp. 315-323, 2003.

Guérin, L. J. et al., "Simple and Low Cost Fabrication of Embedded Micro-Channels by Using a New Thick-Film Photoplastic," Transducers '97, 1997 International Conference on Solid-State Sensors and Actuators, Chicago, Illinois, pp. 1419-1422, Jun. 18-19, 1997.

Hanes, Jozef, et al., "In Vitro Selection and Evolution of Functional Proteins by Using Ribosome Display," Proc. Natl. Acad. Sci. USA, vol. 94, pp. 4937-4942, May 1997.

Hansen, Carl. L. et al., "A Robust and Scalable Microfluidic Metering Method That Allows Protein Crystal Growth by Free Interface Diffusion," PNAS, vol. 99, No. 26, pp. 16531-16536, Dec. 24, 2002.

Hansen, Carl. L. et al., "Systematic Investigation of Protein-Phase Behavior With a Microfluidic Formulator," PNAS Early Edition, 6 pages, 2004.

Harrison, D. Jed et al., "Micromachining a Miniaturized Capillary Electrophoresis-Based Chemical Analysis System on a Chip," Science, vol. 261, pp. 895-897, Aug. 13, 1993.

Henion, Jack et al., "Capillary Electrophoresis/Mass Spectrometry: From One Meter Capillaries to Chip-Based Devices," 2 pages, 1999.

Hicks, Jennifer, "Genetics and Drug Discovery Dominate Microarray Research," R&D Magazine, pp. 28-33, Feb. 1999.

Hoffmuller, Ulrich et al., "In Vitro Evolution and Selection of Proteins: Ribosome Display for Larger Libraries," Angew. Chem. Int. Ed., vol. 37, No. 23, pp. 3241-3243, 1998.

Hofmann, Oliver et al., "Modular Approach to Fabrication of Three-Dimensional Microchannel Systems in PDMS—Application to Sheath Flow Microchips," Lab on a Chip, vol. 1, pp. 108-114, 2001.

Hong, Jong Wook et al., "A Nanoliter-Scale Nucleic Acid Processor With Parallel Architecture," Nature Biotechnology, vol. 22, No. 4, pp. 1-5, Apr. 2004.

Hopfgartner, Gerard et al., "Exact Mass Measurement of Product Ions for the Structural Elucidation of Drug Metabolites With a Tandem Quadrupole Orthogonal-Acceleration Time-Of-Flight Mass Spectrometer," Journal of the American Society for Mass Spectrometry, vol. 10, pp. cover, 1305-1314, Dec. 1999.

Horn, Howard, "Lab Chips Sector: Microtechnologies are Changing Healthcare and More," Life Sciences, pp. 19-21, Mar. 20, 2001.

Hornbeck, Larry J. et al., "Bistable Deformable Mirror Device," Spatial Light Modulators and Applications 1988 Technical Digest Series, Summaries of papers presented at the Spatial Light Modulators and Applications Topical Meeting, Optical Society of America, vol. 8, Postconference Edition, A215, pp. 107-110, Jun. 15-17, 1988.

Hosokawa, Kazuo et al., "A Microfluidic Device for Mixing of Capillary-Drive Liquids," IEEJ Trans. SM, vol. 123, No. 1, pp. 23-24, 2003.

Hosokawa, Kazuo et al., "Droplet-Based Nano/Picoliter Mixer Using Hydrophobic Microcapillary Vent," 1999 IEEE International Conference on Micro Electro Mechanical Systems, Technical Digest, pp. 388-393, 1999.

Hosokawa, Kazuo et al., "Handling of Picoliter Liquid Samples in a Poly(dimethylsiloxane)-Based Microfluidic Device," Analytical Chemistry, vol. 71, No. 20, pp. 4781-4785, Oct. 15, 1999.

Ikuta, Koji et al., "Three Dimensional Micro Integrated Fluid Systems (MIFS) Fabricated by Stereo Lithography," IEEE, pp. 1-6, 1994.

Jacobson, Stephen C. et al., "High-Speed Separations on a Microchip," Analytical Chemistry, vol. 66, No. 7, pp. 1114-1118, Apr. 1, 1994.

Jacobson, Stephen C. et al., "Microfluidic Devices for Electrokinetically Driven Parallel and Serial Mixing," Analytical Chemistry, vol. 71, No. 20, pp. 4455-4459, Oct. 15, 1999.

Jerman, Hal, "Electrically-Activated, Normally-Closed Diaphragm Valves," Transducers '91, 1991 International Conference on Solid-State Sensors and Actuators, pp. cover, 1045-1048, 1991.

Jo, Byung-Ho et al., "Fabrication of Three-Dimensional Microfluidic Systems by Stacking Molded Polydimethylsiloxane (PDMS) Layers" SPIE, vol. 3877, pp. 222-229, Sep. 1999.

Jo, Byung-Ho et al., "Three-Dimensional Micro-Channel Fabrication in Polydimethylsiloxane (PDMS) Elastomer," Journal of Microelectromechanical Systems, vol. 9, No. 1, pp. 76-81, Mar. 2000.

Juárez-Martinez, G. et al., "High-Throughput Screens for Postgenomics: Studies of Protein Crystallization Using Microsystems Technology," Analytical Chemistry, vol. 74, No. 14, pp. 3505-3510, Jul. 15, 2002.

Jung, D. R. et al., "Chemical and Physical Interactions at Metal/Self-Assembled Organic Monolayer Interfaces," pp. 1-54, 1994.

Kagan, C. R., "Organic-Inorganic Hybrid Materials as Semiconducting Channels in Thin-Film Field-Effect Transistors," Science, vol. 286, pp. 945-947, Oct. 29, 1999.

Kamentsky, Louis A. et al., "Spectrophotometer: New Instrument for Ultrarapid Cell Analysis," Science, vol. 150, pp. 630-631, Oct. 29, 1965.

Kapur, Ravi et al., "Fabrication and Selective Surface Modification of 3-Dimensionally Textured Biomedical Polymers From Etched Silicon Substrates," Journal of Biomedical Materials Research, vol. 33, pp. 205-216, 1996.

Kawano, Yasushi et al., "Rapid Isolation and Identification of Staphylococcal Exoproteins by Reverse Phase Capillary High Performance Liquid Chromatography-Electrospray Ionization Mass Spectrometry," FEMS Microbiology Letters, vol. 189, pp. 103-108, 2000.

Kenis, Paul J. A. et al., "Microfabrication Inside Capillaries Using Multiphase Laminar Flow Patterning," Science, vol. 285, pp. 83-85, Jul. 2, 1999.

Khoo, Melvin et al., "A Novel Micromachined Magnetic Membrane Microfluid Pump," pp. 1-4, no date.

Kim, Enoch et al., "Micromolding in Capillaries: Applications in Materials Science," J. Am. Chem. Soc., vol. 118, No. 24, pp. 5722-5731, 1996.

Kim, Enoch et al., "Polymer Microstructures Formed by Moulding in Capillaries," Nature, vol. 376, pp. 581-584, Aug. 17, 1995.

Kirk-Othmer, "Concise Encyclopedia of Chemical Technology," John Wiley & Sons, 5 pages, no date.

Kopp, Martin U. et al., "Chemical Amplification: Continuous-Flow PCR on a Chip," Science, vol. 280, pp. 1046-1048, May 15, 1998.

Kuhn, Lawrence et al., "Silicon Charge Electrode Array for Ink Jet Printing," IEEE Transactions on Electron Devices, vol. ED-25, No. 10, pp. 1257-1260, Oct. 1978.

Kumar, Amit et al., "Features of Gold Having Micrometer to Centimeter Dimensions Can Be Formed Through a Combination of Stamping With an Elastomeric Stamp and an Alkanethiol 'Ink' Followed by Chemical Etching," Appl. Phys. Lett., vol. 63, No. 14, pp. 2002-2004, Oct. 4, 1993.

Kumar, Amit et al., "Patterning Self-Assembled Monolayers: Applications in Materials Science," Langmuir, vol. 10, pp. 1498-1511, 1994.

Lagally, E. T. et al., "Single-Molecule DNA Amplification and Analysis in an Integrated Microfluidic Device," Analytical Chemistry, vol. 73, No. 3, pp. 565-570, Feb. 1, 2001.

Lagally, Eric T. et al., "Fully Integrated PCR-Capillary Electrophoresis Microsystem for DNA Analysis," Lab on a Chip, vol. 1, pp. 102-107, 2001.

Lagally, Eric T. et al., "Monolithic Integrated Microfluidic DNA Amplification and Capillary Electrophoresis Analysis System," Sensors and Actuators B, vol. 63, pp. 138-146, 2000.

Lammerink, T. S. J. et al., "Modular Concept for Fluid Handling Systems," IEEE, pp. 389-394, 1996.

Lazar, Iulia M. et al., "Novel Microfabricated Device for Electrokinetically Induced Pressure Flow and Electrospray Ionization Mass Spectrometry," Journal of Chromatography A, vol. 892, pp. 195-201, 2000.

Li, Jianjun et al., "Integration of Microfabricated Devices to Capillary Electrophoresis-Electrospray Mass Spectrometry Using a Low Dead Volume Connection: Application to Rapid Analyses of Proteolytic Digests," Analytical Chemistry, vol. 71, No. 15, pp. 3036-3045, Aug. 1, 1999.

Li, Paul C. H. et al., "Transport, Manipulation, and Reaction of Biological Cells On-Chip Using Electrokinetic Effects," Analytical Chemistry, vol. 69, No. 8, pp. 1564-1568, Apr. 15, 1997.

Licklider, Larry et al., "A Micromachined Chip-Based Electrospray Source for Mass Spectrometry," Analytical Chemistry, vol. 72, No. 2, pp. 367-375, Jan. 15, 2000.

Lin, L. Y. et al., "Free-Space Micromachined Optical Switches for Optical Networking," IEEE Journal of Selected Topics in Quantum Electronics, vol. 5, No. 1, pp. 4-9, Jan. 1999.

Lin, Yuehe et al., "Laser Micromachined Isoelectric Focusing Device on Polymer Substrate for Electrospray Mass Spectrometry," SPIE, vol. 3877, pp. 28-35, Sep. 1999.

Liu, Hanghui et al., "Development of Multichannel Devices With an Array of Electrospray Tips for High-Throughput Mass Spectrometry," Analytical Chemistry, vol. 72, No. 14, pp. 3303-3310, Jul. 15, 2000.

Liu, Jian et al., "A Nanoliter Rotary Device for Polymerase Chain Reaction," Electrophoresis, vol. 23, pp. 1531-1536, 2002.

Lötters, J C et al., "The Mechanical Properties of the Rubber Elastic Polymer Polydimethylsiloxane for Sensor Applications," J. Micromech. Microeng., vol. 7, pp. 145-147, 1997.

Lucy, Charles A. et al., "Characterization of the Cationic Surfactant Induced Reversal of Electroosmotic Flow in Capillary Electrophoresis," Anal. Chem., vol. 68, pp. 300-305, 1996.

Maluf, N., "An Introduction to Microelectromechanical Systems Engineering," Artech House Publishers, Boston London, pp. 42-45, Dec. 1999.

Manz, A. et al., "Micromachining of Monocrystalline Silicon and Glass for Chemical Analysis Systems," Trends in Analytical Chemistry, vol. 10, No. 5, pp. 144-149, 1991.

Marshall, Sid, "Fundamental Changes Ahead for Lab Instrumentation," R&D Magazine, 5 pages, Feb. 1999.

Marsili, Ray, "Lab-On-A-Chip Poised to Revolutionize Sample Prep," R&D Magazine, 5 pages, Feb. 1999.

McDonald, J. Cooper et al., "Fabrication of Microfluidic Systems in Poly(dimethylsiloxane)," Electrophoresis, vol. 21, pp. 27-40, 2000.

McDonald, J. Cooper et al., "Poly(dimethylsiloxane) as a Material for Fabricating Microfluidic Devices," Accounts of Chemical Research, vol. 35, No. 7, pp. 491-499, 2002.

Muller, Richard S. et al., "Surface-Micromachined Microoptical Elements and Systems," Proceedings of the IEEE, vol. 86, No. 8, pp. 1705-1720, Aug. 1998.

New Objective, Inc., "What is Electrospray," www.newobjective.com/electrospray/electrospray.html, 4 pages, 1999.

Ng, Jessamine M. K. et al., "Components for Integrated Poly(Dimethylsiloxane) Microfluidic Systems," Electrophoresis, vol. 23, pp. 3461-3473, 2002.

Oleschuk, Richard D. et al., "Analytical Microdevices for Mass Spectrometry," Trends in Analytical Chemistry, vol. 19, No. 6., pp. 379-388, 2000.

Olsson, Anders et al., "Simulation Studies of Diffuser and Nozzle Elements for Valve-Less Micropumps," Transducers '97, 1997 International Conference on Solid-State Sensors and Actuators, Chicago, Illinois, pp. 1039-1042, Jun. 16-19, 1997.

Pethig, Ronald et al., "Applications of Dielectrophoresis in Biotechnology," Tibtech, vol. 15, pp. 426-432, Oct. 1997.

Protana website, "NanoES Products," www.protana.com/products/default.asp, 3 pages, Sep. 19, 2000.

Qin, Dong et al., "Photolithography With Transparent Reflective Photomasks," J. Vac. Sci. Technol. B, vol. 16, No. 1, pp. 98-103, Jan. 1998.

Qin, Dong et al., "Elastomeric Light Valves," Adv. Mater., vol. 9, No. 5, pp. 407-410, 1997.

Quake, Stephen R. et al., "From Micro- to Nanofabrication With Soft Materials," Science, vol. 290, pp. 1536-1540, Nov. 24, 2000.

Rapp, R. et al., "LIGA Micropump for Gases and Liquids," Sensors and Actuators A, vol. 40, pp. 57-61, Jan. 1994.

Roberts, Richard W. et al., "RNA-Peptide Fusions for the In Vitro Selection of Peptides and Proteins," Proc. Natl. Acad. Sci. USA, vol. 94, pp. 12297-12302, Nov. 1997.

Roylance, Lynn Michelle et al., "A Batch-Fabricated Silicon Accelerometer," IEEE Transactions on Electron Devices, vol. ED-26, No. 12, pp. 1911-1917, Dec. 1979.

Sandia National Laboratories, "Electro Microfluidic Dual In-Line Package (EMDIP)," 2 pages, no date.

Sanjoh, Akira et al., "Spatiotemporal Protein Crystal Growth Studies Using Microfluidic Silicon Devices," Journal of Crystal Growth, vol. 196, pp. 691-702, 1999.

Sasserath, J. et al., "Rapid Prototyping and Development of Microfluidic and BioMEMS Devices," IVD Technology, 12 pages, Jun. 2002.

Schasfoort, Richard B. M. et al., "Field-Effect Flow Control for Microfabricated Fluidic Networks," Science, vol. 286, pp. 942-945, Oct. 29, 1999.

Schomburg, W. K. et al., "Fabrication of Polymer Microcomponents With the AMANDA-Process," New Materials and Directions, Eurosensors XII, pp. 711-714, Sep. 13-16, 1998.

Schueller, Olivier J. A. et al., "Fabrication of Glassy Carbon Microstructures by Soft Lithography," Sensors and Actuators A, vol. 72, pp. 126-139, 1999.

Shevchenko, Andrej et al., "Rapid 'de Novo' Peptide Sequencing by a Combination of Nanoelectrospray, Isotopic Labeling and a Quadrupole/Time-of-Flight Mass Spectometer," Rapid Communications in Mass Spectrometry, vol. 11, pp. 1015-1024, 1997.

Shinohara, Jun et al., "A High Pressure-Resistance Micropump Using Active and Normally-Closed Valves," IEEE, pp. 86-91, 2000.

Shoji, Shuichi et al., "Smallest Dead Volume Microvalves for Integrated Chemical Analyzing Systems," Transducers '91, 1991 International Conference on Solid-State Sensors and Actuators, San Francisco, California, pp. cover, 1052-1055, 1991.

Shoji, Shuichi, "Fluids for Sensor Systems," Topics in Current Chemistry, vol. 194, pp. 163-188, 1998.

Sklar, Larry A. et al., Sample Handling for Kinetics and Molecular Assembly in Flow Cytometry, SPIE, vol. 3256, pp. 144-153, 1998.

Smits, J.G., "Piezoelectric Micropump With Three Valves Working Peristaltically," Sensors and Actuators, vol. A21-A23, pp. 203-206, 1990.

Sohn, L. L. et al., "Capacitance Cytometry: Measuring Biological Cells One by One," PNAS, vol. 97, No. 20, pp. 10687-10690, Sep. 26, 2000.

Tawfik, Dan S. et al., "Man-Made Cell-Like Compartments for Molecular Evolution," Nature Biotechnology, vol. 16, pp. 652-656, Jul. 1998.

Taylor, Anne M. et al., "Microfluidic Multicompartment Device for Neuroscience Research," Langmuir, vol. 19, pp. 1551-1556, 2003.

Thompson, L. F. et al., "Introduction to Microlithography," 185th Meeting of the American Chemical Society, Seattle, WA, pp. 2 cover pages, 1-13, Mar. 20-25, 1983.

Thorsen, Todd et al., "Dynamic Pattern Formation in a Vesicle-Generating Microfluidic Device," Physical Review Letters, vol. 86, No. 18, pp. 4163-4166, Apr. 30, 2001.

Thorsen, Todd et al., "Microfluidic Large-Scale Integration," Science, vol. 298, No. 5593, pp. 580-584, Oct. 18, 2002.

Tufte, O. N. et al., "Silicon Diffused-Element Piezoresistive Diaphragms," Journal of Applied Physics, vol. 33, No. 11, pp. 3322-3327, Nov. 1962.

Ullmann's Encyclopedia of Industrial Chemistry, Sections 6 to 6.3, Topic: Carbon Black, Sixth Edition, 7 pages, 1999.

Unger, Marc A. et al., "Monolithic Microfabricated Valves and Pumps by Multilayer Soft Lithography," Science, vol. 288, pp. 113-116, Apr. 7, 2000.

Van De Pol, F.C.M. et al., "A Thermo-Pneumatic Actuation Principle for a Microminiature Pump and Other Micromechanical Devices," Sensors and Actuators, vol. 17, Nos. 1-2, pp. 139-143, May 3, 1989.

Van De Pol, F.C.M. et al., "Micro Liquid Handling Devices—A Review," Micro Systems Technologies, vol. 90, pp. 799-805, 1990.

Van Den Berg, A. et al., "Micro Total Analysis Systems," Proceedings of the µTAS '94 Workshop, University of Twente, The Netherlands, 17 pages, Nov. 21-22, 1994.

Van Der Woerd, Mark et al., "Lab-on-a-Chip Based Protein Crystallization," National Aeronautics and Space Administration and Caliper, pp. 1-27, Oct. 25, 2001.

Van Der Woerd, Mark et al., "The Promise of Macromolecular Crystallization in Microfluidic Chips," Journal of Structural Biology, vol. 142, pp. 180-187, 2003.

Velev, Orlin D., "On-Chip Manipulation of Free Droplets," Nature, vol. 426, pp. 515-516, Dec. 4, 2003.

Verpoorte, Elisabeth M. J. et al., "Three-Dimensional Micro Flow Manifolds for Miniaturized Chemical Analysis Systems," J. Micromech. Microeng., vol. 7, pp. 246-256, 1994.

Vieider, Christian et al., "A Pneumatically Actuated Micro Valve With a Silicon Rubber Membrane for Integration With Fluid Handling Systems," Transducers '95, 8th International Conference on Solid-State Sensors and Actuators and Eurosensors IX, Stockholm, Sweden, pp. 284-286, Jun. 25-29, 1995.

Vogelstein, Bert et al., "Digital PCR," Proc. Natl. Acad. Sci. USA, vol. 96, pp. 9236-9241, Aug. 1999.

Ward et al., Automatic Preparation of Protein Crystals Using Laboratory Robotics and Automated Visual Inspection, Journal of Crystal Growth 90 (1988), pp. 325-339.

Washizu, Masao et al., "Molecular Dielectrophoresis of Biopolymers," IEEE Transactions on Industry Applications, vol. 30, No. 4, pp. 835-843, Jul. 1994.

Weigl, Bernhard H., "Microfluidics-Based Lab-on-a-Chip Systems," IVD Technology Magazine, 8 pages, Nov./Dec. 2000.

Whelen, A. Christian et al., "The Role of Nucleic Acid Amplification and Detection in the Clinical Microbiology Laboratory," Annu. Rev. Microbiol., vol. 50, pp. 349-373, 1996.

Whitesides, George M. et al., "Flexible Methods for Microfluidics," Physics Today, pp. 42-48, Jun. 2001.

Whitesides, George M. et al., "Soft Lithography in Biology and Biochemistry," Annu. Rev. Biomed. Eng., vol. 3, pp. 335-373, 2001.

Wilbur, James L. et al., "Lithographic Molding: A Convenient Route to Structures With Sub-Micrometer Dimensions," Adv. Mater., vol. 7, No. 7, pp. 649-652, 1995.

Wilm, Matthias et al., "Femtomole Sequencing of Proteins From Polyacrylamide Gels by Nano-Electrospray Mass Spectrometry," Nature, vol. 379, pp. 466-469, Feb. 1, 1996.

Wu, Hongkai et al., "Fabrication of Complex Three-Dimensional Microchannel Systems in PDMS," J. Am. Chem. Soc., vol. 125, No. 2, pp. 554-559, 2003.

Xia, Younan et al., "Micromolding of Polymers in Capillaries: Applications in Microfabrication," Chem. Mater., vol. 8, No. 7, pp. 1559-1566, 1996.

Xia, Younan et al., "Complex Optical Surfaces Formed by Replica Molding Against Elastomeric Masters," Science, vol. 273, pp. 347-349, Jul. 19, 1996.

Xia, Younan et al., "Reduction in the Size of Features of Patterned SAMs Generated by Microcontact Printing With Mechanical Compression of the Stamp," Adv. Mater., vol. 7, No. 5, pp. 471-473, 1995.

Xia, Younan et al., "Soft Lithography," Angew. Chem. Int. Ed., vol. 37, pp. 551-575, 1998.

Xu, Bing et al., "Making Negative Poisson's Ratio Microstructures by Soft Lithography," Adv. Mater., vol. 11, No. 14, pp. 1186-1189, 1999.

Xu, Jingdong et al., "Room-Temperature Imprinting Method for Plastic Microchannel Fabrication," Analytical Chemistry, vol. 72, No. 8, pp. 1930-1933, Apr. 15, 2000.

Xue, Qifeng et al., "Integrated Multichannel Microchip Electrospray Ionization Mass Spectrometry: Analysis of Peptides From On-Chip Tryptic Digestion of Melittin," Rapid Communications in Mass Spectrometry, vol. 11, 1253-1256, 1997.

Xue, Qifeng et al., "Multichannel Microchip Electrospray Mass Spectrometry," Analytical Chemistry, vol. 69, No. 3, pp. 426-430, Feb. 1, 1997.

Yang, Xing et al., "A Low Power MEMS Silicone/Parylene Valve," Solid-State Sensor and Actuator Workshop, Hilton Head Island, South Carolina, 4 pages, Jun. 7-11, 1998.

Yang, Xing et al., "A MEMS Thermopneumatic Silicone Membrane Valve," IEEE 10th Annual International Workshop of Micro Electro Mechanical Systems, Nagoya, Japan, pp. cover, 114-118, Jan. 26-30, 1997.

Yazdi, Navid et al., "Micromachined Inertial Sensors," Proceedings of IEEE, vol. 86, No. 8, pp. 1640-1659, Aug. 1998.

Young, A. M. et al., "Contoured Elastic-Membrane Microvalves for Microfluidic Network Integration," Journal of Biomechanical Engineering, vol. 121, pp. 2-6, Feb. 1999.

Zdeblick, Mark J. et al., "A Microminiature Electric-To-Fluidic Valve," Transducers '87, Proceedings of the 4th International Conference on Solid-State Sensors and Actuators, reprinted in Micromechanics and MEMS Classic and Seminal Papers to 1990, pp. 2 cover pages, 437-439, Jun. 1987.

Zengerle, R. et al., "A Micro Membrane Pump With Electrostatic Actuation," Micro Electro Mechanical Systems '92, Travemünde, Germany, pp. 19-24, Feb. 4-7, 1992.

Zengerle, R. et al., "Performance Simulation of Microminiaturized Membrane Pumps," 7th International Conference on Solid-State Sensors and Actuators, Yokohama, Japan, pp. 2 cover pages, 106-109, Jun. 7-10, 1993.

Zhang, B. et al., "Microfabricated Devices for Capillary Electrophoresis-Electrospray Mass Spectrometry," Analytical Chemistry, vol. 71, No. 15, pp. 3258-3264, Aug. 1, 1999.

Zhao, Zhan, et al., "An Integrated Biochip Design and Fabrication," Proceedings of SPIE, vol. 4936, pp. 321-326, 2002.

Zheng, Bo et al., "A Droplet-Based, Composite PDMS/Glass Capillary Microfluidic System for Evaluating Protein Crystallization Conditions by Microbatch and Vapor-Diffusion Methods With On-Chip X-Ray Diffraction," Angew. Chem., pp. 1-4, 2004.

U.S. Appl. No. 10/851,777, Non-Final Office Action mailed May 2, 2007, 6 pages.

U.S. Appl. No. 10/851,777, Non-Final Office Action mailed Mar. 27, 2008, 5 pages.

U.S. Appl. No. 10/851,777, Final Office Actiom mailed Oct. 20, 2008, 5 pages.

U.S. Appl. No. 10/851,777, Non-Final Office Action mailed Feb. 3, 2009, 6 pages.

U.S. Appl. No. 10/851,777, Notice of Allowance mailed Sep. 23, 2009, 6 pages.

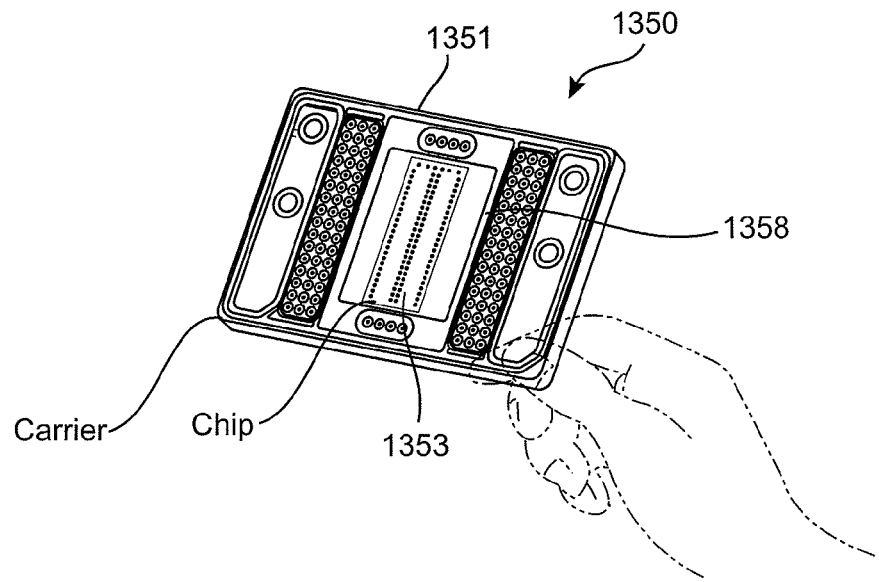
FIG. 13A
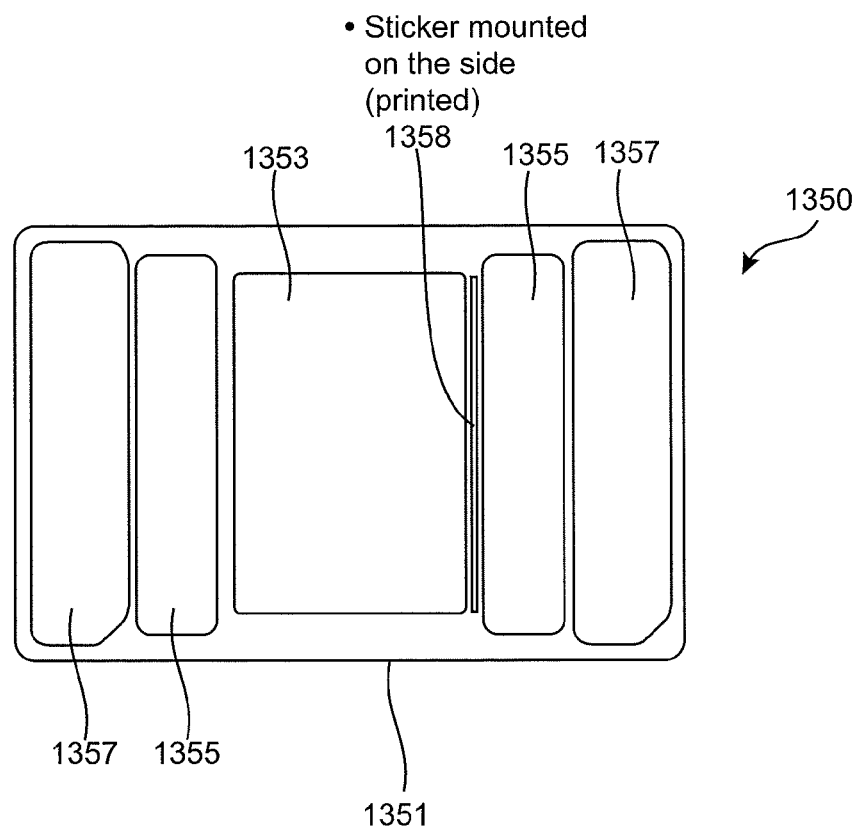

METHOD AND SYSTEM FOR MICROFLUIDIC DEVICE AND IMAGING THEREOF

CROSS-REFERENCES TO RELATED APPLICATIONS

This application is a divisional of U.S. application Ser. No. 10/851,777 filed May 20, 2004, which claims priority to U.S. Provisional Patent Application Nos. 60/472,226 filed May 20, 2003, 60/490,666 filed Jul. 28, 2003, and 60/490,584 filed Jul. 28, 2003, all of which are incorporated by reference herein for all purposes.

BACKGROUND OF THE INVENTION

According to the present invention, techniques for microfluidic systems, including a microfluidic chip or circuit, are provided. More particularly, the invention provides a microfluidic structure and method of manufacture, and a system and method for imaging a microfluidic device. Merely by way of example, the fiducial markings are used for processing and imaging a microfluidic chip, but it would be recognized that the invention has a much broader range of applicability.

Microfluidic techniques have progressed overtime. Certain techniques of producing microelectromechanical (MEMS) structures have been proposed. Such MEMS structures include pumps and valves. The pumps and valves are often silicon-based and are made from bulk micro-machining (which is a subtractive fabrication method whereby single crystal silicon is lithographically patterned and then etched to form three-dimensional structures). The pumps and valves also use surface micro-machining (which is an additive method where layers of semiconductor-type materials such as polysilicon, silicon nitride, silicon dioxide, and various metals are sequentially added and patterned to make three-dimensional structures). Unfortunately, certain limitations exist with these conventional MEMS structures and techniques for making them.

As merely an example, a limitation of silicon-based micro-machining is that the stiffness of the semiconductor materials used necessitates high actuation forces, which result in large and complex designs. In fact, both bulk and surface micro-machining methods are often limited by the stiffness of the materials used. Additionally, adhesion between various layers of the fabricated device is also a problem. For example, in bulk micro-machining, wafer bonding techniques must be employed to create multilayer structures. On the other hand, when surface micro-machining, thermal stresses between the various layers of the device limits the total device thickness, often to approximately 20 microns. Using either of the above methods, clean room fabrication and careful quality control are required.

Accordingly, techniques for manufacturing microfluidic systems using an elastomeric structure have been proposed. As merely an example, these structures are often made by forming an elastomeric layer on top of a micromachined mold. The micromachined mold has a raised protrusion which forms a recess extending along a bottom surface of the elastomeric layer. The elastomeric layer is bonded to other elastomeric layers to form fluid and control regions. The elastomeric layer has overcome certain limitations of conventional MEMS based structures. Further details of other characteristics of these elastomeric layers for microfluidic applications such as crystallization have been provided below.

Crystallization is an important technique to the biological and chemical arts. Specifically, a high-quality crystal of a target compound can be analyzed by x-ray diffraction techniques to produce an accurate three-dimensional structure of the target. This three-dimensional structure information can then be utilized to predict functionality and behavior of the target.

In theory, the crystallization process is simple. A target compound in pure form is dissolved in solvent. The chemical environment of the dissolved target material is then altered such that the target is less soluble and reverts to the solid phase in crystalline form. This change in chemical environment is typically accomplished by introducing a crystallizing agent that makes the target material less soluble, although changes in temperature and pressure can also influence solubility of the target material.

In practice however, forming a high quality crystal is generally difficult, often requiring much trial and error and patience on the part of the researcher. Specifically, the highly complex structure of even simple biological compounds means that they are usually not amenable to forming a highly ordered crystalline structure. Therefore, a researcher needs to be patient and methodical, experimenting with a large number of conditions for crystallization, altering parameters such as sample concentration, solvent type, countersolvent type, temperature, and duration in order to obtain a high quality crystal.

A high-throughput system for screening conditions for crystallization of target materials, for example proteins, is provided in a microfluidic device. The array of metering cells is formed by a multilayer elastomeric manufacturing process. Each metering cell comprises one or more of pairs of opposing chambers, each chamber being in fluid communication with the other through an interconnecting microfluidic channel, one chamber containing a protein solution, and the other, opposing chamber, containing a crystallization reagent. Along the channel, a valve is situated to keep the contents of opposing chambers from each other until the valve is opened, thus allowing free interface diffusion to occur between the opposing chambers through the interconnecting microfluidic channel. As the opposing chambers approach equilibrium with respect to crystallization reagent and protein concentrations as free interface diffusion progresses, the protein would at some point, form a crystal under certain conditions. In some embodiments, the microfluidic devices taught by Hansen et al. are have arrays of metering cells containing chambers for conducting protein crystallization experiments therein. Use of such arrays in turn provides for high-throughput testing of numerous conditions for protein crystallization which require analysis. See PCT publication WO 02/082047, published Oct. 17, 2002 and by Hansen, et al. PCT publication WO 02/082047 is incorporated by reference herein in its entirety for all purposes.

From the above, it is seen that improved techniques for elastomeric design and analysis are highly desirable.

BRIEF SUMMARY OF THE INVENTION

According to the present invention, techniques for microfluidic systems, including a microfluidic chip or circuit, are provided. More particularly, the invention provides a microfluidic structure and method of manufacture, and a system and method for imaging a microfluidic device. Merely by way of example, the fiducial markings are used for processing and imaging a microfluidic chip, but it would be recognized that the invention has a much broader range of applicability.

In a specific embodiment, the invention provides a biological substrate, e.g., microfluidic chip. The substrate includes a rigid substrate material, which has a surface region capable of acting as a handle substrate. The substrate also has a deformable fluid layer (e.g., polymeric material, silicone, silicone rubber, rubber, plastic, PDMS) coupled to the surface region. One or more well regions are formed in a first portion of the deformable fluid layer and are capable of holding a fluid therein. The one or more channel regions are formed in a second portion of the deformable fluid layer and are coupled to one or more of the well regions. An active region is formed in the deformable fluid layer. Such active region includes the one or more well regions, which are designed to hold fluid. A non-active region is formed in the deformable fluid layer. The non-active region is formed outside of the first portion and the second portion. Preferably, at least three fiducial markings are formed within the non-active region and disposed in a spatial manner associated with at least one of the well regions. A control layer is coupled to the fluid layer. Preferably, the substrate also includes an other fiducial marking with pre-designed shape and size, including at least an edge and center region.

In an alternative specific embodiment, the invention provides a method of fabricating a biological substrate. The method includes providing a rigid substrate material, which has a surface region and is capable of acting as a handle substrate. The method includes coupling a deformable fluid layer to the surface region of the rigid substrate. The deformable layer has one or more well regions formed in a first portion of the deformable fluid layer and one or more channel regions formed in a second portion of the deformable fluid layer. An active region is formed in the deformable fluid layer. A non-active region is formed in the deformable fluid layer and is formed outside of the first portion and the second portion. Preferably, at least three fiducial markings are formed within the non-active region and are disposed in a spatial manner associated with at least one of the well regions. The method also includes coupling a control layer to the fluid layer.

In yet an alternative embodiment, the invention provides a method of manufacturing microfluidic chip structures. The method includes providing a mold substrate including a plurality of well patterns. Each of the well patterns is provided within a portion of an active region of a fluidic chip. The method includes forming a plurality of fiducial marking patterns around a vicinity of each of the well patterns. Each of the plurality of fiducial marking patterns is within a portion of a non-active region of a fluidic chip. The plurality of fiducial marking patterns includes a set of alignment marks disposed spatially around each of the well patterns. The method also includes forming a thickness of deformable material within the plurality of well patterns and within the plurality of fiducial marking patterns to fill a portion of the mold substrate. The method includes coupling the thickness of deformable material including a plurality of wells formed from the well patterns and a plurality of fiducial marking patterns formed from the fiducial marking patterns to rigid substrate material.

In yet an alternatively embodiment, the present invention provides a microfluidic system. The system has a rigid substrate material, which includes a surface region that is capable of acting as a handle substrate. The system has a deformable fluid layer coupled to the surface region. One or more well regions is formed in a first portion of the deformable fluid layer. The one or more well regions is capable of holding a fluid therein. The system has one or more channel regions formed in a second portion of the deformable fluid layer. The one or more channel regions is coupled to one or more of the well regions. An active region is formed in the deformable fluid layer. The active region includes the one or more well regions. A non-active region is formed in the deformable fluid layer. The non-active region is formed outside of the first portion and the second portion. A first fiducial marking is formed within the non-active region and is disposed in a spatial manner associated with at least one of the channel regions. A second fiducial marking is formed within the non-active region and is disposed in a spatial manner associated with at least one of the well regions. A control layer is coupled to the fluid layer. The control layer includes one or more control regions. A third fiducial marking is formed within the control layer.

In yet an alternative specific embodiment, the present invention provides another microfluidic system. The system has a substrate comprising a surface region. A deformable layer is coupled to the surface of the substrate. The deformable layer comprises at least a thickness of first material. A control layer is coupled to the deformable layer to form a sandwich structure including at least the substrate, the deformable layer and the control layer. The control layer is made of at least a thickness of second material. At least one fiducial marking is provided within either the control layer or the deformable layer or the substrate. The fiducial marking is characterized by a visual pattern provided in a volume surrounded wholly or partially by at least the substrate, the first material, or the second material. Preferably, a fluid is disposed within the open volume of the one fiducial marking. The fluid is characterized by a refractive index that is substantially lower than its surrounding regions, e.g., first thickness of material, second thickness of material, substrate. That is, the refractive index may be associated with air or other like fluid and the surrounding regions are characterized by a refractive index associated with a solid according to a specific embodiment.

Numerous benefits are achieved using the present invention over conventional techniques. The invention provides at least one way to form alignment patterns for a deformable active region for a microfluidic system according to a specific embodiment. The invention can also use conventional materials, which are relatively easy to use. Preferably, the invention provides at least two sets of alignment marks, including one set of spatially disposed fiducial markings and a pre-designated pattern, which has an edge and center region. Depending upon the embodiment, one or more of these benefits may exist. These and other benefits have been described throughout the present specification and more particularly below.

In yet another specific embodiment, the invention provides a method for processing a microfluidic device, e.g., microfluidic chip, biological chip. The method includes providing a flexible substrate including a first plurality of fiducial markings, and determining a first plurality of actual locations corresponding to the first plurality of fiducial markings respectively. The first plurality of fiducial markings is associated with a first plurality of design locations respectively. Additionally, the method includes processing information associated with the first plurality of actual locations and the first plurality of design locations, and determining a transformation between a design space and a measurement space. The design space is associated with the first plurality of design locations, and the measurement space is associated with the first plurality of actual locations. Moreover, the method includes performing a first alignment to the flexible substrate based on at least information associated with the transformation between the design space and the measurement space. Also, the method includes acquiring a first plurality of images of the first fiducial marking, processing information associated with the first plurality of images, performing a second alignment to the flexible substrate based on at least information associated with the first plurality of images, and acquiring a second image of the flexible substrate.

According to yet another embodiment, a method for processing a microfluidic device includes providing a flexible substrate including at least three fiducial markings, a first additional fiducial marking, and a first chamber capable of holding a fluid therein. Additionally, the method includes determining a transformation between a design space and a measurement space based on at least information associated with the at least three fiducial markings, and performing a first alignment to the flexible substrate based on at least information associated with the transformation between the design space and the measurement space. Moreover, the method includes acquiring at least a first image of the first additional fiducial marking associated with the first chamber, performing a second alignment to the flexible substrate based on at least information associated with the first image, and acquiring a second image of the first chamber associated with the flexible substrate.

According to yet another embodiment, the invention provides a system for processing one or more microfluidic devices. The system includes one or more computer-readable media and a stage for locating a flexible substrate. The flexible substrate comprises at least three fiducial markings, a first additional fiducial marking, and a first chamber capable of holding a fluid therein. The one or more computer-readable media include one or more instructions for providing a flexible substrate, and one or more instructions for determining a transformation between a design space and a measurement space based on at least information associated with the at least three fiducial markings. Additionally, the one or more computer-readable media include one or more instructions for performing a first alignment to the flexible substrate based on at least information associated with the transformation between the design space and the measurement space, one or more instructions for acquiring at least a first image of the first additional fiducial marking associated with the first chamber, one or more instructions for performing a second alignment to the flexible substrate based on at least information associated with the first image, and one or more instructions for acquiring a second image of the first chamber associated with the flexible substrate.

According to yet another embodiment of the present invention, a method for processing a microfluidic device includes providing a flexible substrate (e.g., polymer, silicone based, rubber) comprising one or more well regions and a plurality of fiducial marks. The well regions are capable of holding a fluid therein and at least three of the fiducial marks are within a vicinity of one of the well regions. Preferably, the flexible substrate has been provided on a rigid member. The method includes locating the flexible substrate on a stage and capturing an image of at least the three fiducial marks within the vicinity of the one well region of the flexible substrate to generate a mapping from a design space to a measurement space. The method also includes aligning the flexible substrate to an image acquisition location using at least the mapping from the design space and one additional fiducial mark, wherein the at least one additional fiducial mark is associated with the one well region. The method also includes acquiring a high-resolution image of at least the one well region and storing the high-resolution image in a memory.

In yet another alternative specific embodiment, the invention provides a system for processing one or more microfluidic devices. The system includes one or more computer memories. The system also includes a stage for locating a flexible substrate, which has one or more well regions and a plurality of fiducial marks. The well regions are capable of holding a fluid therein. At least three of the fiducial marks are within a vicinity of one of the well regions. The one or more computer memories comprise one or more computer codes. The one or more computer codes include a first code directed to capturing an image of at least the three fiducial marks within the vicinity of the one well region of the flexible substrate to generate a mapping from a design space to a measurement space. A second code is directed to aligning the flexible substrate to an image acquisition location using at least the mapping from the design space and one additional fiducial mark, wherein the at least one additional fiducial mark is associated with the one well region. A third code is directed to acquiring a high-resolution image of at least the one well region. A fourth code is directed to storing the high-resolution image in a memory. Depending upon the embodiment, there may also be other computer codes to implement the functionality described herein as well as outside of the specification.

In yet another alternative specific embodiment, the invention provides method of processing a biological microfluidic device. The method includes providing a deformable substrate comprising one or more metering cells, which are capable of containing a fluid therein. The method also includes locating the deformable substrate on a stage translatable in x, y, and z directions and translating the stage to image at least four fiducial marks associated with the deformable substrate. The method determines x, y, and z positions (or other like spatial positions) of the at least four fiducial marks according to a preferred embodiment. The method computes a non-planar mapping between a design space and a measurement space based on the x, y, and z positions of the at least four fiducial marks and translates the stage to an image acquisition position calculated using the non-planar mapping. A step of capturing an image of at least one metering cell is included.

According to yet another embodiment of the present invention, a method for producing an image of an object within a chamber of a microfluidic device includes providing the microfluidic device. The microfluidic device has x, y, and z dimensions and a chamber depth center point located between a top wall and a bottom wall of the chamber along the z dimension. The chamber depth center point is located a known z dimension distance from an optically detectable fiducial marking embedded within the microfluidic device at a z depth. Additionally, the method includes placing the microfluidic device within an imaging system. The imaging system includes an optical device capable of detecting the fiducial marking and transmitting the image of the object. The optical device defines an optical path axially aligned with the z dimension of the microfluidic device and has a focal plane perpendicular to the optical path. When the focal plane is moved along the optical path in line with the fiducial marking, the fiducial marking is maximally detected when the focal plane is at the z depth in comparison to when the focal plane is not substantially in-plane with the z depth. Additionally, the imaging system includes an image processing device in communication with the optical device. The image processing device is able to control the optical device to cause the focal plane to move along the z axis and move the focal plane to maximally detect the fiducial marking. The image processing device is further able to transmit the image of the object. Additionally, the method includes controlling the optical device with the image processing device to cause the focal plane to move along the optical path until the optical device maximally detects the fiducial marking. Moreover, the method includes controlling the optical device with the image processing device to move the focal plane along the optical path the z dimension distance to cause the field depth center point to be located at the chamber depth center point. Moreover, the method includes imaging the object within the chamber while the focal plane is located at the chamber depth center point.

According to yet another embodiment of the present invention, a system for producing an image of an object within a chamber of a microfluidic device includes the microfluidic device. The microfluidic device has x, y, and z dimensions and a chamber depth center point located between a top wall and a bottom wall of the chamber along the z dimension. The chamber depth center point is located a known z dimension distance from a optically detectable fiducial marking embedded within the microfluidic device at a z depth. Additionally, the system includes an imaging system for placing the microfluidic device therein. The imaging system includes an optical device capable of detecting the fiducial marking and transmitting the image of the object. The optical device defines an optical path axially aligned with the z dimension of the microfluidic device and having a focal plane. When the focal plane is moved along the optical path in line with the fiducial marking, the fiducial marking is maximally detected when the focal plane is substantially in-plane with the z depth as compared to when the field depth center point is not substantially in-plane with the z depth. Additionally, the imaging system includes an image processing device in communication with the optical device. The image processing device is able to control the optical device to cause the focal plane to move along the z axis and move the field depth center point to maximally detect the fiducial marking. The image processing device is able to transmit the image of the object. The image processing device is in operable communication with the optical device to cause the focal plane to move along the optical path until the optical device maximally detects the fiducial marking. When the image processing device causes the optical device to move the focal plane along the optical path the z dimension distance, the focal point is located at said chamber depth center point.

According to yet another embodiment of the present invention, a method for producing an image of a chamber within a microfluidic device includes imaging the microfluidic device to produce an image using an imaging system having an optical path in the z plane of the microfluidic device, and mapping from the image a first set of coordinates of the microfluidic device to determine whether the microfluidic device is skewed or distorted when compared to a coordinate map of an ideal microfluidic device. Additionally, the method includes positioning the microfluidic device so as to position the chamber within the optical path based on a matrix transformation calculated coordinate position determined by computing a matrix transformation between the first set of coordinates of the microfluidic device and the coordinate map of the ideal microfluidic device. Moreover, the method includes obtaining a time zero image of the microfluidic device chamber. The time zero image contains images of artifacts present in the microfluidic device. Also, the method includes obtaining a second image of the microfluidic device chamber and subtracting the first image of the microfluidic device chamber from the second image of the microfluidic chamber to produce an image of the chamber without time zero artifacts.

Numerous benefits are achieved using the present invention over conventional techniques. Some embodiments provide alignment and/or focus based on mapping between the design space and the measurement space. The transformation between the design space and the measurement space uses, for example, at least three fiducial markings. Certain embodiments provide accurate focusing by acquiring and analyzing a plurality of images along at least one dimension. Some embodiments of the present invention perform alignment and focusing on a microfluidic device including at least one flexible substrate. The alignment and focusing take into account the deformation of the flexible substrate. Certain embodiments improve throughput in imaging system. For example, the imaging system uses a computer system to automatically perform alignment and focusing. In another example, mapping from the design space to the measurement space increases the accuracy of stage positioning, and thereby, the efficiency of high-resolution image acquisition. Depending upon the embodiment, one or more of these benefits may exist. These and other benefits have been described throughout the present specification and more particularly below.

Various additional objects, features and advantages of the present invention can be more fully appreciated with reference to the detailed description and accompanying drawings that follow.

BRIEF DESCRIPTION OF THE DRAWINGS

FIG. 13A is a simplified top-view diagram of a microfluidic system including carrier and identification code according to an embodiment of the present invention;

DETAILED DESCRIPTION OF THE INVENTION

According to the present invention, techniques for microfluidic systems, including a microfluidic chip or circuit, are provided. More particularly, the invention provides a microfluidic structure and method of manufacture, and a system and method for imaging a microfluidic device. Merely by way of example, the fiducial markings are used for processing and imaging a microfluidic chip, but it would be recognized that the invention has a much broader range of applicability.

Method for Manufacturing Fluidic Chip

Figure 1:
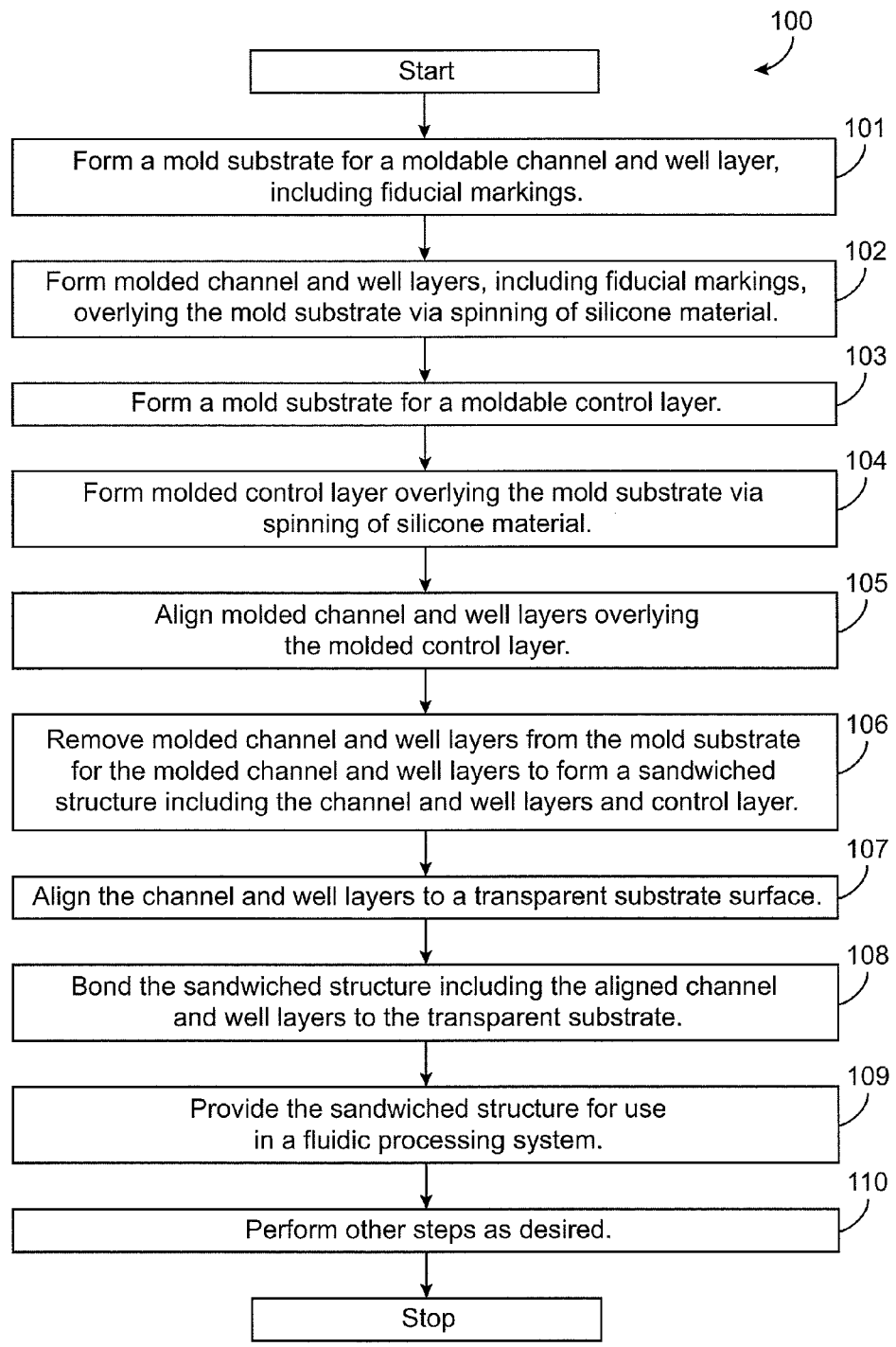
FIGS. 1-10 are simplified diagrams illustrating a method for fabricating a microfluidic system according to an embodiment of the present invention.

A method for manufacturing a fluidic chip according to an embodiment of the present invention may be outlined below. Certain details of the method 100 are also provided according to a flow diagram illustrated by FIG. 1, which is not intended to unduly limit the scope of the claims herein. One of ordinary skill in the art would recognize many variations, alternatives, and modifications.

1. Form a mold substrate for a moldable channel and well layer 101, including fiducial markings;
2. Form molded channel and well layers 102, including fiducial markings, overlying the mold substrate via spinning of silicone material;
3. Form a mold substrate for a moldable control layer 103;
4. Form molded control layer overlying the mold substrate via spinning of silicone material 104;
5. Align molded channel and well layers overlying the molded control layer 105;
6. Remove molded channel and well layers from the mold substrate for the molded channel and well layers to form a sandwiched structure including the channel and well layers and control layer 106;
7. Align the channel and well layers to a transparent substrate surface 107;
8. Bond the sandwiched structure including the aligned channel and well layers to the transparent substrate 108;
9. Provide the sandwiched structure for use in a fluidic processing system 109; and
10. Perform other steps 110, as desired.

The above sequence of steps provides a method for manufacturing a microfluidic system having molded channel, well, and control layers. In a specific embodiment, each of the molded channel, well, and control layers is deformable or elastic. That is, well regions may vary slightly from well to well throughout a single microfluidic system, which has been provided on a chip. To compensate for such deformable characteristic, the present system includes at least one or more fiducial markings that have been placed in predetermined spatial locations to be used with image processing techniques. These fiducial markings allow for any inherent errors caused by the deformable characteristic to be compensated at least in part using the image processing techniques. Further details of methods and resulting structures of the present microfluidic system have been described throughout the present specification and more particularly below.

Method for Manufacturing Mold for Fluid Layer

Figure 2:
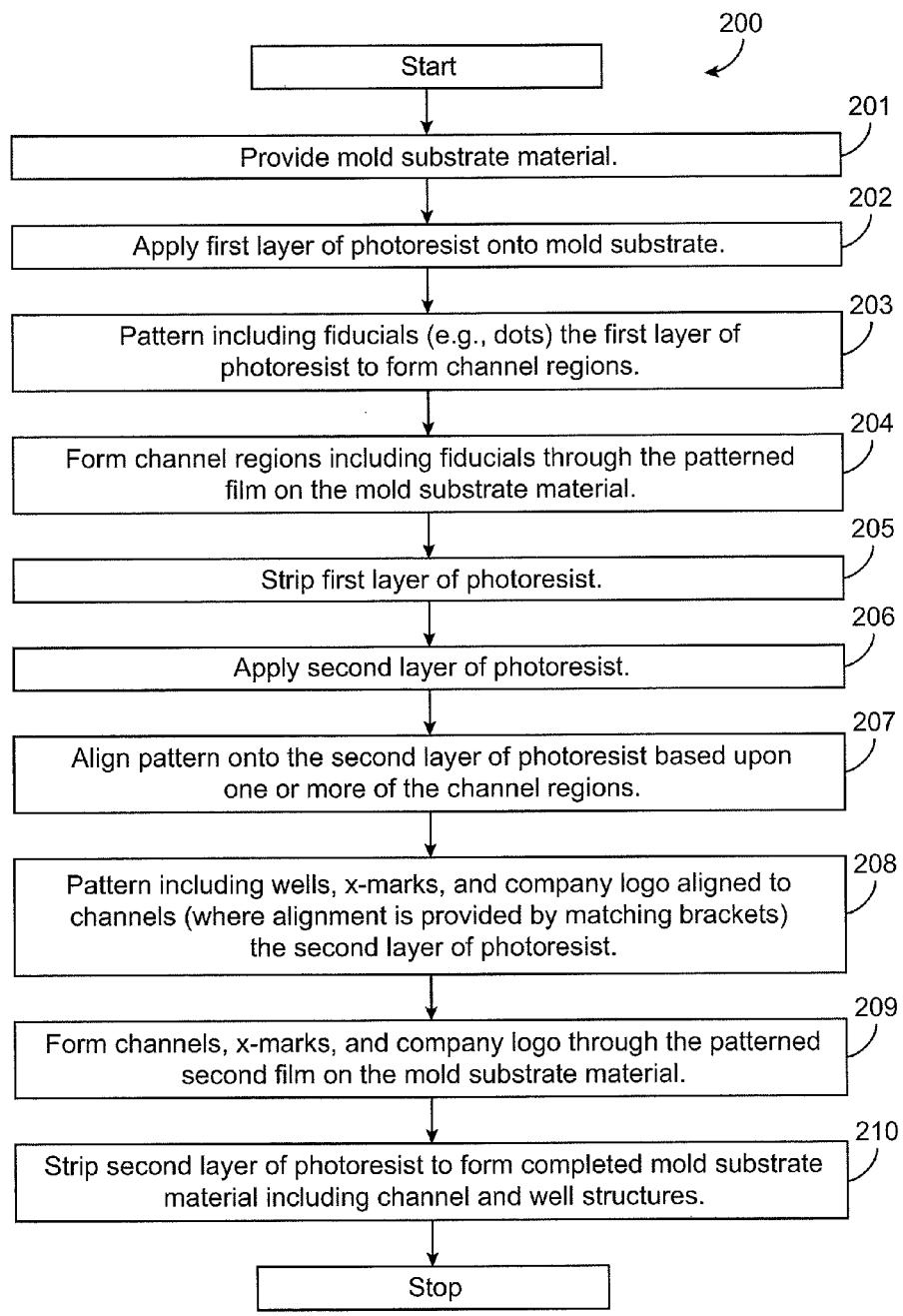

A method for manufacturing a mold for a fluid layer according to an embodiment of the present invention may be outlined below. Certain details of the method 200 are also provided according to a flow diagram illustrated by FIG. 2, which is not intended to unduly limit the scope of the claims herein. One of ordinary skill in the art would recognize many variations, alternatives, and modifications.

1. Provide mold substrate material 201;
2. Apply first layer of photoresist onto mold substrate 202;
3. Pattern including fiducials (e.g., dots) the first layer of photoresist to form channel regions 203;
4. Form channel regions including fiducials through the patterned film on the mold substrate material 204;
5. Strip first layer of photoresist 205;
6. Apply second layer of photoresist 206;
7. Align pattern onto the second layer of photoresist based upon one or more of the channel regions 207;
8. Pattern including wells, x-marks, and company logo aligned to channels (where alignment is provided by matching brackets) the second layer of photoresist 208;
9. Form channels, x-marks, and company logo through the patterned second film on the mold substrate material 209;
10. Strip second layer of photoresist to form completed mold substrate material including channel and well structures 210; and
11. Perform other steps, as desired.

The above sequence of steps provides a method for manufacturing a mold for a molded channel and well layers according to a specific embodiment. In a specific embodiment, each of the molded channel and well layers is deformable or elastic. To compensate for such deformable characteristic, the present system includes at least one or more fiducial markings that have been placed in predetermined spatial locations to be used with image processing techniques. These fiducial markings allow for any inherent errors caused by the deformable characteristic to be compensated at least in part using the image processing techniques. Further details of methods and resulting structures of the present microfluidic system have been described throughout the present specification and more particularly below.

Method for Manufacturing Control Layer

Figure 3:
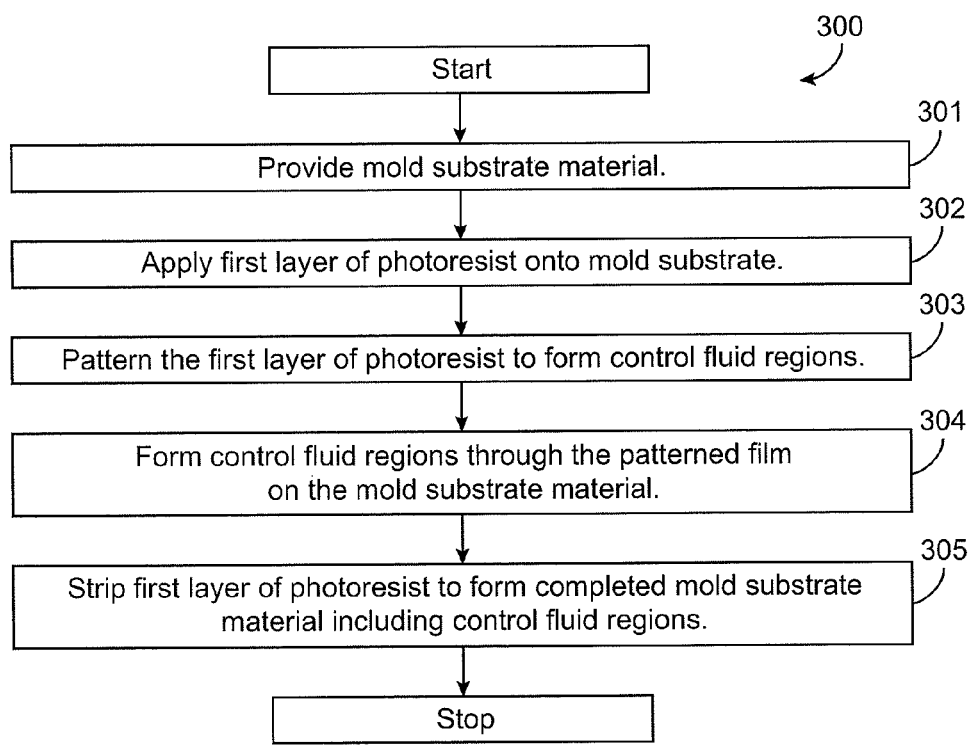

A method for manufacturing a mold for a control layer according to an embodiment of the present invention may be outlined below. Certain details of the method 300 are also provided according to a flow diagram illustrated by FIG. 3, which is not intended to unduly limit the scope of the claims herein. One of ordinary skill in the art would recognize many variations, alternatives, and modifications.

1. Provide mold substrate material 301;
2. Apply first layer of photoresist onto mold substrate 302;
3. Pattern the first layer of photoresist to form control fluid regions 303;
4. Form control fluid regions through the patterned film on the mold substrate material 304;

5. Strip first layer of photoresist to form completed mold substrate material including control fluid regions 305; and 6. Perform other steps, as desired.

The above sequence of steps provides a method for manufacturing a mold for a molded control layer according to a specific embodiment. In a specific embodiment, the control layers is deformable or elastic. To compensate for such deformable characteristic, the present system includes at least one or more fiducial markings that have been placed in predetermined spatial locations to be used with image processing techniques. These fiducial markings allow for any inherent errors caused by the deformable characteristic to be compensated at least in part using the image processing techniques. Further details of methods and resulting structures of the present microfluidic system have been described throughout the present specification and more particularly below.

FIGS. 1-11 are simplified diagrams illustrating a method for fabricating a microfluidic system according to an embodiment of the present invention. These diagrams are merely examples, which should not unduly limit the scope of the claims herein. One of ordinary skill in the art would recognize many variations, modifications, and alternatives. As noted above, FIGS. 1 through 3 have been described. Certain features with regard to illustrating features of the fluidic system have been provided by way of FIGS. 4 through 11. For easy viewing, the left side illustrates an overview of the entire substrate, including patterns, while the right side illustrates a portion of the pattern that is pertinent according to a feature being described.

Figure 4:
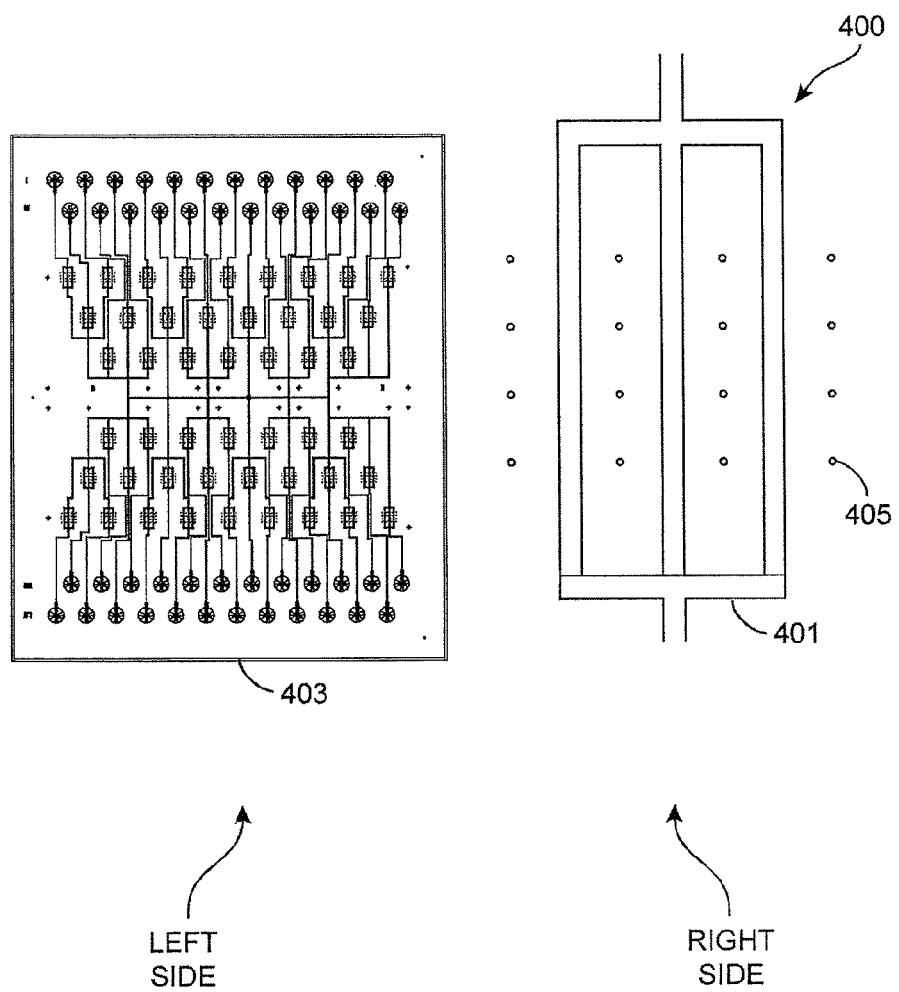

Referring to FIG. 4, fluid channel layer is illustrated. The fluid channel layer (or control layer) includes fluid channels 401 to deliver fluid throughout the substrate 403. Fiducial markings in shape of circles 405 are used to locate the channels themselves. These circles are part of the fluid channel layer mask and are transferred with the channels onto the substrate. The circles are recessed regions, which do not extend all the way through the layer, in preferred embodiments.

Figure 5:
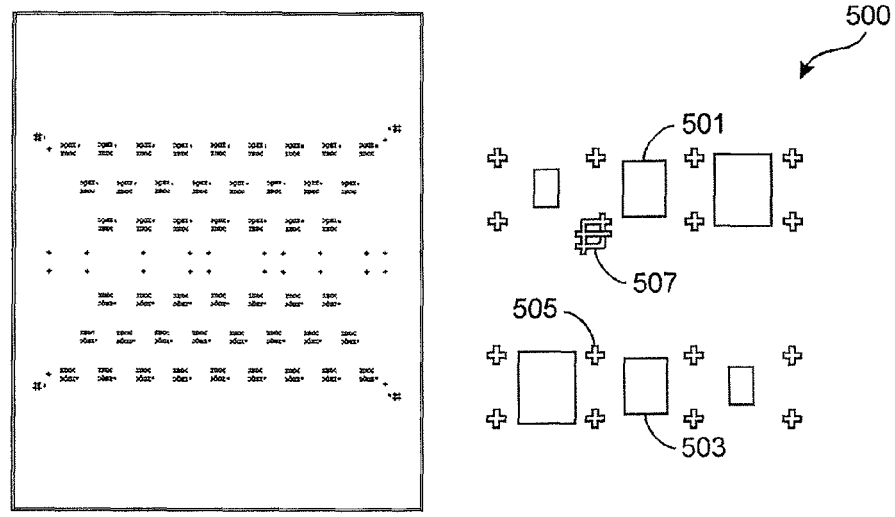

Referring to FIG. 5, a well layer 501 including well regions 501, 503 on the substrate are illustrated. The well layer includes the well regions and the company logo 507 (which serves as a predetermined fiducial marking according to preferred embodiments) that enables x-y spatial location of a metering cell. In addition the logo is also used for focusing onto the wells as the logo height is the same height as the wells. The well layer also includes a plurality of fiducial markings 505, e.g., crosses. Such crosses are located within a vicinity of each of the well regions. The crosses are at a finite distance and are translated from the mask to the substrate. When using image processing algorithms to locate one or more of the wells, the crosses can be used as a reference to well location. As shown, each of the crosses are located in a spatial manner around a periphery of the well region. That is, each of the crosses occupies a corner region that is not active and is free from the well itself.

Figure 6:
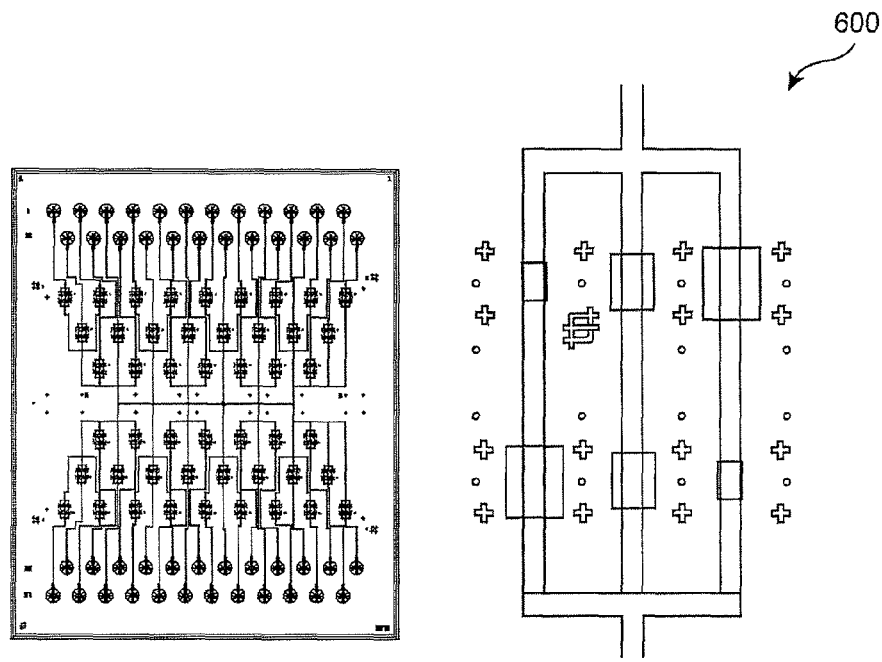

Referring to FIG. 6, alignment occurs between the fluid channel layer and well layer according to a specific embodiment. Here, the method aligns these two layers at the substrate mold making process. The well layer has a different thickness and shape than the fluid layer. The well layer produces sharp edges while fluid channel layer produces round edges. Preferably, a goal is to have the wells overlaying the channels in order for the channels to distribute fluids into the wells. The well layer mask is aligned to the fluid layer to place wells over the fluid channels, as shown. Alignment is done by matching the frame of the well layer to the frame of the fluid channel layer.

Figure 7:
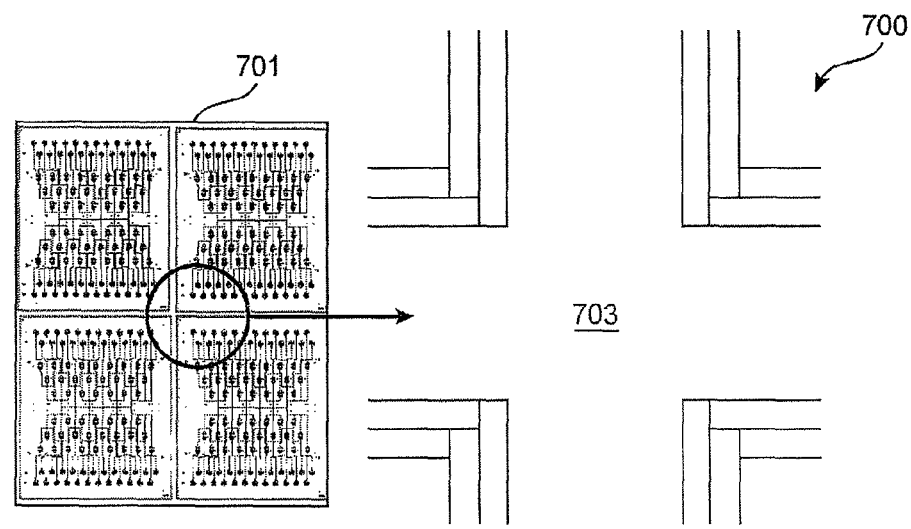

The method generally forms more than one design 701 on a substrate material as shown in FIG. 7. Each of these designs can be separated using regions 703 according to a preferred embodiment. The method performs final assembly after silicone (or other like material) has been poured separately over the fluid/well layer mold and the control layer mold. Preferably, the final assembly is made when the control layer of silicone is aligned to the fluid layer of silicone. Matching alignment marks are located on the fluid and control layer that need to overlay each other for proper alignment.

Figure 8:
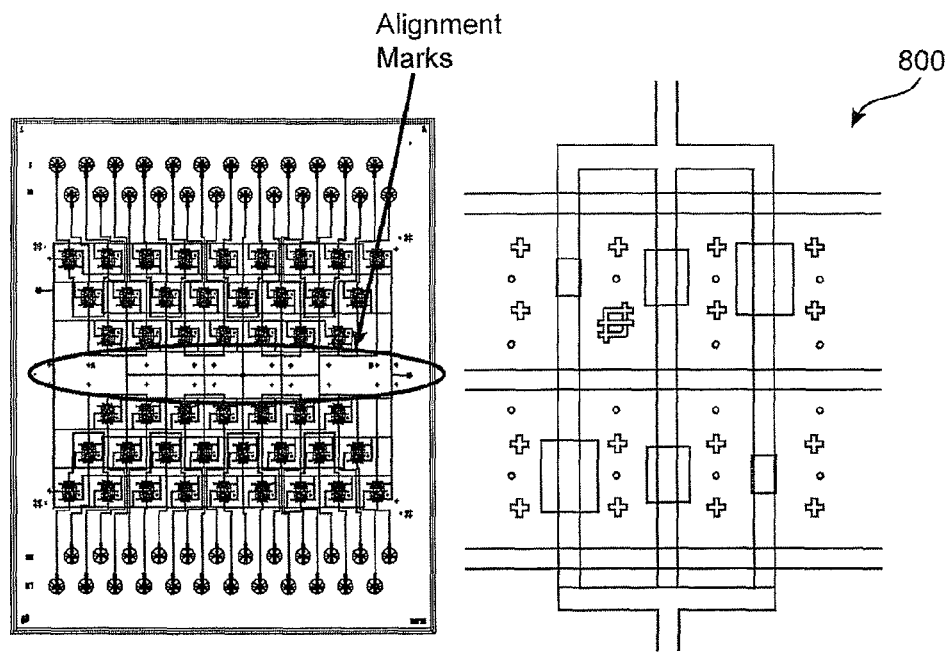
Figure 9:
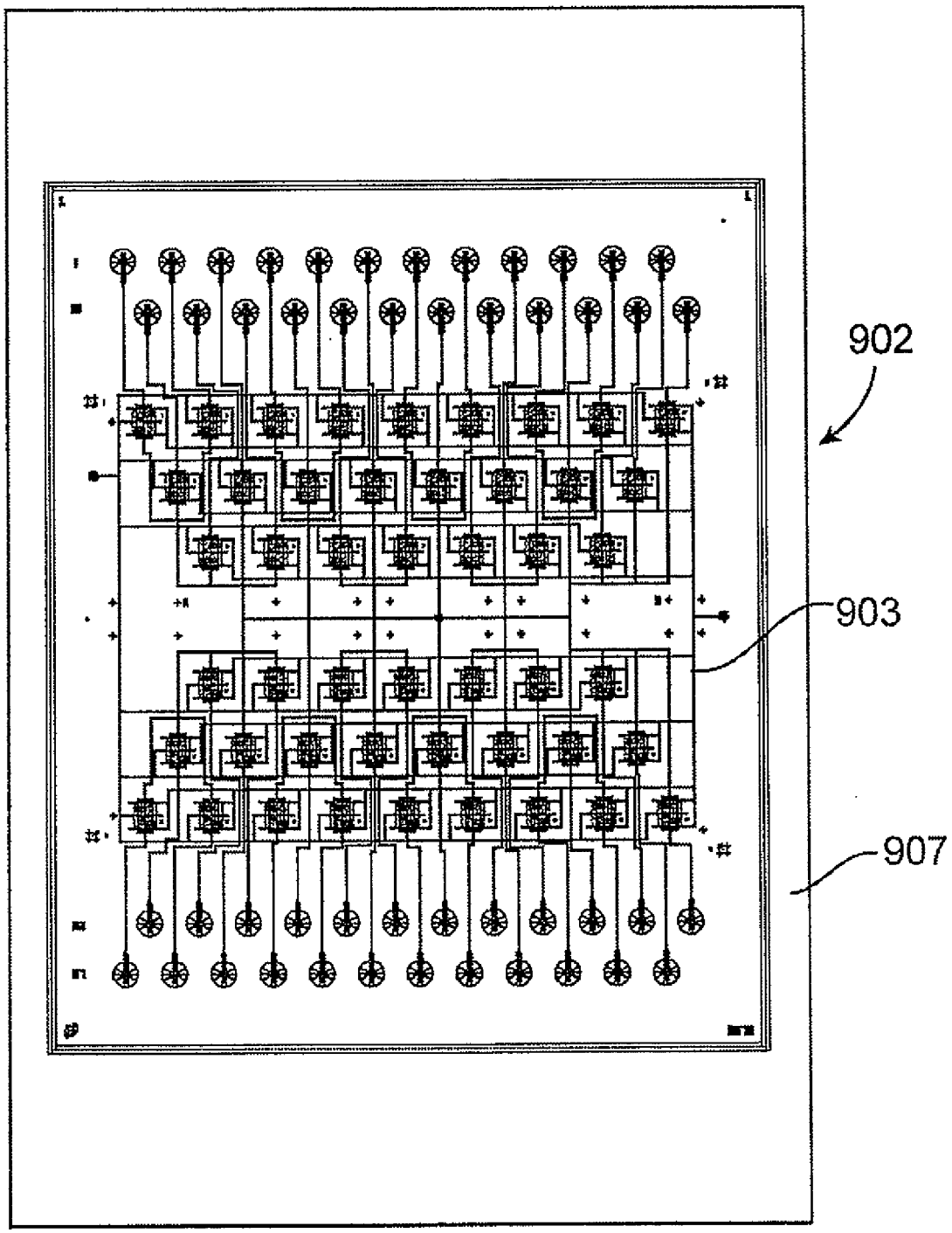

To align the patterned substrate to the blank substrate, the method includes placing a template of the patterned substrate underneath the blank substrate, which is transparent, as illustrated by FIG. 8. The template allows carrier top access to reagent inputs. In addition proper alignment of the patterned substrate onto the blank transparent substrate enables the imaging station to view the global fiducials on the chip through the carrier bottom. As shown, FIG. 9 illustrates the patterned substrate, including wells and channels, overlying the transparent substrate. Details of the fiducial markings are provided throughout the present specification and more particularly below.

Figure 10:
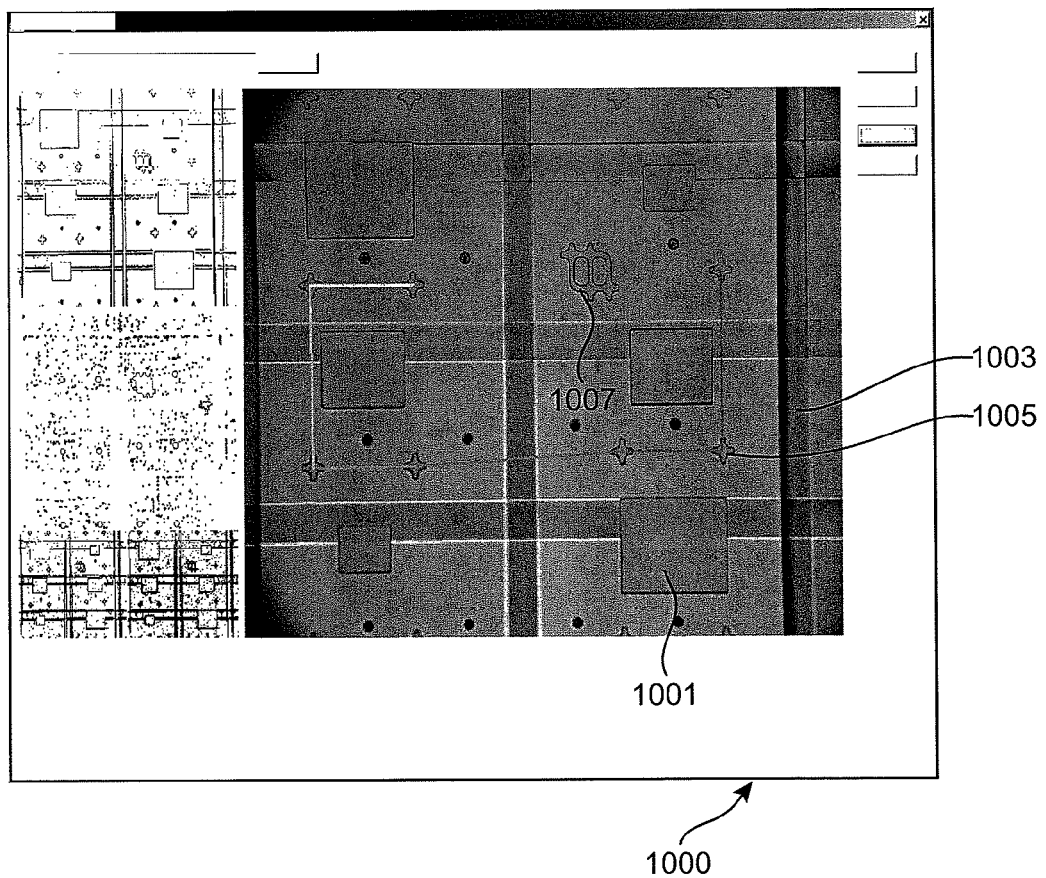

FIG. 10 is a simplified top-view diagram 1000 of a completed microfluidic system including well 1001 and channel regions 1003. As shown, fiducial markings 1005 are disposed spatially around a periphery of the well region. The system also has company log 1007, which is a predetermined fiducial marking, which is larger in size than the other fiducial markings. The predetermined fiducial marking has one or more edges and a center region, among other features, as needed. Of course, one of ordinary skill in the art would recognize many other variations, modifications, and alternatives. Specific details with regard to the present system are also provided using the side-view diagram illustrated below.

Figure 11:
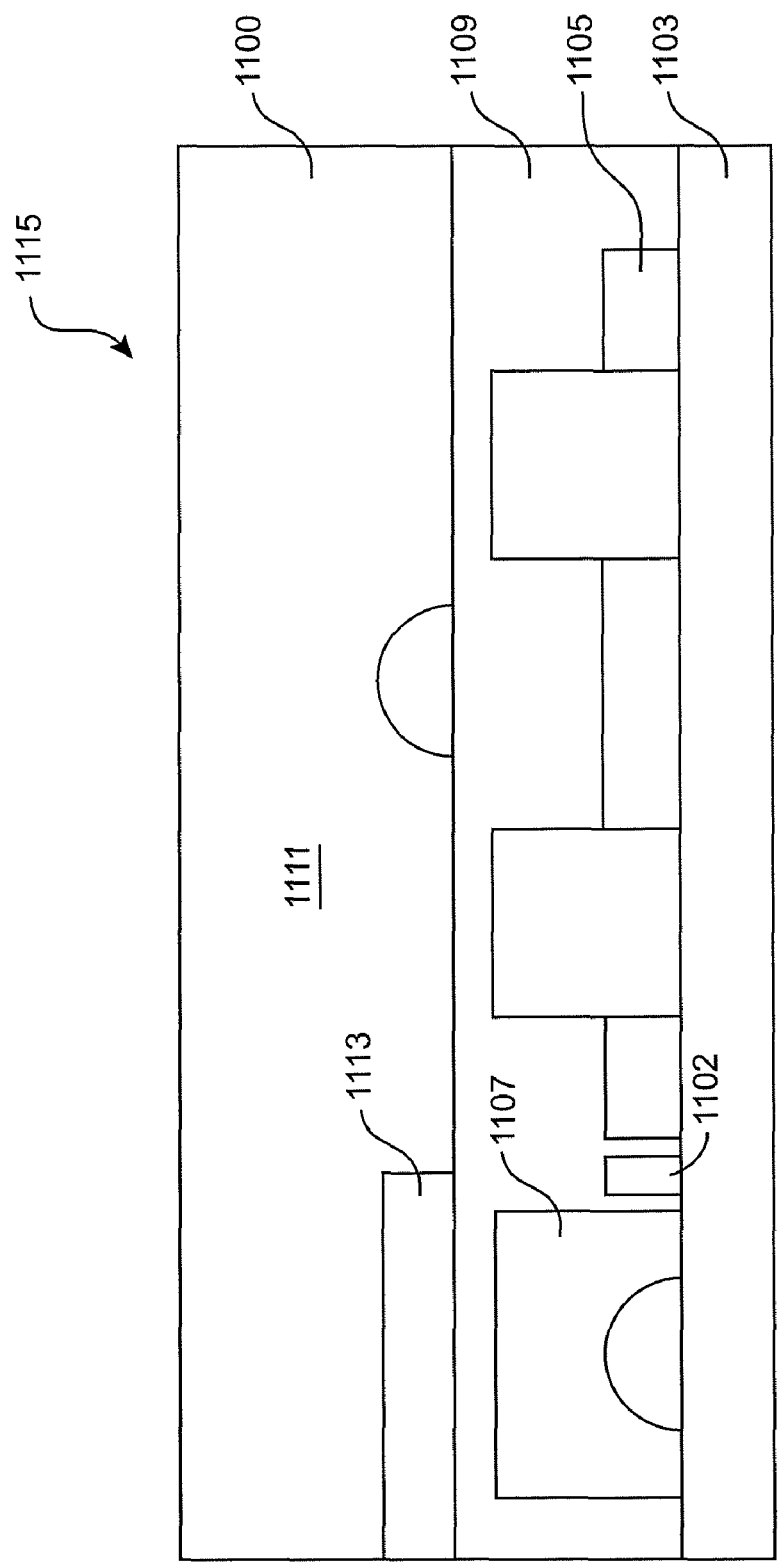
FIG. 11 is a simplified cross-sectional view diagram of a microfluidic system according to an embodiment of the present invention.

FIG. 11 is a simplified cross-sectional view diagram 1115 of a microfluidic system 1100 according to an embodiment of the present invention. This diagram is merely an example, which should not unduly limit the scope of the claims herein. One of ordinary skill in the art would recognize many variations, modifications, and alternatives. As shown, the system includes a glass substrate 1103 or any like transparent substrate material, which can act as a handle substrate. Overlying the handle substrate is fluid channel 1105 and well layer 1107. The fluid channel and well layer have been provided on a single layer 1109 or can be multiple layers. The fluid channel has a depth that is less than the well, which extends into the single layer. Preferably, the fluid channel and well layer are made using a suitable material such as silicone, silicon rubber, rubber, plastic, PDMS, or other polymeric material. Preferably, the material is also transparent, but may be deformable or alternatively flexible in characteristic. The system also has a control layer 1111, which includes control channel 1113. Preferably, the control layer is made using a suitable material such as silicone, silicon rubber, rubber, plastic, PDMS, or other polymeric material. Depending upon the embodiment, there may also be other features in the system.

One 1102 of a plurality of fiducial markings is also shown. The marking is at a vicinity of the well region and also has a height relative to the wells that are substantially similar. That is, optically the height of the marking is about the same as the well relative to a plane parallel to the substrate. Alternatively, the marking may be formed based upon a predetermined off-set relative to the plane parallel to the substrate in other embodiments. Certain dimension are also shown, but are not intended to be limiting in any manner. Depending upon the embodiment, there can be many variations, alternatives, and modifications.

Other embodiments of the present invention are provided below.

Figure 12:
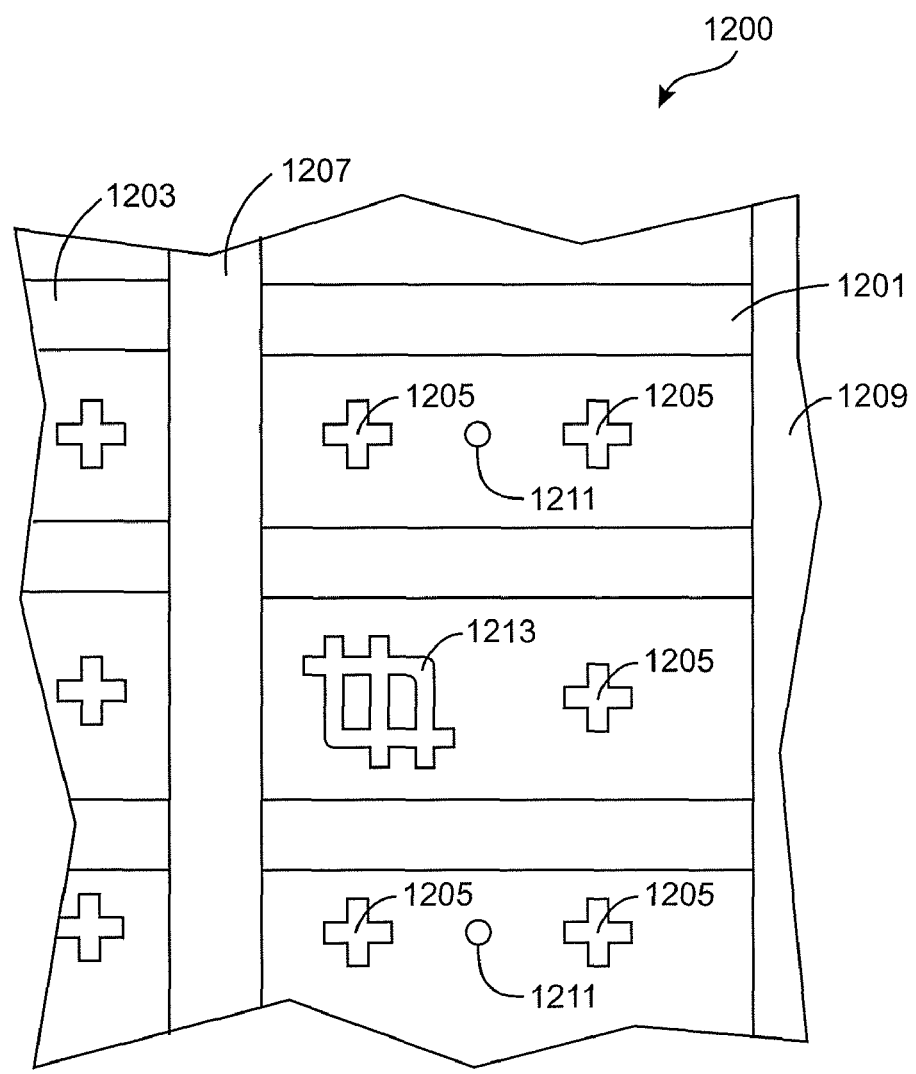
FIG. 12 is a simplified top-view diagram of a microfluidic system according to an alternative embodiment of the present invention.

FIG. 12 is a simplified top-view diagram of a microfluidic system according to an alternative embodiment of the present invention. This diagram is merely an example, which should not unduly limit the scope of the claims herein. One of ordinary skill in the art would recognize many variations, modifications, and alternatives. As shown, the system comprises a biological substrate 1200. The substrate includes a rigid substrate material, which has a surface region. The substrate is capable of acting as a handle substrate. The rigid substrate can be made of a suitable material such as a glass, a plastic, silicon, quartz, multi-layered materials, or any combination of these, and the like. Of course, the type of substrate used depends upon the application.

The substrate also includes a deformable fluid layer coupled to the surface region. Preferably, the fluid layer is attached using a glue layer or other attachment technique. One or more well regions are formed in a first portion of the deformable fluid layer. The one or more well regions is capable of holding a fluid therein. One or more channel regions is formed in a second portion of the deformable fluid layer, The one or more channel regions is coupled to one or more of the well regions. The channel regions include protein channels 1201 and reagent channels 1203. Other channel regions can also be included.

The fluid layer includes active and non-active regions. An active region is formed in the deformable fluid layer. The active region includes the one or more well regions. A non-active region is formed in the deformable fluid layer. The non-active region is formed outside of the first portion and the second portion. The term "active" and "non-active" are merely used for illustration purposes and should not limit the scope of the claims herein. The non-active region generally corresponds to regions free from use of fluids or other transport medium, and the like.

The substrate includes a plurality of fiducial markings. Each of the fiducial markings is selectively placed within a certain layer region. In a specific embodiment, a first fiducial marking 1205 is formed within the non-active region and disposed in a spatial manner associated with at least one of the channel regions. That is, the first fiducial marking is within the channel regions. Preferably, the first fiducial marking is a recessed region that includes a selected width and depth. The recessed region forms a pattern to be captured by an image processing technique. In a specific embodiment, a second fiducial marking 1213 is formed within the non-active region and disposed in a spatial manner associated with at least one of the well regions. That is, the second fiducial marking is within the channel regions. Preferably, the second fiducial marking is a recessed region that includes a selected width and depth. The recessed region forms a pattern to be captured by an image processing technique.

The substrate also has a control layer coupled to the fluid layer. The control layer includes one or more control regions. The control layer includes interface control line 1207 and containment control line 1209. Other control lines can also be included. Preferably, a third fiducial marking 1211 is formed within the control layer. Preferably, the third fiducial marking is a recessed region that includes a selected width and depth. The recessed region forms a pattern to be captured by an image processing technique. Further details of the substrate can be found throughout the present specification and more particularly below.

Figure 13:
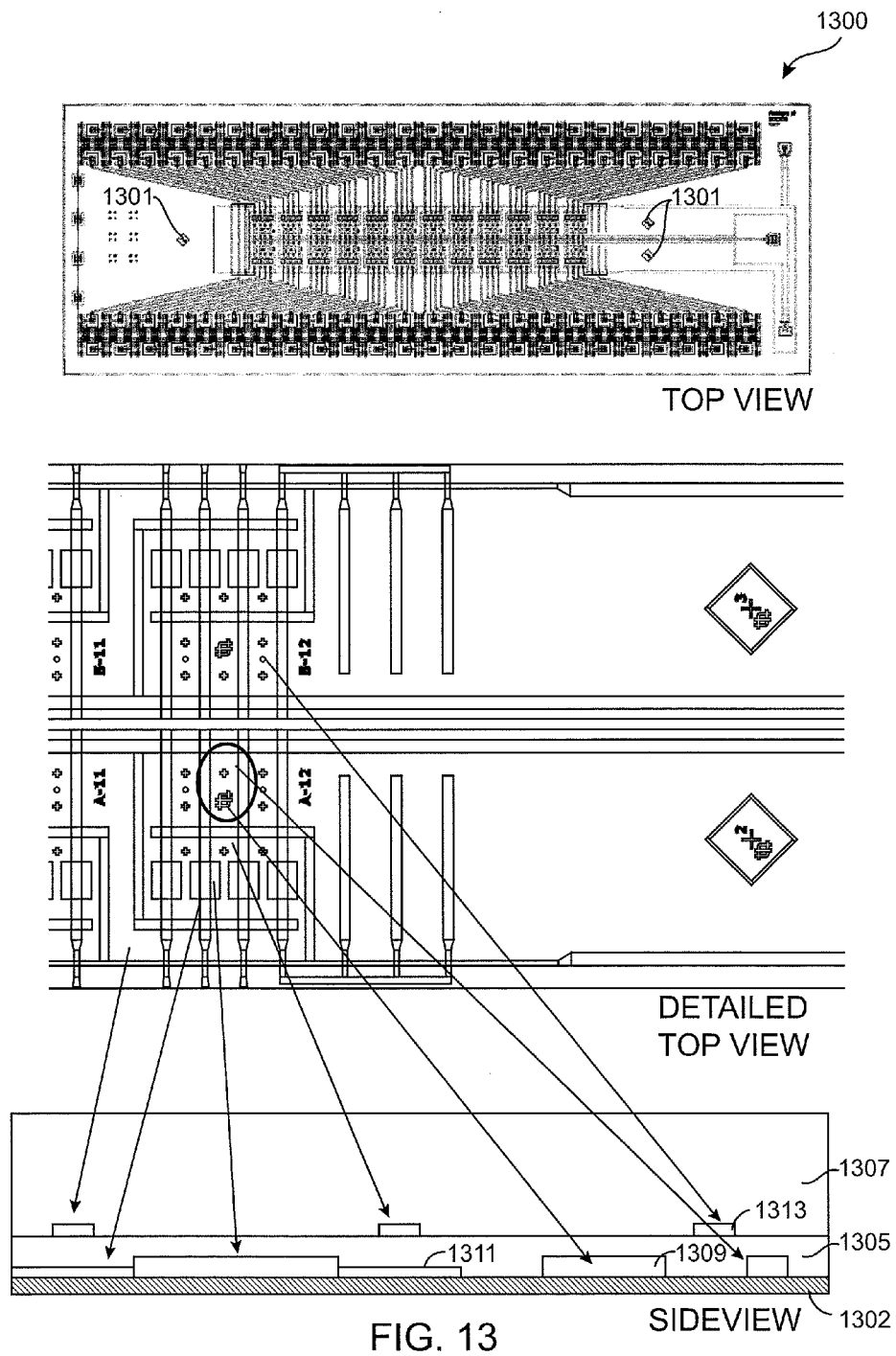
FIG. 13 is a simplified top and side-view diagram of a microfluidic system according to an alternative embodiment of the present invention.

FIG. 13 is a simplified top and side-view diagram 1300 of a microfluidic system according to an alternative embodiment of the present invention. This diagram is merely an example, which should not unduly limit the scope of the claims herein. One of ordinary skill in the art would recognize many variations, modifications, and alternatives. As shown, the diagram includes a "top-view," a "detailed top view" and "side view" of fluidic microstructures according to embodiments of the present invention. As shown, the system also includes global fiducials 1301. The global fiducials are used for rough alignment purposes, although may be used for fine alignment as well. In one embodiment, the global fiducials by a spatial dimension of greater than 100 µm and less than 250 µm. For example, the global fiducials include a length and a width of about 180 µm and 160 µm respectively. In another embodiment, the global fiducials are characterized by a depth of at least 10 µm within a thickness of the non-active region. For example, the global fiducials include a thickness of about 20 µm and are within the deformable layer 1305 as shown. The side view diagram includes a substrate 1302, which is preferably rigid, with an upper surface region. The rigid substrate can be made of a suitable material such as a glass, a plastic, silicon, quartz, multi-layered materials, or any combination of these, and the like. Of course, the type of substrate used depends upon the application.

The substrate also includes a deformable fluid layer coupled to the surface region. Preferably, the fluid layer is attached using a glue layer or other attachment technique. One or more well regions are formed in a first portion of the deformable fluid layer. The one or more well regions 1309 is capable of holding a fluid therein. As shown, the well region has a certain thickness within the deformable layer. One or more channel regions 1311 is formed in a second portion of the deformable fluid layer. The one or more channel regions is coupled to one or more of the well regions. The channel regions include protein channels and reagent channels. Other channel regions can also be included. As shown, the channel regions are not as thick as the well regions. The deformable layer includes an upper surface, which couples to control layer 1307. As shown, the control layer includes a plurality of control channels 1313.

Fiducial markings are selectively placed in a spatial manner on the microfluidic system. In a specific embodiment, the global alignment fiducial marking is formed in the deformable layer within a vicinity of a well region. A first fiducial marking is placed within a vicinity of the well region. In one embodiment, four wells form a metering cell. The metering cell has a length and a width each about 2 µm. The first fiducial marking is placed substantially at the center of the metering cell. A second fiducial marking may be placed within a vicinity of the channel region within the deformable layer. A third fiducial marking may be placed within a vicinity of the control channel in the control layer. Depending upon the application, there may be variations, alternatives, and modifications. That is, two of the fiducial markings may be within a vicinity of the channel region and the third fiducial marking may be within a vicinity of the control channel in the control layer. Alternatively, two of the fiducial markings may be within a vicinity of the well region and the third fiducial marking may be within a vicinity of the control channel in the control layer. Preferably, the fiducial markings are placed within a vicinity of the region being examined, such as well or channel regions. The fiducial marking placed within the control layer or another layer serves as an alignment point to correct for depth of field or other optical characteristics.

As shown in FIGS. 1-13, various fiducial markings can be included in microfluidic systems. In one embodiment, preferably a fiducial marking comprises a recessed region in the deformable layer. The recessed region becomes a volume or open region surrounded by portions of the deformable layer or other layers. The volume or open region is preferably filled with a fluid such as a gas including air or other non-reactive fluid. The fluid also has a substantially different refractive index to light relative to the surrounding deformable layer. The open region is preferably filed with an air or air type mixture and has a low refractive index. Similarly, the fiducial marking in the control layer has similar characteristics according to a specific embodiment. In certain embodiments, the fiducial marking has sharp edges that highlight the marking from its surroundings. For example, the edges are preferably 90 degree corners or the like. Of course, one of ordinary skill in the art would recognize other variations, modifications, and alternatives.

Additionally, as shown in FIGS. 1-13, the fluid channel and well layer are made using a suitable material such as silicone, silicon rubber, rubber, plastic, PDMS, or other polymeric material in certain embodiments. The control layer can be made also using a suitable material such as silicone, silicon rubber, rubber, plastic, PDMS, or other polymeric material in some embodiments. In other embodiments, the fluid channel and well layer and the control layer are made of material, whose thermal coefficient is at least $10^{-4}$. For example, the thermal coefficient ranges from $10^{-4}$ to $10^{-3}$. In yet another example, the thermal coefficient equals about $3 \times 10^{-3}$. In yet other embodiments, the fluid channel and well layer and the control layer are made of material, whose Young's modulus is at most $5 \times 10^6$. For example, the Young's modulus ranges from $8 \times 10^4$ to $7.5 \times 10^5$.

Also, as shown in FIGS. 1-13, the microfluidic device includes the channel regions and well regions. These diagram are merely examples, which should not unduly limit the scope of the claims. One of ordinary skill in the art would recognize many variations, alternatives, and modifications. In certain embodiments, the channel regions and the well regions are interchangeable. The channels and the wells refer to recessed regions in the microfluidic device. In other embodiments, the microfluidic device uses channel regions to function as well regions. In yet other embodiments, the microfluidic device includes chambers that can be used as fluid channels, control channels, and wells.

FIG. 13A is a simplified top-view diagram of a microfluidic system including carrier and identification code according to an embodiment of the present invention. This diagram is merely an example, which should not unduly limit the scope of the claims herein. One of ordinary skill in the art would recognize other variations, modifications, and alternatives. As shown, a system 1350 includes a chip 1353, which has associated carrier 1351. The chip can be any one of the embodiments referred to as a microfluidic system herein as well as others. The chip generally includes a substrate, deformable layer, and control layer, among other features. The chip also has well regions coupled to channel regions in the deformable layer. The control layer is coupled to the deformable layer. The carrier includes various features such as inlets/outlets 1355 that couple to elements in the chip. The carrier also includes accumulation reservoirs 1357, which couple to the inlets/outlets. The carrier has an identification region 1358 that includes barcode or other identification element. Other identification features, which can be identified visually, may also be used. Further embodiments may also include other identification devices such as radio frequency identification, pattern recognition, and the like.

Preferably, the bar code is an encoded set of lines and spaces of different widths that can be scanned and interpreted into numbers to identify certain features of the microfluidic system. The barcode includes intrinsic and/or extrinsic information associated with the chip. The intrinsic information may be pattern recognition information and/or alignment information associated with the fiducial markings. That is, once identification and alignment of the system has occurred using at least the fiducial markings, such alignment information can be stored in memory of a computing or processing system according to an embodiment of the present invention. The alignment information can be used to more efficiently process the specific chip, including bar code, for certain applications. The alignment information associated with the fiducial markings can be stored in memory that is later retrievable using processing systems according to embodiments of the present invention. Further details of these processing systems can be found throughout the present specification and more particularly below.

Figure 14:
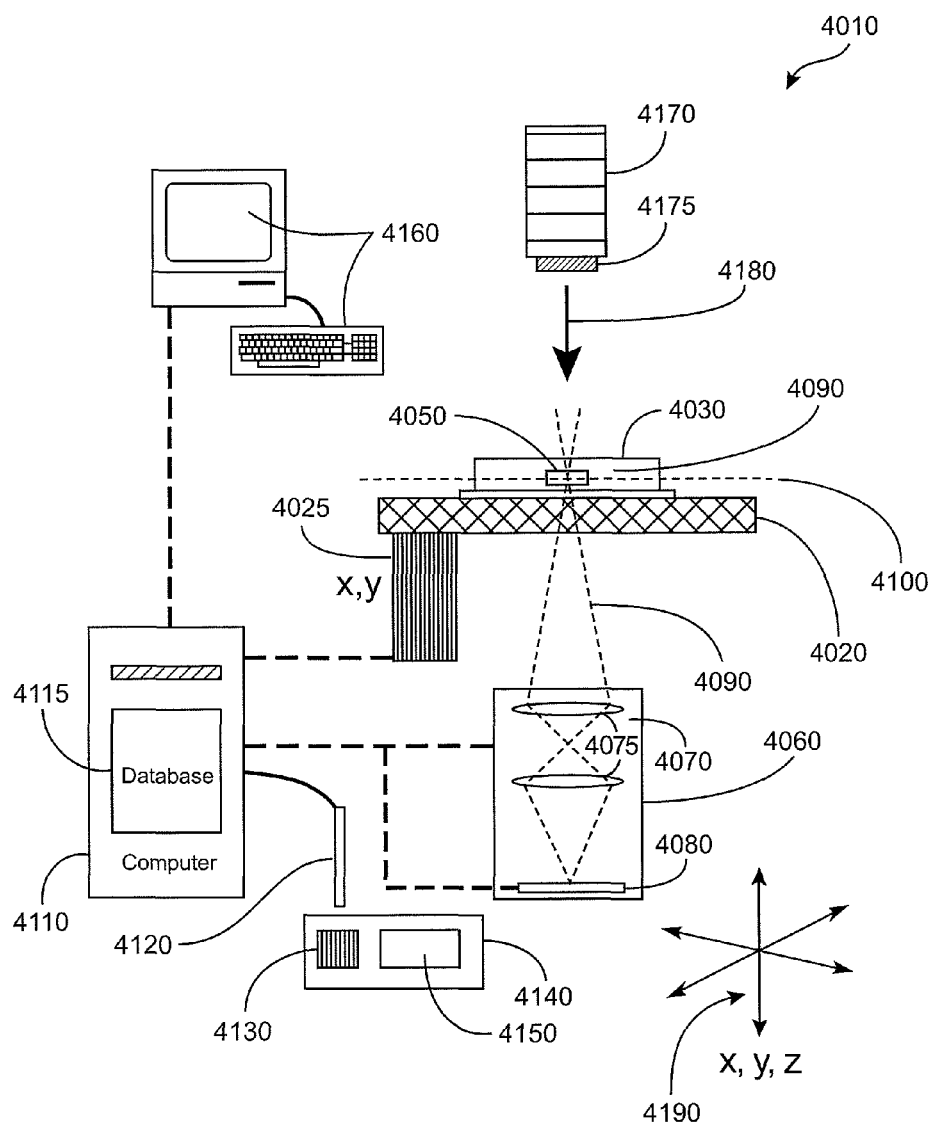
FIG. 14 is a simplified imaging system for imaging objects within a microfluidic device according to an embodiment of the present invention.

FIG. 14 is a simplified imaging system for imaging objects within a microfluidic device according to an embodiment of the present invention. This diagram is merely an example, which should not unduly limit the scope of the claims. One of ordinary skill in the art would recognize many variations, alternatives, and modifications.

As shown in FIG. 14, an imaging system 4010 includes a stage 4020. The stage 4020 is movable in x, y, and z dimensions, as shown by arrows 4190. The movement of the stage 4020 is caused by a stage drive 4025 under control of a computer system 4110. Additionally, the imaging system 4010 includes an imaging device 4060. The imaging device 4060 includes an lens system 4070 with lenses 4075 therein, and a detector 4080. The lens system 4070 is under control of the computer system 4110 to automatically adjust the focus of the lens system 4070 in response to image information gathered by the detector 4080. The image is communicated to the computer system 4110 and stored in a database 4115.

The lens system 4070 can focus on a microfluidic device 4030 by adjusting a focal plane 4100 in the z direction. For example, the focal plane is at a chamber centerline of the microfluidic device 4030. The microfluidic device 4030 is situated upon the stage 4020 and can have various structures. For example, the microfluidic device has a structure and is manufactured by a method as described in FIGS. 1-13. In another example, the microfluidic device 4030 has a chamber 4050 wherein an object, such as a protein crystal, may be formed or otherwise located. For example, the chamber 4050 is capable to hold a volume of fluid less than 1 nanoliter. A plurality of chambers can be combined to form a metering cell. The chamber 4050 has a chamber centerline that is located between a top wall and a bottom wall of the chamber 4050. For example, the chamber 4050 is a well region, a channel region, or both.

Moreover, the imaging system 10 includes an illumination device 4170 for producing an illumination beam 4180. For example, the illumination beam 4180 illuminates objects within the microfluidic device 4030. Additionally, the computer system 4110 may be in communication with an input/output device 4160 and a barcode reader 4120. The barcode reader 4120 can read a bar code 4130 on a microfluidic device 4140. For example, the microfluidic device 4140 is used as the microfluidic device 4030.

Although the above has been shown using a selected group of apparatuses for the system 4010, there can be many alternatives, modifications, and variations. For example, some of the apparatuses may be expanded and/or combined. Other apparatuses may be inserted to those noted above. Depending upon the embodiment, the arrangement of apparatuses may be interchanged with others replaced. Further details of these apparatuses are found throughout the present specification.

For example, the imaging system 4010 may be integrated into a larger robotic system, such as a rotating arm or railroad track type robotic system, to increase the throughput. The imaging system 4010 can communicate with the robotic system and control the flow of microfluidic devices into and out of the imaging system, acquire information about the microfluidic devices and their contents, and supply image data and results from the imaging system to the robotic system. If the robotic system includes a database, the imaging system can contribute image and results to the database. The robotic system, in-turn, may automatically design further experiments based upon the results provided by the imaging system.

According to an embodiment of the present invention, the imaging system 4010 operates in the following manner including a plurality of processes. These processes are merely examples, which should not unduly limit the scope of the claims. One of ordinary skill in the art would recognize many variations, alternatives, and modifications. The microfluidic device 4030 is securely placed on the stage 4020. Based on a fixed feature of the microfluidic device 4030, the computer system 4110 instructs the drive 4025 to move the stage 4020 and align the microfluidic device 4030 with a first fiducial marking. For example, the fiducial marking is embedded within the microfluidic device 4030 at a known z dimension distance from the chamber centerline. In another example, the first fiducial marking comes into focus by the imaging device 4060 based on dead reckoning from the fixed feature. The actual coordinates of the first fiducial marking is then measured and registered with the imaging system 4010. Additionally, the actual coordinates of two or more additional fiducial markings are measured and registered.

The actual locations of the fiducial markings are compared with their design locations in the stored image map respectively. For example, the stored image map is associated with the design space. In another example, the stored image map is an ideal image map. In yet another example, the stored image map is associated with a mathematical grid. Based on the comparison, the imaging system 4010 determines whether stretch, distortion, or other deformation exists in the microfluidic device 4030. If differences are present between the actual fiducial locations and the design fiducial locations, a matrix transformation, such as an Affine transformation, is performed. The transformation converts the actual shape of a metering cell into a virtual shape with respect to the design space. By converting the actual image to the virtual image, an image subtraction and other image analysis may be performed.

Although the above has been shown using a selected sequence of processes for operating the imaging system 4010, there can be many alternatives, modifications, and variations. For example, some of the processes may be expanded and/or combined. Other processes may be inserted to those noted above. Depending upon the embodiment, the specific sequences of steps may be interchanged with others replaced. Further details of these processes are found throughout the present specification.

Figure 15A:
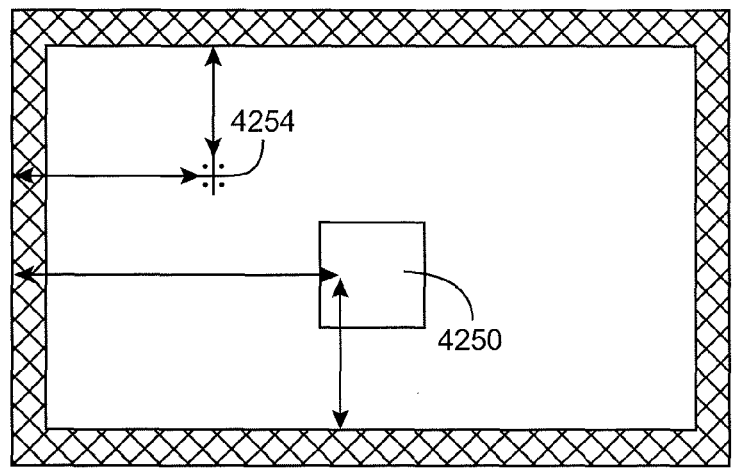
FIGS. 15A and 15B are a simplified microfluidic device according to an embodiment of the present invention.
Figure 15B:
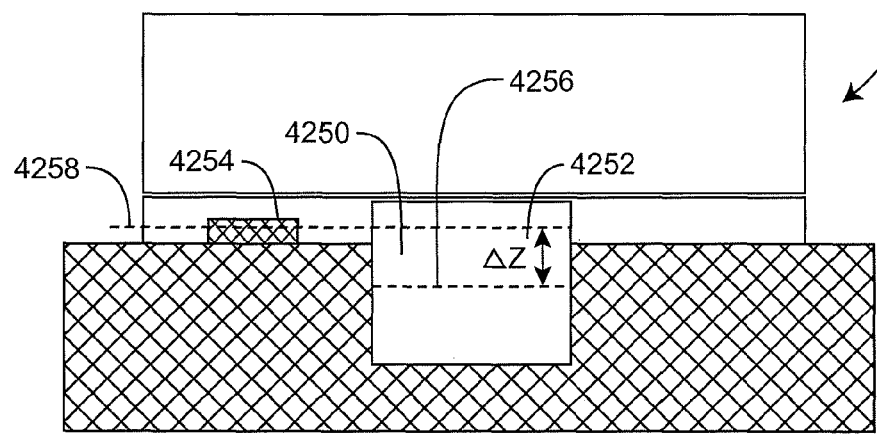

FIGS. 15A and 15B are a simplified microfluidic device according to an embodiment of the present invention. These processes are merely examples, which should not unduly limit the scope of the claims. One of ordinary skill in the art would recognize many variations, alternatives, and modifications. FIGS. 15A and 15B depict a top view and a cross-sectional view of a microfluidic device respectively. A microfluidic device 4230 includes at least a flexible substrate with a chamber 4250 and a fiducial marking 4254. For example, the fiducial markings 4254 are used for xyz alignment and focus of an imaging system. In one embodiment, the imaging system focuses upon the fiducial markings 4254 within the microfluidic device 4230 and conduct mapping between the measurement space and the design space. The imaging system then adjusts a focal plane with respect to the z dimension of the microfluidic device 4230 and places the focal plane in plane with a selected point within the chamber 4250, preferably at chamber focus position 4256. The chamber focus position 4256 is a $\Delta z$ distance 4252 away from a focus plane 4258 of the fiducial markings 4254. For example, at the focus plane 4258, the fiducial markings 4254 are optimally focused. In one embodiment, the microfluidic device 4230 may be used as the microfluidic device 4030. In another embodiment, the microfluidic device may be made by processes described in FIGS. 1-13A.

Figure 16B:
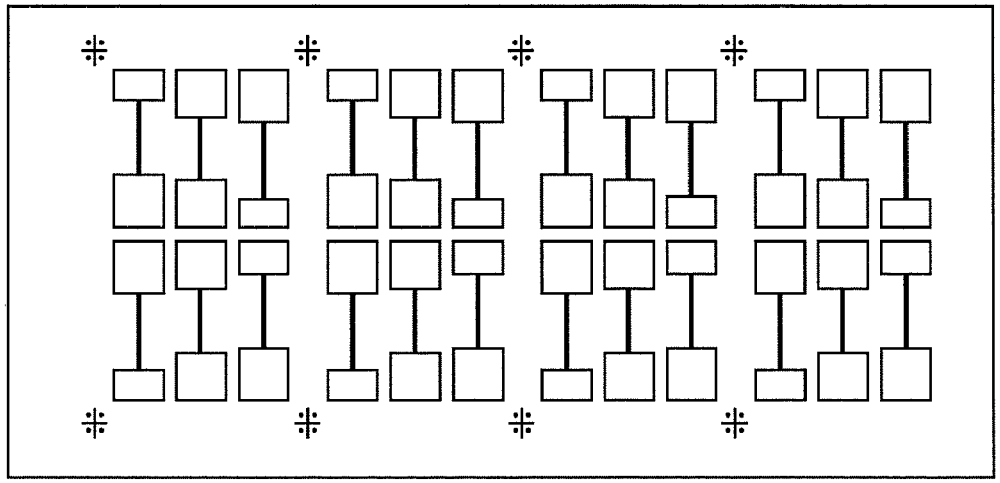
FIGS. 16A and 16B are simplified actual image in measurement space and simplified virtual image in design space respectively according to an embodiment of the present invention.
Figure 16A:
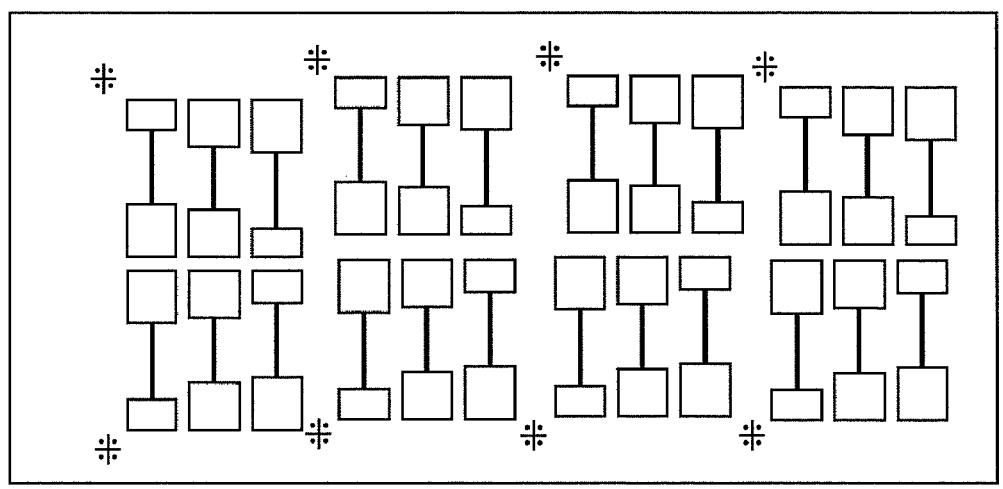

FIGS. 16A and 16B are simplified actual image in measurement space and simplified virtual image in design space respectively according to an embodiment of the present invention. These diagrams are merely examples, which should not unduly limit the scope of the claims. One of ordinary skill in the art would recognize many variations, alternatives, and modifications. For example, the design space is ideal, and the measurement space is distorted.

The difference between the design space and the measurement space can be calculated through fiducial mapping. Consequently, a matrix transformation is developed to convert the actual image into a virtual image in the design space. Transforming various actual images into the same design space facilitates the image subtraction and masking in order to maximize the viewable area of a metering cell chamber. Moreover, if a defect or debris is present within the chamber at time zero in a series of time based images, such defect or debris can be masked out of subsequent images to avoid false positive when applying automated crystal recognition analysis. Additionally, the walls of a chamber may be subtracted from subsequent images to reduce the likelihood of false reading in the crystal recognition analysis.

Figure 17A:
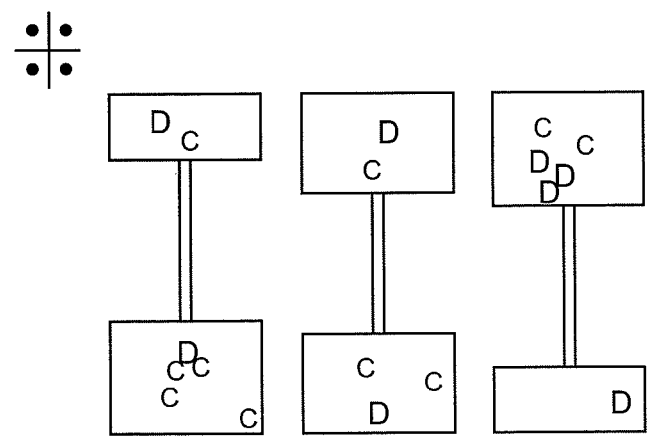
FIGS. 17A, 17B, and 17C show a simplified method for image subtraction and masking according to an embodiment of the present invention.
Figure 17B:
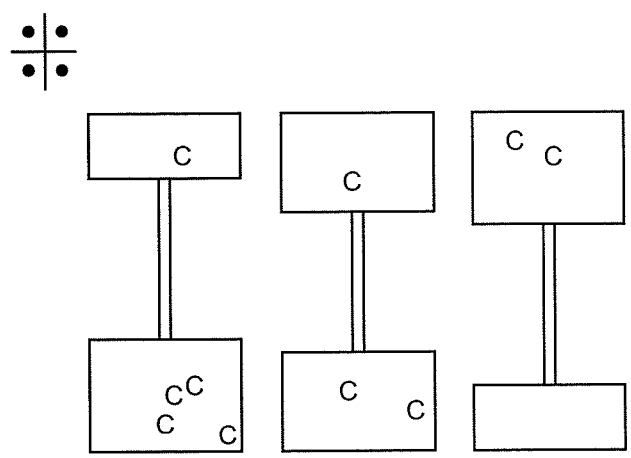
Figure 17C:
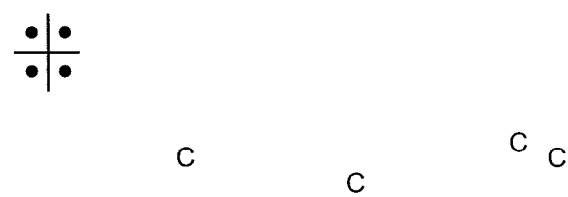

FIGS. 17A, 17B, and 17C show a simplified method for image subtraction and masking according to an embodiment of the present invention. These diagrams are merely examples, which should not unduly limit the scope of the claims. One of ordinary skill in the art would recognize many variations, alternatives, and modifications.

FIG. 17A depicts a metering cell with debris, shown as the letter "D" distributed about the metering cell chambers. The metering cell is transformed into the design space. For example, the metering cell is rotated to align with the design coordinate system and stretch compensated to make the metering cell dimensions match those of the design metering cell dimensions. The foreign objects not present in the design metering cell are masked out such that the regions including and immediately surrounding the foreign objects are masked. The masking can reduce the likelihood of falsely triggering the crystal detection analysis into deeming the foreign objects as crystals that were formed. FIG. 17B depicts a masked image where the foreign objects have been masked.

Additionally, the walls in FIG. 17A can be removed by image subtraction. FIG. 17C depicts an image without chamber walls. From FIG. 17C, further masking may be performed if wall implosion is detected. The wall implosion may occur when the microfluidic device is dehydrating and the chamber contents are permeating outside of the chamber, causing a negative pressure therein and thus wall collapse or implosion. Such further masking for implosion may employ a series of known shapes that occur when chamber implosion occurs and uses such known shapes to create additional masks to occlude from the image the now intruding imploded walls.

Figure 18:
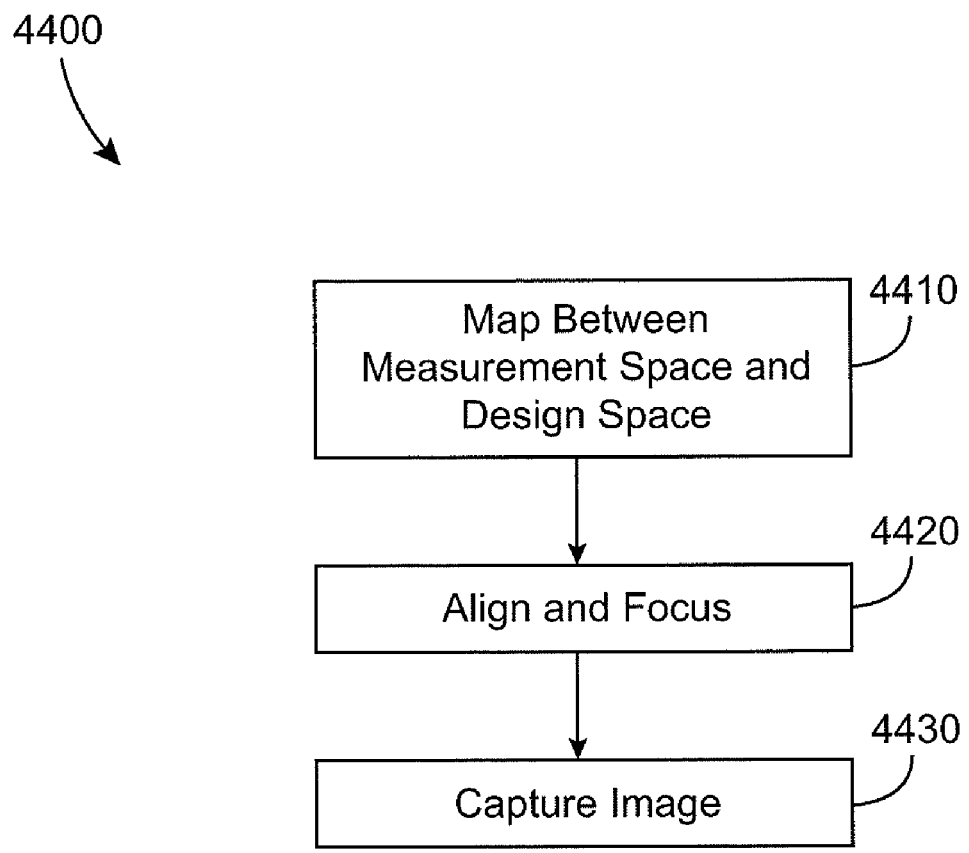
FIG. 18 is a simplified imaging method for microfluidic device according to an embodiment of the present invention.

FIG. 18 is a simplified imaging method for microfluidic device according to an embodiment of the present invention. This diagram is merely an example, which should not unduly limit the scope of the claims. One of ordinary skill in the art would recognize many variations, alternatives, and modifications. The method 4400 includes process 4410 for mapping between measurement space and design space, process 4420 for alignment and focusing, and process 4430 for capturing image. In one embodiment, the method 4400 may be performed by the imaging system 4010 on the microfluidic device 4030. For example, the imaging system 4010 performs the processes 4410, 4420, and 4430 according to the instructions of the computer system 4110 or another computer system. Although the above has been shown using a selected sequence of processes, there can be many alternatives, modifications, and variations. For example, some of the processes may be expanded and/or combined. Other processes may be inserted to those noted above. For example, a process of placing a microfluidic device on the stage of an imaging system is performed prior to the process 4410. Depending upon the embodiment, the specific sequences of processes may be interchanged with others replaced. For example, the process 4420 may be skipped. Further details of these processes are found throughout the present specification and more particularly below.

Figure 19:
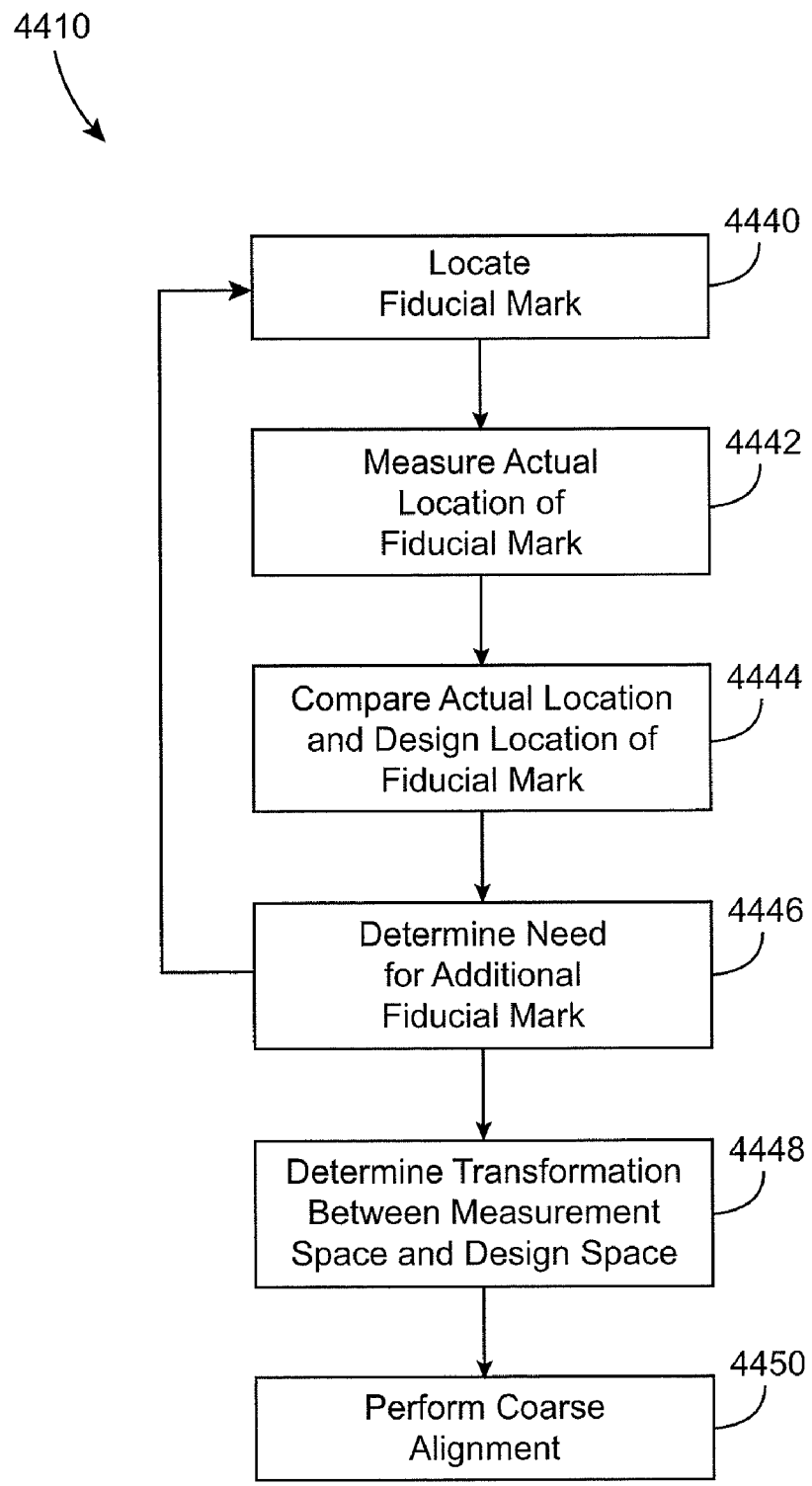
FIG. 19 is a simplified method for mapping between the measurement space and the design space according to an embodiment of the present invention.

At the process 4410, the measurement space and the design space are mapped. FIG. 19 is a simplified process 4410 for mapping between the measurement space and the design space according to an embodiment of the present invention. This diagram is merely an example, which should not unduly limit the scope of the claims. One of ordinary skill in the art would recognize many variations, alternatives, and modifications. The process 4410 includes process 4440 for locating fiducial marking, process 4442 for measuring actual location of fiducial marking, process 4444 for comparing actual location and design location of fiducial marking, process 4446 for determining need for additional fiducial marking, process 4448 for determining transformation between measurement space and design space, and process 4450 for coarse alignment. Although the above has been shown using a selected sequence of processes, there can be many alternatives, modifications, and variations. For example, some of the processes may be expanded and/or combined. Other processes may be inserted to those noted above. Depending upon the embodiment, the specific sequences of processes may be interchanged with others replaced. In one embodiment, the processes 4440, 4442, and 4444 may be performed for more than one fiducial markings before the process 4446 is performed. For example, several fiducial markings are located and measured. In anther embodiment, the process 4444 may be performed after the process 4446 has determined no additional mark needs to located. Further details of these processes are found throughout the present specification and more particularly below.

Figure 20:
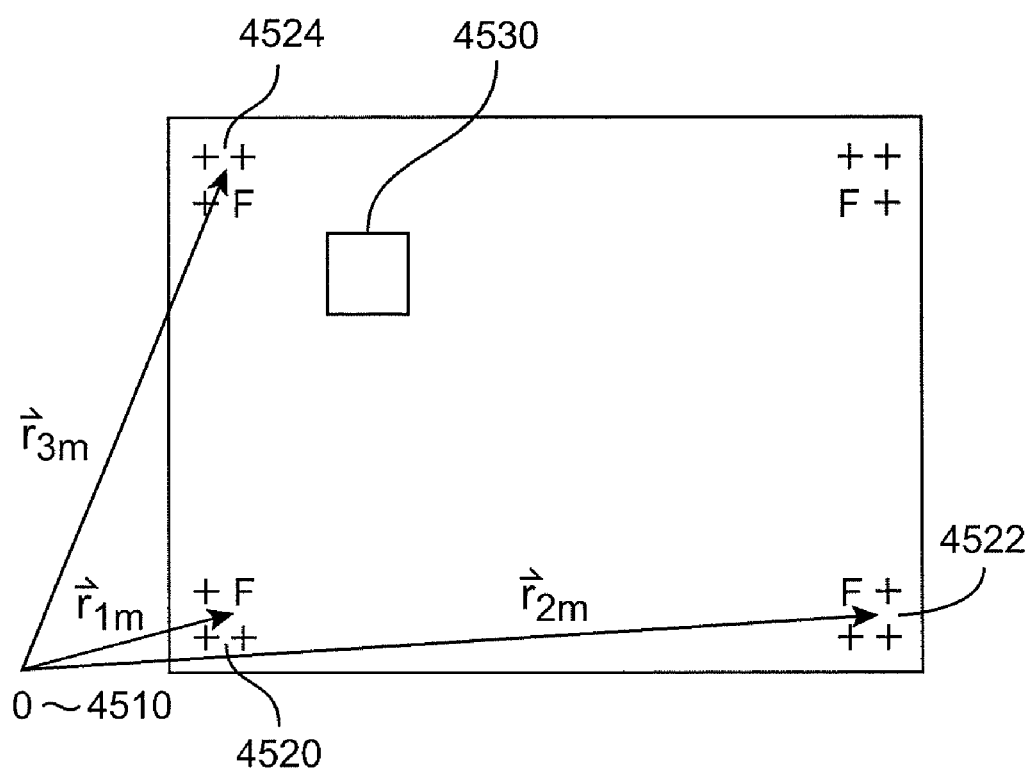
FIG. 20 is a simplified diagram for fiducial markings according to an embodiment of the present invention.

At the process 4440, a fiducial marking is located on a microfluidic device. For example, the microfluidic device is the microfluidic device 4030. FIG. 20 is a simplified diagram for fiducial markings according to an embodiment of the present invention. This diagram is merely an example, which should not unduly limit the scope of the claims. One of ordinary skill in the art would recognize many variations, alternatives, and modifications. As shown in FIG. 20, each of fiducial markings 4520, 4522, and 4524 includes three plus signs or crosses located at three corners of a square and a company logo located at the fourth corner of the square. The fiducial marking 4520, 4522, or 4524 is the fiducial marking located at the process 4440. In one example, the fiducial marking 4520, 4522, or 4524 is a global fiducial. In another example, the fiducial marking 4520, 4522, or 4524 serves as both a global fiducial and a local fiducial. In yet another example, the fiducial marking 4520, 4522, or 4524 is located in the same plane as the well regions of the microfluidic device.

In another embodiment of the present invention, the located fiducial marking has a configuration different from the fiducial marking 4520, 4522, or 4524. In another embodiment, the located fiducial marking is readily recognizable by the image processing algorithm. Operation of the image processing algorithm is improved when the fiducial marking is readily visible, with minimal optical interference from the edge of the microfluidic device or other channels.

Locating the fiducial marking at the process 4440 can be performed manually, automatically, or both. For example, the fiducial marking is moved and identified in the field of view of the imaging system by visual inspection. In another example, the imaging system automatically places and identifies the fiducial marking in the field of view.

Figure 21:
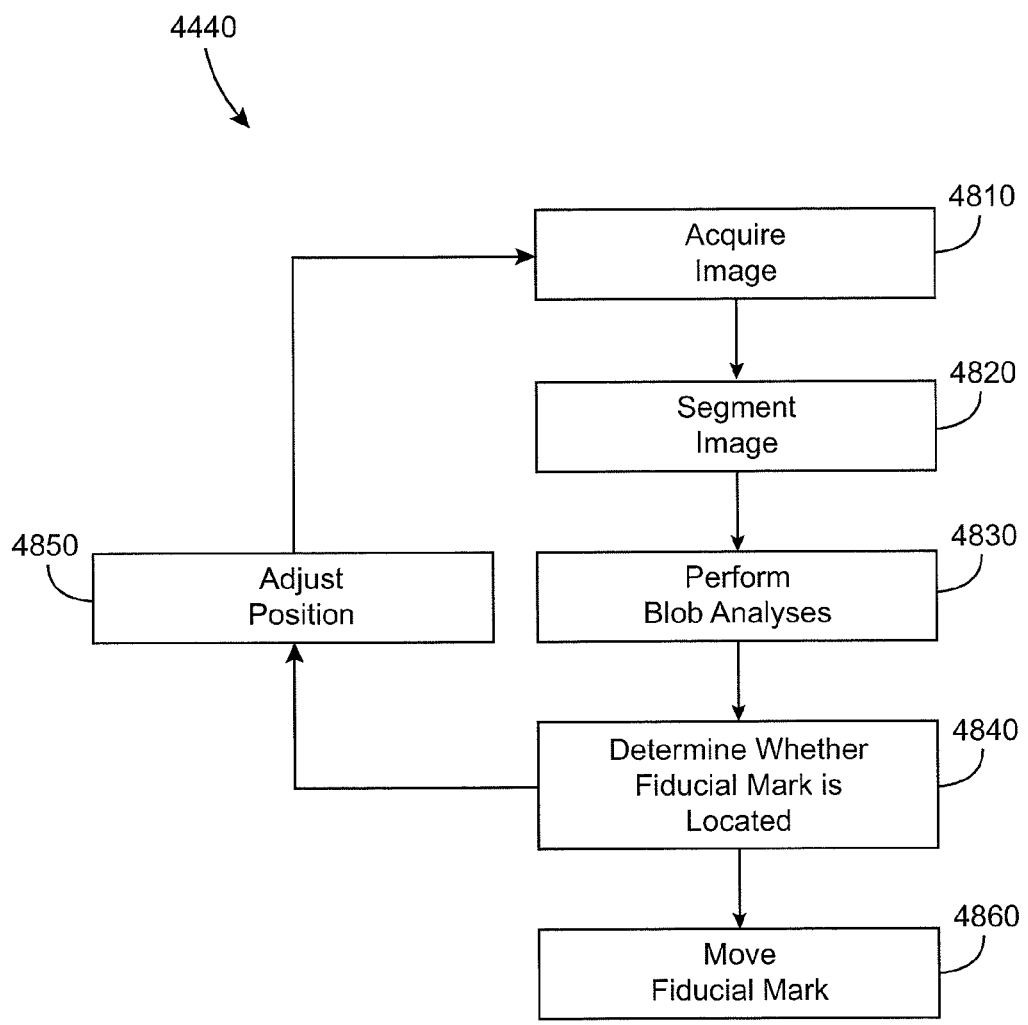
FIG. 21 is a simplified method for locating fiducial marking according to an embodiment of the present invention.

According to an embodiment of the present invention, FIG. 21 is a simplified process 4440 for locating fiducial marking. This diagram is merely an example, which should not unduly limit the scope of the claims. One of ordinary skill in the art would recognize many variations, alternatives, and modifications. The process 4440 includes process 4810 for acquiring image, process 4820 for segmenting image, process 4830 for performing blob analysis, process 4840 for determining whether fiducial marking is located, process 4850 for adjusting position, and process 4860 for moving fiducial marking. Although the above has been shown using a selected sequence of processes, there can be many alternatives, modifications, and variations. For example, some of the processes may be expanded and/or combined. Other processes may be inserted to those noted above. Depending upon the embodiment, the specific sequences of processes may be interchanged with others replaced. For example, the process 4860 may be skipped. Further details of these processes are found throughout the present specification and more particularly below.

At the process 4810, an image of the fiducial marking is acquired. Prior to the process 4810, the stage is positioned to an initial position defined as $\vec{r}_0 = x_0 \hat{x} + y_0 \hat{y} + z_0 \hat{z}$. At the process 4810, an image of the fiducial marking is captures. In one embodiment, the image is captured by a digital camera such as a Leica DC500. In another embodiment, the image has a low resolution. For example, the image is 640×480 pixels in size, and the color depth resolution is 16 bits. In another example, the pixel and color depth resolutions are varied to optimize system performance. After the image is acquired, the image may be adjusted to compensate for variations in lamp intensity and color. This compensation may take the form of image normalization. Additionally, the red, blue, and green components of the image can be adjusted to white balance the image. The white-balancing of the image may be accomplished by median correction or other known techniques.

At the process 4820, the image is segmented. Segmentation of the image can separate desired images from the background signal and produce "blobs" useful in further analysis steps. At the process 4830, the blob analysis is performed. The blobs in the image are compared against a training set contained in a database. The training set contains images of a fiducial marking obtained from a large number of microfluidic devices and imaging conditions. For example, the fiducial marking is the company logo. In another example, the fiducial marking is one other than the company logo.

At the process 4840, whether the fiducial marking is located is determined. If the fiducial marking is located, the process 4442 is performed. In one embodiment, if the best match of the blobs to the standards is found to be within a predetermined specification, the fiducial marking is considered to be located. For example, the predetermined specification includes a proximity ranking of less than 4200. If the fiducial marking is not detected, the process 4850 is performed.

At the process 4850, the position of the stage is adjusted. After the adjustment, the processes 4810, 4820, 4830 and 4840 are performed. In one embodiment, at the process 4850, the stage is moved in an x direction and/or a y direction. In another embodiment, the stage is moved in a z direction at the process 4850. For example, the stage is moved by a selected amount in a first z-direction ($\Delta z$) by stepping the z-motor of the stage in a first selected direction. At each stepped z-height, the processes 4810, 4820, 4830 and 4840 are performed. The process 4850 is repeated until the fiducial marking is determined to be located at the process 4840 or the stage reaches the end of its range of motion in the first z direction. If the stage reaches the end of its range of motion, the stage is returned to the initial position, $\vec{r}_0$, and the stage is stepped by $\Delta z$ in a second selected z-direction. For example, the second z-direction is opposite to the first z-direction. The step size $\Delta z$ can be uniform in both directions, or vary as a function of direction or distance from $\vec{r}_0$. At each stepped z-height in the second direction, the processes 4810, 4820, 4830, and 4840 are performed. The process 4850 is repeated until the fiducial marking is located or the stage reaches the end of its range of motion in the second z direction. If the fiducial marking cannot be located within the range of motion, an error message is generated. In yet another embodiment, at the process 4850, the stage is moved in an x direction, a y direction, and/or a z direction.

At the process 4860, the stage is translated to move the fiducial marking to substantially the center of the field of view of the imaging system.

As shown in FIG. 19, at the process 4442, the actual location of the located fiducial marking is measured. As shown in FIG. 20, the measured location of the fiducial marking 4520 is represented by vector $\vec{r}_{1m}$ with respect to the origin O 4510. The measured vector $\vec{r}_{nm}$ representing the actual location of a fiducial marking can also be written as:

$$\vec{r}_{nm} = \begin{bmatrix} x_{nm} \\ y_{nm} \\ z_{nm} \end{bmatrix} \quad \text{(Equation 1)}$$

where n is a positive integer. For example, the actual location $\vec{r}_{nm}$ is automatically detected by an image processing routine.

At the process 4444, the actual location and the design location of the fiducial marking is compared. The design location of the fiducial marking 4520, referenced to an origin O, can be represented by a design vector $\vec{r}_{1D}$. The design vector $\vec{r}_{nD}$ representing the design location of a fiducial marking can also be written as:

$$\vec{r}_{nD} = \begin{bmatrix} x_{nD} \\ y_{nD} \\ z_{nD} \end{bmatrix} \quad \text{(Equation 2)}$$

where n is a positive integer. The difference in the design location $\vec{r}_{nD}$ and the measured location $\vec{r}_{nm}$ can be calculated as $\vec{r}_{nO} = \vec{r}_{nD} - \vec{r}_{nm}$.

As discussed above and further emphasized here, the processes 4440, 4442, and 4444 are only examples. One of ordinary skill in the art would recognize many variations, alternatives, and modifications. In one embodiment, at the processes 4440, 4442, and 4444, the imaging system uses a predetermined magnification objective. For example, a 10× magnification objective is used for the lenses 4075 of the imaging system 4010.

In another embodiment, the imaging system first uses a lower power magnification objective, such as a 2.5× magnification objective, at the processes 4440, 4442, and 4446. Subsequently, for the same fiducial marking, the coarse alignment of the microfluidic device is performed. For example, the coarse alignment uses the difference vector $\vec{r}_{nO}$. The vector $\vec{r}_{nO}$ represents the translation of the located fiducial marking in the x, y, and z axes from the design location. Using the x and y scalar values from $\vec{r}_{nO}$, the stage position of the imaging system can be adjusted in the x-y plane to position the located fiducial marking at a predetermined location in the x-y plane. Additionally, using the z-axis scalar value from $\vec{r}_{nO}$, the position of the stage can be adjusted in the z plane to position the fiducial marking at a selected location in the z plane. The z-axis focus adjustment may be performed before, after, and/or at the same time as the adjustment in the x-y plane.

Afterwards, the imaging system switches to a higher power magnification objective, for example, a 10× magnification objective. For example, the measurements and adjustments made with a lower power objective place the fiducial marking within the field of view of the imaging objective when the objective is switched to the higher power magnification objective. With the higher power magnification objective, the image system can more accurately determine the vectors $\vec{r}_{nm}$ and $\vec{r}_{nO}$.

At the process 4446, whether an additional fiducial marking should be located and measured is determined. If an additional fiducial marking does not need to be located and measured, the process 4448 is performed. If an additional fiducial marking should be located and measured, the process 4440 is performed.

For example, the processes 4440, 4442, and 4444 are performed for each of the three fiducial markings 4520, 4522, and 4524 as shown in FIG. 20. For the fiducial marking 4520, $\vec{r}_{1m}$ and $\vec{r}_{10}$ are determined. For the fiducial marking 4522, $\vec{r}_{2m}$ and $\vec{r}_{20}$ are determined. For the fiducial marking 4524, $\vec{r}_{3m}$ and $\vec{r}_{30}$ are determined. In other embodiments, more than three global fiducial markings are located and measured.

At the process 4448, the transformation between measurement space and design space is determined. For example, a matrix transformation, such as an Affine transformation, is determined based on the difference vectors $\vec{r}_{nO}$.

In one embodiment of the present invention, using a flexible microfluidic device, non-uniform absorption of fluids, non-uniform hydration and dehydration, or other factors, can result in flexing, stretching, shrinking, bowing, swelling, contracting and other distortions in the microfluidic device. In addition, fabrication processes for the device, handling during packaging and testing, and other protocols can introduce deformations and distortions in the device. These deformations may be dimensionally uniform or non-uniform, including both linear and non-linear distortions. The effects of these distortions may impact the magnitude and direction of the measured vectors $\vec{r}_{nm}$. Accordingly, the deviation of these measured vectors from their corresponding design vectors $\vec{r}_{nD}$ represent the linear and non-linear distortions of the microfluidic device media. Using the difference vectors $\vec{r}_{n\delta}$, a transformation can be created between the design space and the measurement space. This transformation is correlated with the flexing, stretching, bowing, and other distortions and deformations present in the microfluidic device. The transformation may have linear components and/or non-linear components.

For example, a transformation is determined based on three fiducial markings, such as the fiducial markings 4520, 4522, and 4524. Such transformation can provide a planar mapping of the microfluidic device. The plane defined by the three fiducial markings can be used to characterize the translation of the microfluidic device in the three dimensions of x, y, and z as well as stretching of the microfluidic device material in the plane of the microfluidic device. The roll, pitch, and yaw of this plane can also be characterized by the plane defined by the three fiducial markings.

At the process 4450, the coarse alignment is performed with the transformation between the design space and the measurement space. For example, the actual position of a metering cell of the microfluidic device is determined, and the metering cell is positioned in preparation for imaging. For example, the actual location of a metering cell can be shifted from the design location due to distortions and deformations of the microfluidic device. Not only can the plane of the microfluidic device be translated and tilted, the microfluidic device can be stretched in the plane of the microfluidic device, further shifting the actual position of the metering cell. In one embodiment, the metering cell is shifted in the x dimension and/or the y dimension. In another embodiment, the metering cell is shifted in the z dimension.

Figure 22:
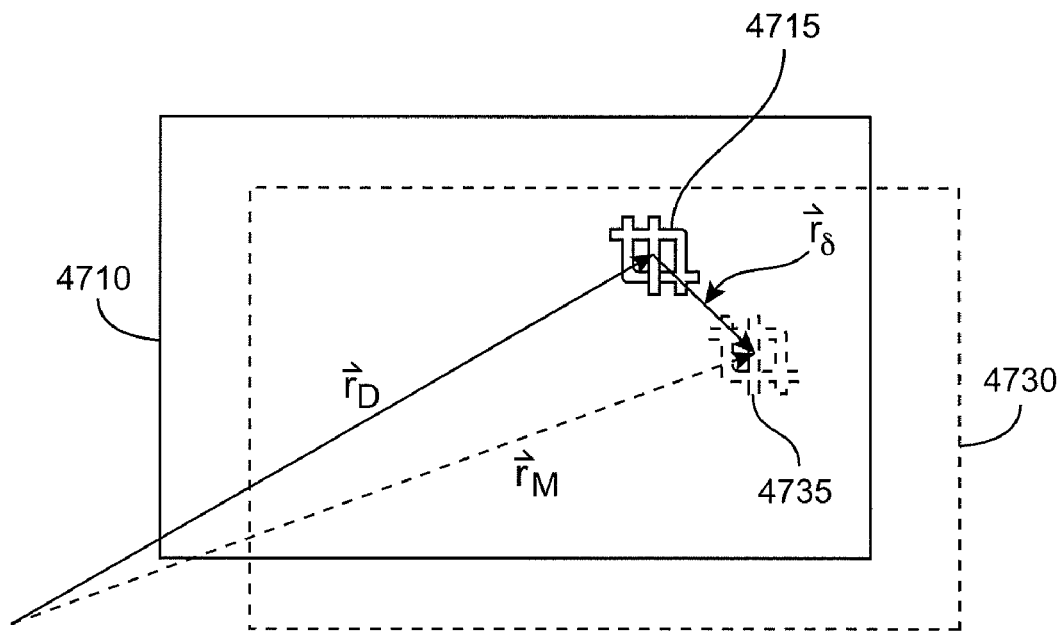
FIG. 22 is a simplified metering cell shifted from design position according to an embodiment of the present invention.

FIG. 22 is a simplified metering cell shifted from design position according to an embodiment of the present invention. This diagram is merely an example, which should not unduly limit the scope of the claims herein. One of ordinary skill in the art would recognize many variations, modifications, and alternatives. In FIG. 22, a metering cell 4710 in the design space is schematically illustrated with solid lines and the same metering cell 4730 in the measurement space is schematically illustrated in dashed lines. The design vector $\vec{r}_D$ points to a design location 4715 of a fiducial marking of the metering cell 4710, and the measured vector $\vec{r}_M$ points to a design location 4735 of the same fiducial marking of the same metering cell 4730. The tip of the measured vector $\vec{r}_M$ is offset from the design vector $\vec{r}_D$ by an error vector $\vec{r}_\delta$. This error vector can have components in all three dimensions. Using the transformation from design space to measurement space, the approximate actual location of a metering cell can be calculated by taking into account the error vector. The stage of the imaging system can be moved in the x dimension, the y dimension, and/or the z dimension to position the metering cell in preparation for imaging.

As discussed above, FIG. 19 is merely an example, which should not unduly limit the scope of the claims. One of ordinary skill in the art would recognize many variations, alternatives, and modifications. For example, to initiate the microfluidic device registration process, an algorithm can be used to register the microfluidic device with respect to the coordinates of the imaging system coupled to camera and the stage. Based on determinations and/or evaluations of the stack-up tolerances from the integrated microfluidic device and carrier and the microscope stage, tolerance metrics can be set. In one embodiment, the tolerances is set to ensure that at least one global fiducial generally appears within the field of view available when the lenses 4075 comprise a 2.5× objective. This tolerance definition allows automation of the fiducial finding process and streamline system operation. In another embodiment, an automated system can locate a fiducial marking outside the current field of view of the imaging system through a search routine. Additionally, the movement of the fiducial mark can be performed, for example, by moving the stage with respect to the imaging device, moving the imaging device with respect to the stage, or both. The stage carries the microfluidic device to which the fiducial mark belongs.

Figure 23:
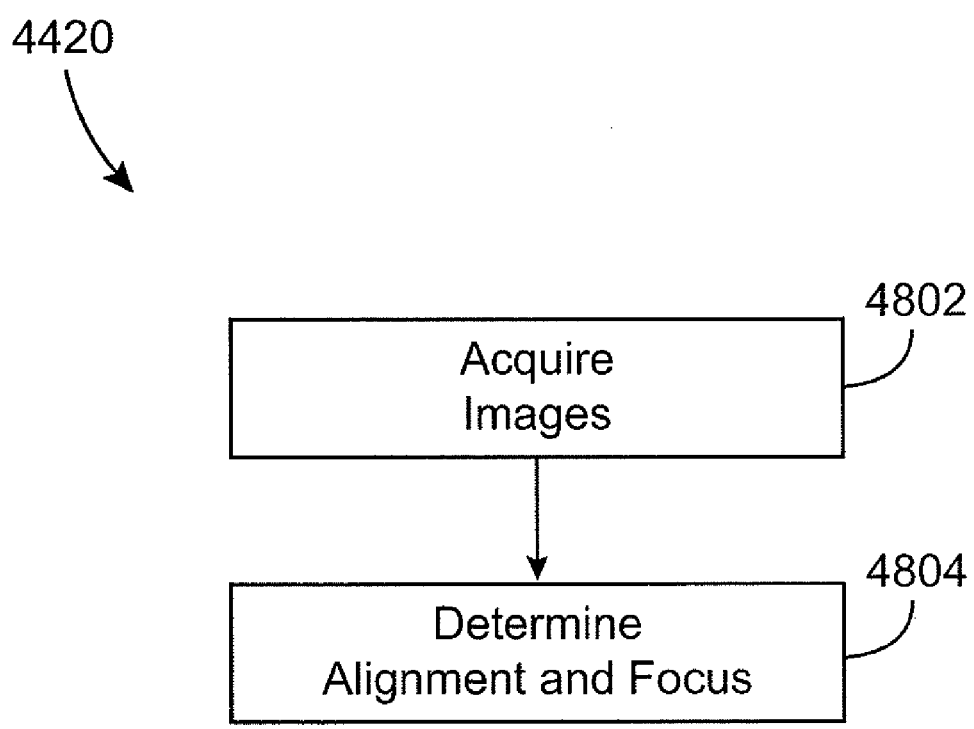
FIG. 23 is a simplified method for aligning and focusing image system according to an embodiment of the present invention.

As shown in FIG. 18, at the process 4420, the alignment and focusing are performed. FIG. 23 is a simplified process 4420 for aligning and focusing image system according to an embodiment of the present invention. This diagram is merely an example, which should not unduly limit the scope of the claims. One of ordinary skill in the art would recognize many variations, alternatives, and modifications. The process 4420 includes process 4802 for acquiring images of and process 4804 for determining alignment and focus. Although the above has been shown using a selected sequence of processes, there can be many alternatives, modifications, and variations. For example, some of the processes may be expanded and/or combined. Other processes may be inserted to those noted above. For example, a process substantially similar to the process 4440 as described in FIG. 21 is performed on a metering cell and its associated fiducial marking, which are aligned, focused and imaged at the processes 4802 and 4804. Depending upon the embodiment, the specific sequences of processes may be interchanged with others replaced. Further details of these processes are found throughout the present specification and more particularly below.

Figure 24:
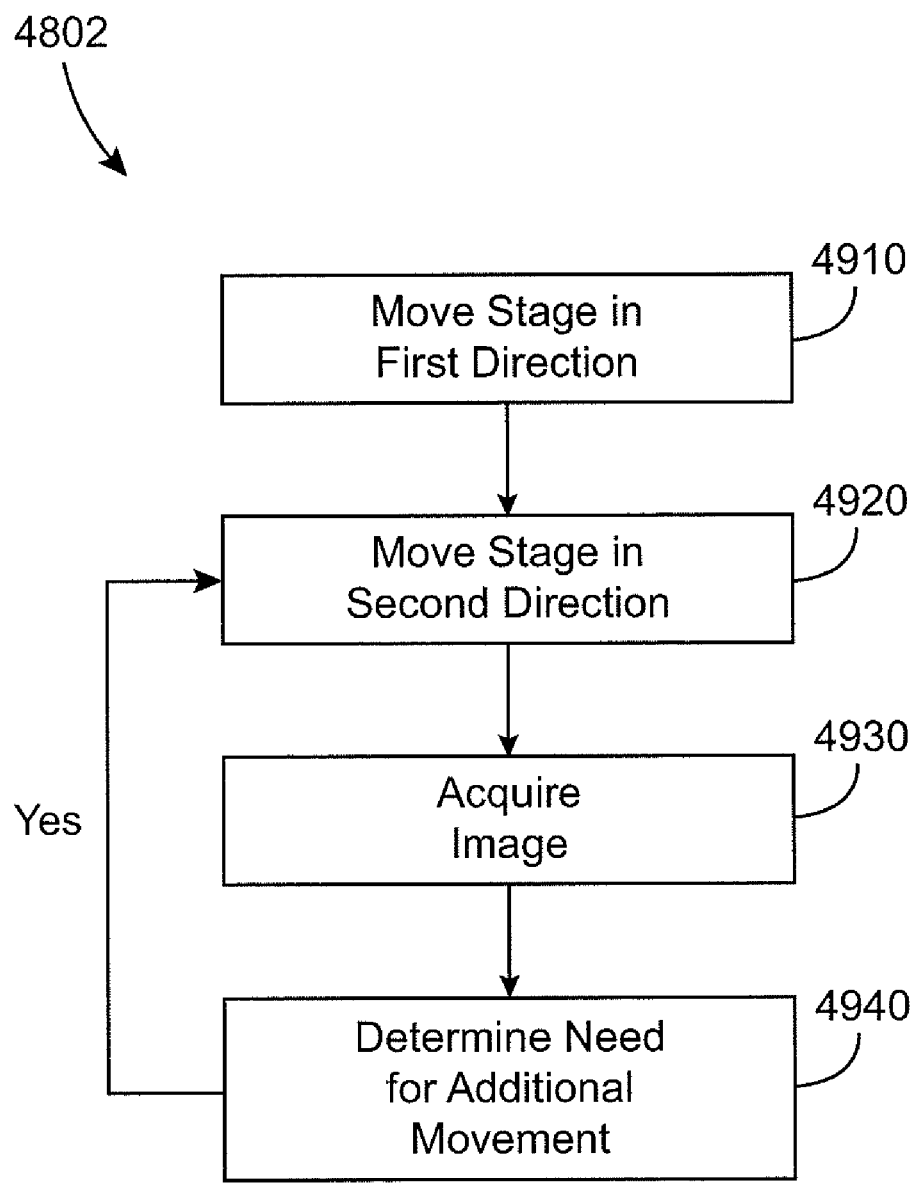
FIG. 24 is a simplified method for acquiring images of fiducial marking according to an embodiment of the present invention.

At the process 4802, images of a fiducial marking is acquired For example, the fiducial marking is associated with the metering cell, which has been aligned using the mapping between the design space and the measurement space at the process 4450. FIG. 24 is a simplified process 4802 for acquiring images of fiducial marking according to an embodiment of the present invention. This diagram is merely an example, which should not unduly limit the scope of the claims. One of ordinary skill in the art would recognize many variations, alternatives, and modifications. The process 4802 includes process 4910 for moving stage in first direction, process 4920 for moving stage in second direction, process 4930 for acquire image, and process 4940 for determining need for additional movement. Although the above has been shown using a selected sequence of processes, there can be many alternatives, modifications, and variations. For example, some of the processes may be expanded and/or combined. Other processes may be inserted to those noted above. Depending upon the embodiment, the specific sequences of processes may be interchanged with others replaced. For example, the fiducial marking used in the process 4802 may be a company logo having a height the same as that of the wells. In another example, the fiducial marking has a height different from that of the wells. The known offset between the plane of the fiducial marking and that of the wells would enable accurate z-axis adjustments to be made. Further details of these processes are found throughout the present specification and more particularly below.

At the process 4910, the stage of the imaging system is moved in a first z direction. As discussed above, at the process 4450, the metering cell and its associated fiducial marking can be aligned in the x dimension, the y dimension, and/or the z dimension based on the transformation between the design space and the measurement space. At the end of process 4450, the z position of the stage is referred to as $z_f$. At the process 4910, the stage is moved from $z_f$ by a distance in a first z-direction equal to $z_1 + \delta z$.

At the process 4920, the stage is moved in a second z-direction by a distance equal to $\delta z$. For example, this second z direction is opposite to the first z direction. The step size $\delta z$ can be uniform or vary as a function of distance from $z_f$.

At the process 4930, an image of the fiducial marking is acquired. In one embodiment, the image is captured by a digital camera such as a Leica DC500. In another embodiment, the image has a low resolution. For example, the image is 640×480 pixels in size, and the color depth resolution is 16 bits. In another example, the pixel and color depth resolutions are varied to optimize system performance. After the image is acquired, the image may be adjusted to compensate for variations in lamp intensity and color. This compensation may take the form of image normalization. Additionally, the red, blue, and green components of the image can be adjusted to white balance the image. The white-balancing of the image may be accomplished by median correction or other known techniques.

At the process 4940, whether additional stage movement should be performed is determined. If the stage has been moved in the second direction though a distance equal to or larger than $2 \cdot z_1 + \delta z$, no additional stage movement is needed. The process 4804 should be performed. If the stage has been moved in the second direction though a distance smaller than $2 \cdot z_1 + \delta z$, an additional stage movement is needed. The process 4920 is performed.

Figure 25:
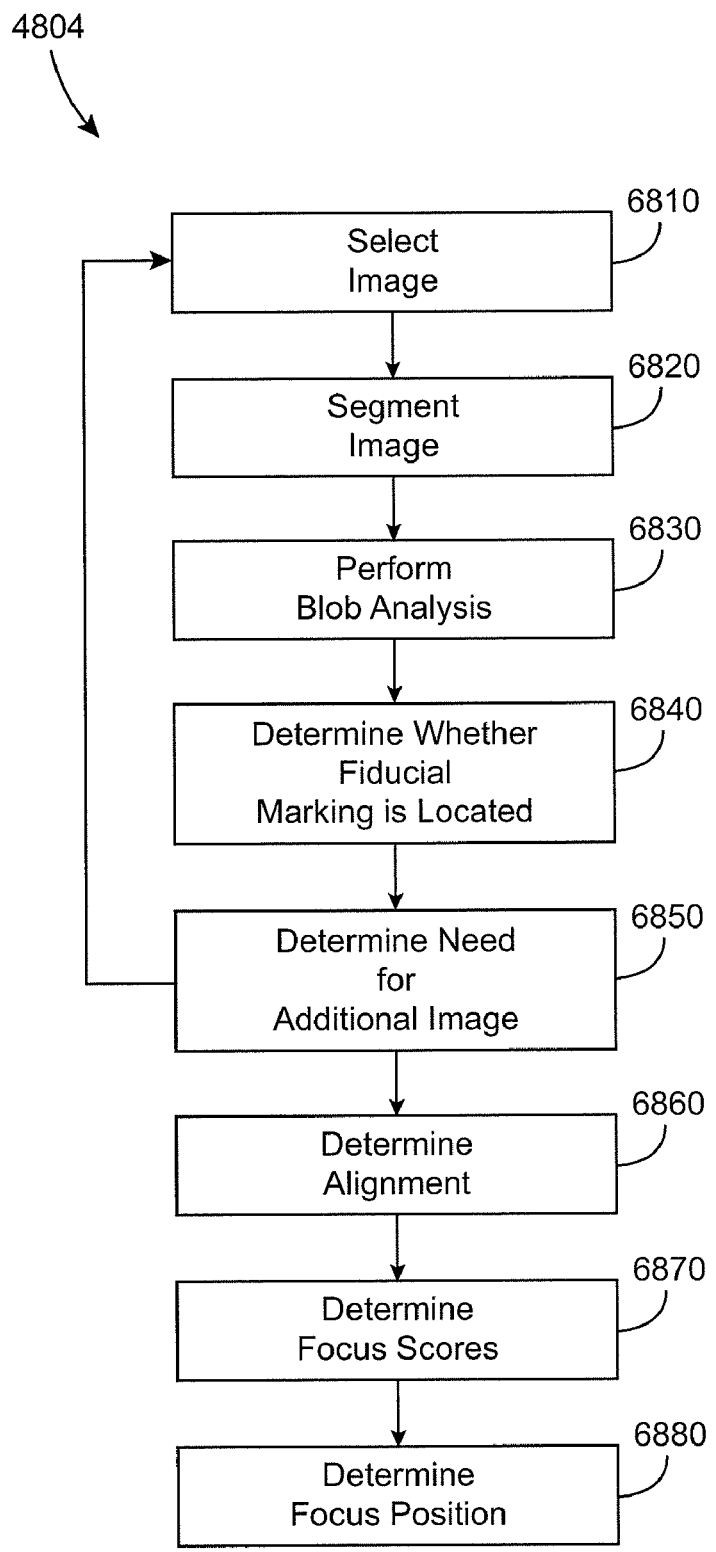
FIG. 25 is a simplified method for aligning and focusing image system according to an embodiment of the present invention.

As shown in FIG. 23, at the process 4804, the alignment and focus are determined. FIG. 25 is a simplified process 4804 for aligning and focusing image system according to an embodiment of the present invention. This diagram is merely an example, which should not unduly limit the scope of the claims. One of ordinary skill in the art would recognize many variations, alternatives, and modifications. The process 4804 includes 6810 for selecting image, process 6820 for segmenting image, process 6830 for performing blob analysis, process 6840 for determining whether fiducial marking is located, process 6850 for determining need for additional image, process 6860 for determining alignment, process 6870 for determining focus scores, and process 6880 for determining focus position. Although the above has been shown using a selected sequence of processes, there can be many alternatives, modifications, and variations. For example, some of the processes may be expanded and/or combined. Other processes may be inserted to those noted above. Depending upon the embodiment, the specific sequences of processes may be interchanged with others replaced. For example, the process 6860 is skipped. In another example, the process 6860 is performed after the process 6880. Further details of these processes are found throughout the present specification and more particularly below.

At the process 6810, an image is selected from the images taken in the process 4802 for further analysis. At the process 6820, the selected image is segmented. Segmentation of the image can separate desired image from the background signal and produce "blobs" useful in further analysis steps.

At the process 6830, the blob analysis is performed. The blobs in the image are compared against a training set contained in a database. The training set contains images of a fiducial marking obtained from a large number of microfluidic devices and imaging conditions. For example, the fiducial marking is the company logo. In another example, the fiducial marking is one other than the company logo.

Figure 26:
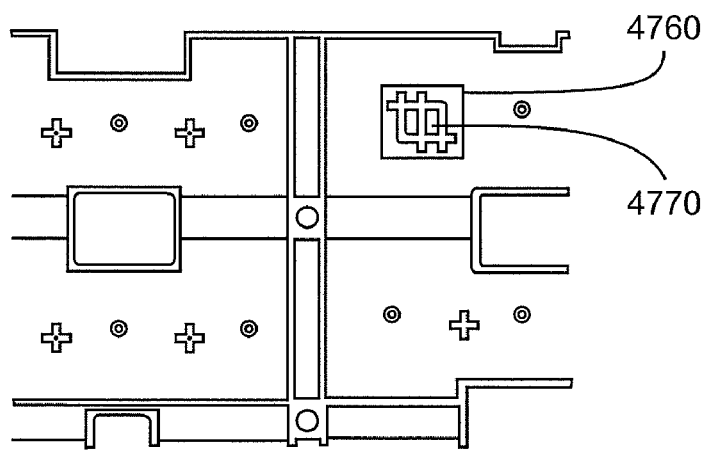
FIG. 26 is a simplified image acquired and analyzed according to an embodiment of the present invention.

At the process 6840, whether the fiducial marking is located is determined. If the fiducial marking is located, a region of interest (ROI) is created around the fiducial marking FIG. 26 is a simplified image acquired and analyzed according to an embodiment of the present invention. This diagram is merely an example, which should not unduly limit the scope of the claims. One of ordinary skill in the art would recognize many variations, alternatives, and modifications. The fiducial marking may be a company log 4770 surround by a region of interest 4760. In one embodiment, if the best match of the blobs to the standards is found to be within a predetermined specification, the fiducial marking is considered to be located. For example, the predetermined specification includes a proximity ranking of less than 4200.

At the process 6850, whether additional image should be analyzed is determined. For example, if any of the images taken at the process 4802 has not been selected at the process 6810, the process 6810 is performed to select the image not yet selected. If all of the images taken at the process 4802 have been selected, the process 6860 is performed.

At the process 6860, the alignment in the x and y dimensions is determined. In one embodiment, the alignment uses the actual location of an ROI and the design location of the ROI. For example, the alignment in the x and y dimensions are determined by the difference between the actual location and the design location. In another embodiment, the fiducial marking has a known spatial relationship with chambers within the metering cell in the x and y dimensions. The alignment in the x and y dimensions of the metering cell is determined based on the alignment in the x and y dimensions of the fiducial marking. For example, the metering cell has a length and a width each about 2 μm. The fiducial marking is placed substantially at the center of the metering cell. In another example, the fiducial marking is in the vicinity of or within the metering cell and their actual spatial relationship in the x and y dimensions does not change significantly from the design spatial relationship.

At the process 6870, a focus score is determined and stored. In one embodiment, the focus score is calculated based on the standard deviation. In another embodiment, the focus score is calculated based on the "edginess" of the image. For example, the "edginess" of the image is assessed by a sobel operator. In another example, the "edginess" of the image is determined by an edge-sensitive computer program similar to a high pass filter. The techniques based on the "edginess" of the image usually take into account that when the image is in sharp focus, high frequency details are visible, and when the image is out of focus, the high frequency details are blurred or smudged. In yet another embodiment, the focus score is calculated based on histogram. The histogram techniques use specific characteristics of the fiducial marking to improve focusing.

In yet another embodiment of the present invention, the images for the area of interest are acquired by the imaging system. For each of at least some of the acquired images, a first sobel square sum is determined. The sobel operator is applied to each data point on the acquired image. Each resultant value is squared, and all of the squared values are added together. Additionally, the acquired image is blurred. For example, the blurring may be accomplished by applying Gaussian smoothing to the acquired image. In one embodiment, the Gaussian smoothing serves as a low pass filter attenuating high frequency components of the acquired image. In another embodiment, the Gaussian smoothing can be described as follows:

For the blurred image, a second sobel square sum is determined by applying the sobel operator to the blurred image, squaring each resultant value, and summing all the squared values. Afterwards, clipping is applied to the second sobel square sum. If the second sobel square is smaller than a predetermined threshold, the second sobel square sum is set to the predetermined threshold. Dividing the clipped second sobel square sum by the first sobel square sum, the resultant ratio is used as the focus score. The focus score for each of at least some of the acquired images is then stored.

At the process 6880, the focus position for the metering cell is determined. As discussed above, at the process 6870, the focus scores are obtained for various z positions. At the process 6880, in one embodiment, the z position corresponding to a peak focus score is used as the focus position. In another embodiment, the z positions corresponding to two peak focus scores are determined and averaged. The average z position is used as the focus position. In yet another embodiment, the focus position is determined based on the characteristic of the entire curve representing the focus score as a function of z position.

In another embodiment, the fiducial marking has a known spatial relationship with chambers within the metering cell in the z dimension. The focus position in the z dimension of the metering cell is determined based on the focus position in the z dimension of the fiducial marking. For example, the metering cell has a length and a width each about 2 µm. The fiducial marking is placed substantially at the center of the metering cell. In another example, the fiducial marking is in the vicinity of or within the metering cell and their actual spatial relationship in the z dimension does not change significantly from the design spatial relationship.

Figure 27:
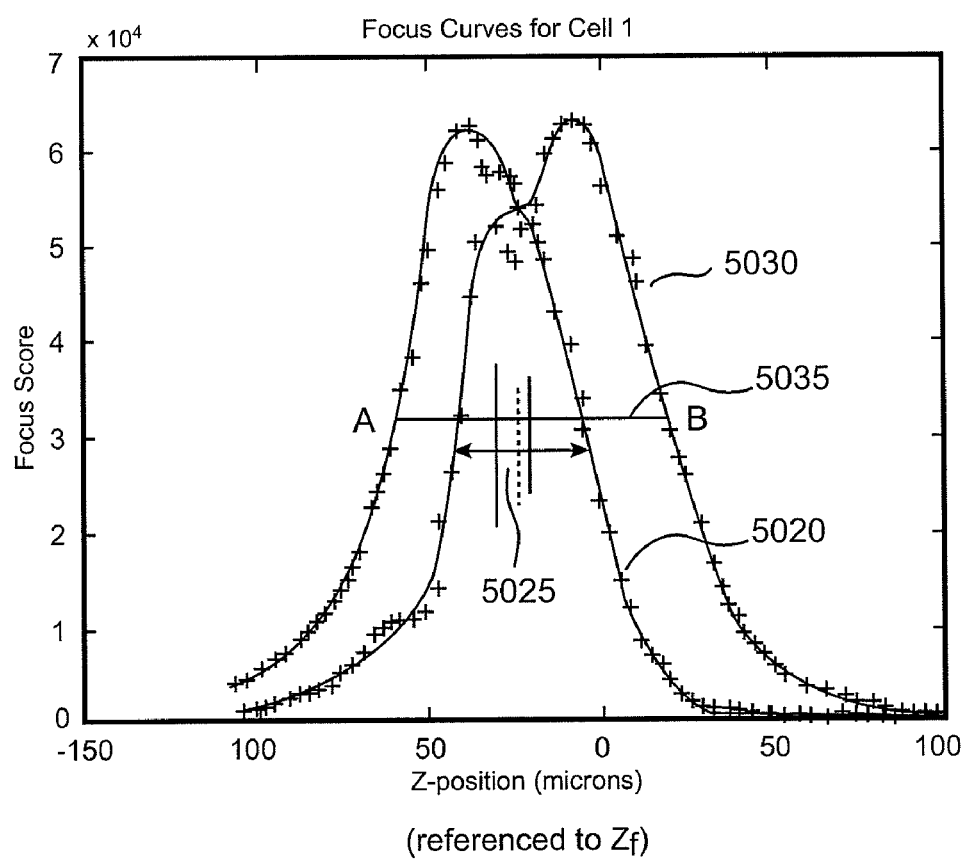
FIG. 27 shows simplified curves for focus score as a function of z position obtained at the process 804 according to an embodiment of the present invention.

FIG. 27 shows simplified curves for focus score as a function of z position obtained at the process 6870 according to an embodiment of the present invention. The focus score at each z value is associated with the sobel square sum for the acquired image without blurring. This diagram is merely an example, which should not unduly limit the scope of the claims. One of ordinary skill in the art would recognize many variations, alternatives, and modifications. As shown in FIG. 27, focus scores are calculated at z-axis positions separated by approximately 2 µm and extending for 100 µm on either side of $z_f$. The coarse nature of the z-axis position determined by the process 4802 is evident, as the peak of the focus score distributions are located approximately 20 µm from $z_f$.

In another embodiment, the method by which the stage is scanned, the density of measurement points, and the range over which the measurements extend can be varied, as would be evident to those skilled in the art. For example, focus scores are collected at fewer locations separated by greater distances. In another example, focus scores collected at 10 µm spacing located on alternating sides of $z_f$ is used as inputs to the image processing software, only obtaining additional focus scores and filling in the curve if needed.

FIG. 27 shows two different focus score runs in which the aperture of the condenser of the imaging system is operated in either a narrow or a wide setting. A curve 5030 corresponds to a narrow setting and represents a bi-modal distribution of focus scores. The twin peaks are each associated with the detection of the top and bottom edges of the fiducial marking, such as a company logo. This bi-modal distribution can be characterized by a full width half magnitude (FWHM) 5035. If the condenser aperture is operated at a wide setting, the bi-modal distribution merges into a single peaked distribution represented by a curve 5020. The amplitude of the single peak is reduced from the amplitude characteristic of the bi-modal distribution and the FWHM is reduced as well. The FWHM of the single peak distribution is represented by line 5025.

Figure 28:
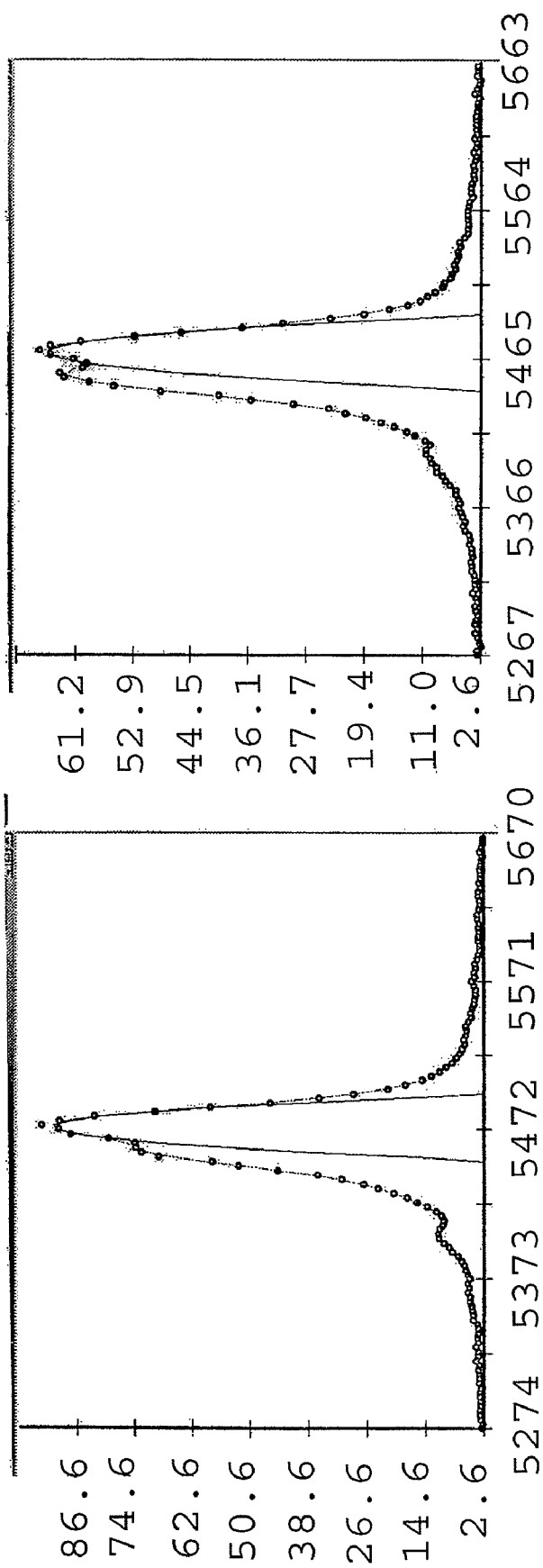
FIG. 28 shows simplified curves for focus score as a function of z position according to one embodiment of the present invention.

Additionally, FIG. 28 shows simplified curves for focus score as a function of z position obtained at the process 4804 according to one embodiment of the present invention. The focus score at each z value is associated with the sobel square sum for the acquired image without blurring. This diagram is merely an example, which should not unduly limit the scope of the claims. One of ordinary skill in the art would recognize many variations, alternatives, and modifications. As shown in FIGS. 27 and 28, the focusing scores obtained without image blurring may produce irregular focal peaks under certain conditions. Sometimes the peak is single modal, sometimes the peak is bi-modal, and usually the peak is a combination of the two. Neither peak is guaranteed to be the top peak and thus grabbing one peak over the other may result in a focus plane error on the order of tens of microns. If the depth of field of the imaging system is less than 10 microns, grabbing the wrong peak can produce significantly out of focus images.

Figure 29:
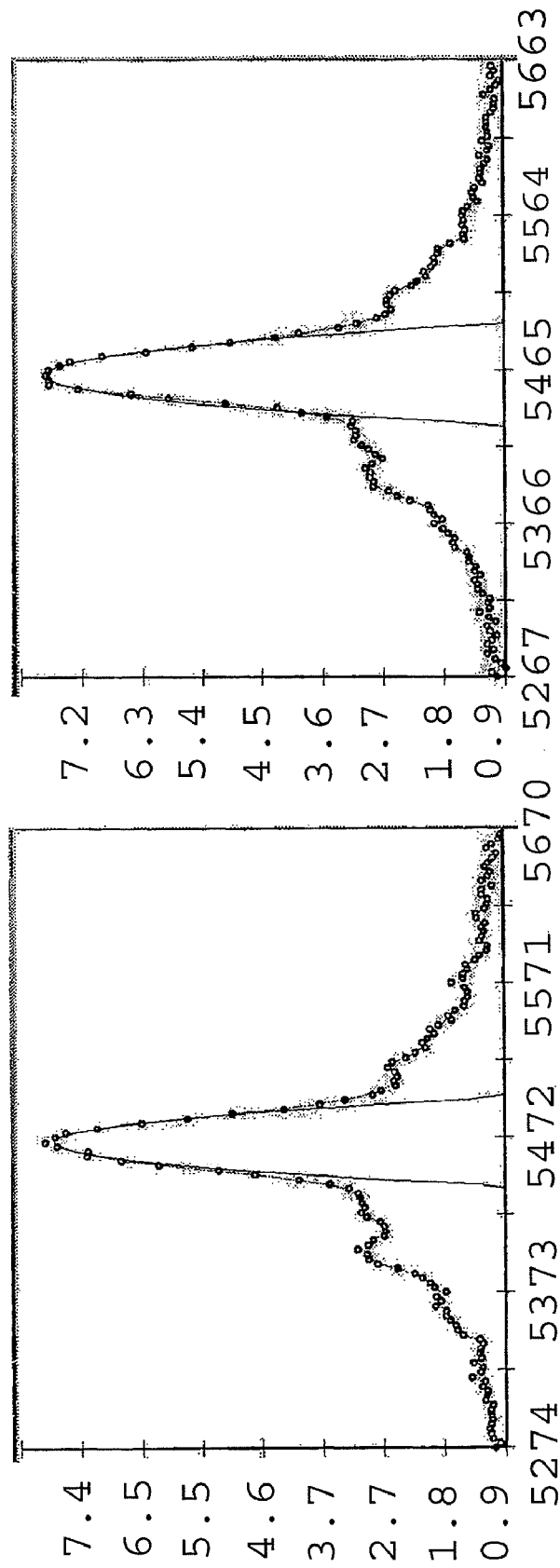
FIG. 29 shows simplified curves for focus score as a function of z position according to another embodiment of the present invention.

The disadvantage for obtaining focusing scores without image blurring can be improved by blurring the image and calculating ratios as discussed above. FIG. 29 shows simplified curves for focus score as a function of z position obtained at the process 4804 according to another embodiment of the present invention. This diagram is merely an example, which should not unduly limit the scope of the claims. One of ordinary skill in the art would recognize many variations, alternatives, and modifications. The focus score at each z value is associated with a ratio that is taken between the sobel square sum for the acquired image and the clipped sobel square sum for the blurred image. FIG. 28 and FIG. 29 are produced from the same acquired images.

As shown in FIG. 29, the blurring and ratio technique in effect normalizes the sobel output by the amount of that same output on a blurry version of the original. The peak of the curves in FIG. 29 occurs for the image which suffers the largest degradation as a result of the blurring operation. An image which suffers no degradation produces a ratio value of 1.0. This normalization process can remove the dependency of the sobel operation on the intensity of a particular image plane, which can fluctuate due to optical variations.

In certain embodiments, the number and scope of adjustments performed at the process 4420 for alignment and focusing depend on the accuracy of the mapping from the design space to the measurement space at the process 4410. For example, bending or tilting of the microfluidic device, thereby shifting the metering cell out of the original plane of the microfluidic device, may result in additional z-axis focusing actions. These additional focusing steps may result in an increase in the amount of time desired to acquire a high-resolution image of the metering cell. Improved mapping between the design space and measurement space would enable the imaging system to move the metering cells to position in which the acquisition of high-resolution images can be performed with increased efficiency.

Figure 30:
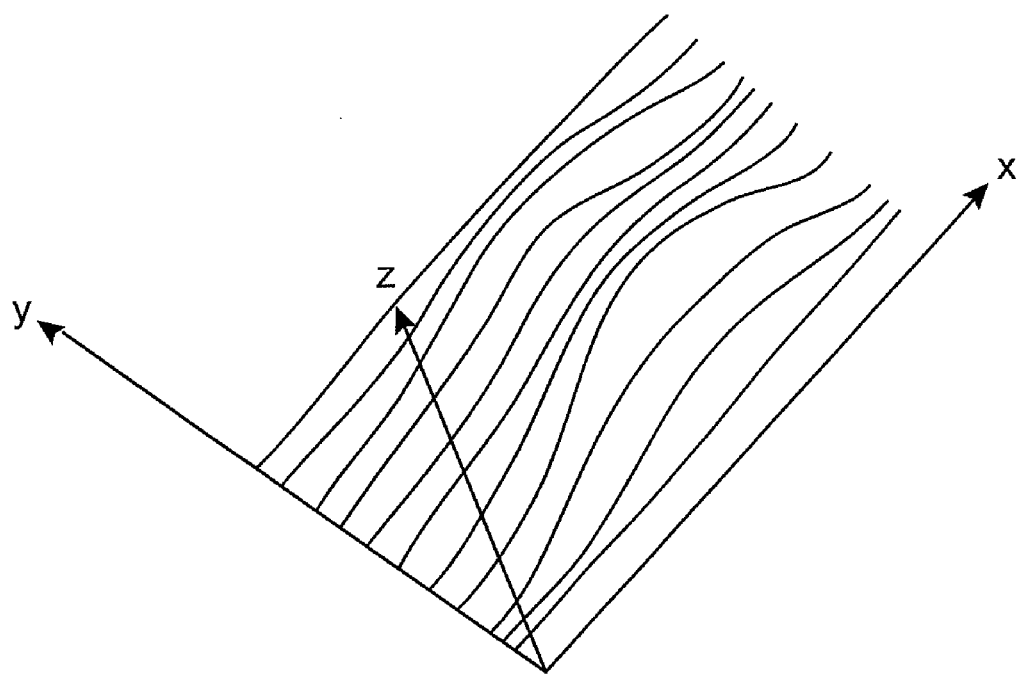
FIG. 30 is a simplified surface map of a three dimensional flexible substrate according to an embodiment of the present invention.

To further improve the mapping accuracy, in some embodiments, more than three fiducial markings may be used at the process 4410 to provide a non-planar transformation between the design space and the measurement space. FIG. 30 is a simplified surface map of a three dimensional flexible substrate according to an embodiment of the present invention. The warping or deformation of the microfluidic device is illustrated as an increase in z-axis height at certain x-y positions across the flexible substrate. In one embodiment, the inputs for this higher order dimensional mapping could come from location information obtained using more than three fiducial markings. In another embodiment, inputs could be provided based on measurements made on the metering cell at the process 4420. Feedback from these measurements can be used to update and refine the mapping as a function of time. Consequently, for another metering cell, placement of the microfluidic device in preparation for the process 4420 would improve in accuracy as more data is obtained. The generation of such a higher order dimensional mapping can substantially increase the system throughput by reducing or even eliminating the need for the process 4420 for some or all metering cells.

In one embodiment of the present invention, a 12 point microfluidic device registration process can be used that fits at least four fiducial markings with a non-planar surface. For example, a three dimensional parabola could be used as the mapping surface. For example, the process of determining the coarse and fine locations of each fiducial marking can contribute information used in calculation of the parabolic fitting parameters. In one embodiment, fiducials near the edges, the center, and other locations on the microfluidic device could be utilized, in various orders, in the calculation of the parabolic fitting parameters. In another embodiment, the processes 4410 and 4420 could be combined into a single predictive focus-based algorithm that uses higher order fitting and localized corrections to improve system throughput.

As discussed above, the method 4400 uses the processes 4410 and 4420 for alignment and focusing in certain embodiments. For example, at the process 4410, the alignment and focus of the fiducial marking associated with the metering cell are each within 100-µm accuracy. In another example, at the process 4420, the alignment of the fiducial marking is within about 1-µm accuracy. In yet another example, at the process 4420, the focusing of the fiducial marking is within about 1-µm accuracy.

As shown in FIG. 18, at the process 4430, the metering cell is moved to the focus position and an image of the metering cell is captured. For example, the captured image has a high resolution. In one embodiment, the image is acquired by the same camera that is used to capture the low-resolution image at the process 4810. In another embodiment, a Leica DC500 digital camera can be used to capture a high-resolution image. For example, the high resolution image has about 3900×3030 pixels and covers at least one well region including the fluid and species at a color depth of 16 bits. In another example, the image includes the containment lines, the wells, and the channels that connect the wells. In yet another example, the metering cell is moved in the x dimension and/or the y dimension in order to improve alignment prior to capturing the image of the metering cell.

The captured image is then normalized. In one embodiment, the color and intensity of the acquired image is significantly affected by the condition and operating voltage of the illumination source of the imaging system. For example, the illumination source is a bulb. As a bulb ages, the overall hue of the image changes, with the red component of the light increasing in intensity in comparison with the other colors. This increase in red intensity may result from a decrease in the bulb temperature. Additionally, even with a constant illumination source, the opacity of the microfluidic device, which can depend on hydration levels and vary with time, may result in differences in image brightness. To correct for these artifacts and any radial vignetting introduced by the microscope, a technique called image normalization can be employed.

For image normalization, a calibration image is taken with the microfluidic device removed from the imaging system with the stage at a z calibration position. In one example, the z calibration position is different from the focus position. The z calibration position may take into account changes to the illumination beam as the beam passes through the microfluidic device. In anther example, the z calibration position is the same as the focus position. The calibration image is then used to correct for the effects resulting from the condition and operating voltage of the illumination source. In one embodiment, the algorithm calculates the ratio of the intensity of the acquired image of the metering cell to the calibration image on a pixel by pixel basis. The microfluidic device includes regions that contain substantially no information, the ratio of the intensities in these regions is set equal to unity. The intensity ratio is then multiplied by a scaling factor to maximize the dynamic range around unity.

Although the mapping from this calibration image to the actual image may not be linear due to the bending of light rays as they pass through the microfluidic device and/or glass slab, the image normalization effectively white balances the image by adjusting the red, blue, and green components of the image. Additionally, the image normalization improves consistency between the attenuated edge pixels and the center pixels. For example, the effects of white balance and consistency improvement are significant for low illumination conditions and particular condenser and/or aperture settings in which the non-linearity is pronounced.

Moreover, the image is median shifted to move the centroid of the image histogram, i.e., counts as a function of intensity, to a known value. The image is also downgraded around that centroid to reduce the data size in the image. For example, the intensity ratio is sampled at random locations on the microfluidic device. Using these sampled intensity ratio values, the image is adjusted to shift the centroid of the image to the known value. In one embodiment, the centroid is shifted to align with an intensity level of 128, and the image is downgraded to 8 bits. This shift may be used to either darken or brighten the image. In one embodiment, the normalized, white balanced, and downgraded image is stored in a computer memory available for further processing.

As discussed above and further emphasized here, the above description of the process 4430 includes merely examples, which should not unduly limit the scope of the claims. One of ordinary skill in the art would recognize many variations, alternatives, and modifications. Although the above has been shown using a selected sequence of processes, there can be many alternatives, modifications, and variations. For example, some of the processes may be expanded and/or combined. Other processes may be inserted to those noted above. Depending upon the embodiment, the specific sequences of processes may be interchanged with others replaced. Further details of these processes are found throughout the present specification.

For example, in another embodiment of the present invention, information obtained at the process 4430 could be used as data inputs for the parabolic fitting at the process 4410 for another metering cell. In this embodiment, the three dimensional locations of the metering cell, as determined from the high-resolution image, can provide information useful in determining the parabolic fitting parameters. For example, the metering cells near the center of the microfluidic device, separated from the fiducial markings near the edges of the microfluidic device, may be measured earlier in time than metering cells near the fiducial markings. The early measurements of centrally located metering cells may provide for faster convergence of the fitting algorithm as the measured location of these centrally located cells may differ from the planar mapping more than the measured locations of cells closer to the fiducial markings.

As discussed above, the method 4400 uses various fiducial markings in various processes. In one embodiment, the fiducial markings can be any physical features associated with the microfluidic device. For example, the fiducial markings are on the handle substrate of the microfluidic device. In another example, the fiducial markings are on the flexible substrate of the microfluidic device. The fiducial markings may include a channel wall or an edge of the microfluidic device. In yet another example, the fiducials markings are selected from ones described in FIGS. 1-13A and 15A-15B.

Additionally, the method 4400 align and focus a metering cell and acquire an image of the metering cell. The alignment and focus process may use at least one fiducial marking for the process 4420. The spatial relationship between the fiducial marking and the metering cell does not change significantly. For example, the fiducial marking is in the vicinity of the metering cell. The metering cell is merely an example, which should not unduly limit the scope of the claims. One of ordinary skill in the art would recognize many variations, alternatives, and modifications. In one embodiment, the method 4400 is applied to any physical feature on the microfluidic device. The physical feature is aligned and focused, and an image of the physical feature is taken. For example, the physical feature is a chamber. The chamber may be a well, a fluid channel, a control channel, or else.

Moreover, the method 4400 may be performed by the imaging system 4010 or another imaging system according to the instructions of the computer system 4110 or another computer system. For example, a system for processing one or more microfluidic devices includes one or more computer-readable media and a stage for locating a flexible substrate. The flexible substrate comprises at least three fiducial markings, a first additional fiducial marking, and a first chamber capable of holding a fluid therein. For example, a volume of the fluid is less than a nanoliter. The one or more computer-readable media include one or more instructions for providing a flexible substrate, and one or more instructions for determining a transformation between a design space and a measurement space based on at least information associated with the at least three fiducial markings. Additionally, the one or more computer-readable media include one or more instructions for performing a first alignment to the flexible substrate based on at least information associated with the transformation between the design space and the measurement space, one or more instructions for acquiring at least a first image of the first additional fiducial marking associated with the first chamber, one or more instructions for performing a second alignment to the flexible substrate based on at least information associated with the first image, and one or more instructions for acquiring a second image of the first chamber associated with the flexible substrate.

The one or more instructions for determining a transformation between a design space and a measurement space include one or more instructions for determining at least three actual locations corresponding to the at least three fiducial markings respectively. The at least three fiducial markings are associated with at least three design locations respectively. Additionally, the one or more instructions for determining a transformation include one or more instructions for processing information associated with the at least three actual locations and the at least three design locations. The design space is associated with the at least three design locations and the measurement space is associated with the at least three actual locations. The one or more instructions for acquiring at least a first image of the first additional fiducial marking include one or more instructions for acquiring a first plurality of images of the first additional fiducial marking. The first plurality of images includes the first image. Additionally, the one or more instructions for acquiring at least a first image includes one or more instructions for processing information associated with the first plurality of images.

Moreover, the one or more computer-readable media includes one or more instructions for storing the second image in a memory. The memory is a computer memory. The second image includes 3900 by 3030 pixels. The second image comprises a 16 bit image. The one or more instructions for performing a second alignment to the flexible substrate includes one or more instructions for translating the flexible substrate in at least one dimension to position a chamber in preparation for capturing the second image. Also, the one or more computer-readable media includes one or more instructions for normalizing the second image, one or more instructions for white balancing the second image, and one or more instructions for converting the second image from a first image depth to a second image depth. For example, the first image depth is 16 bits and the second image depth is 8 bits.

In one embodiment, the first additional fiducial marking is a company logo. The at least three fiducial markings include a company logo. In another embodiment, the flexible substrate is deformable in three dimensions. For example, the flexible substrate is deformed by actions selected from the group consisting of fabrication, handling, and protocols. The protocols can result in the flexible substrate swelling or contracting. In yet another embodiment, a relationship between the design space and the measurement space is non-planar. The flexible substrate is deformed such that a planar transformation is capable to approximately determine an actual location of the first chamber. In yet another embodiment, the transformation between the design space and the measurement space is non-planar. For example, the non-planar transformation comprises a three dimensional parabolic mapping. The non-planar transformation is updated using information obtained by characterization of a second additional fiducial marking.

Numerous benefits are achieved using the present invention over conventional techniques. Some embodiments provide at least one way to form alignment patterns for a deformable active region for a microfluidic system. Certain embodiments rely on conventional materials, which are relatively easy to use. Some embodiments provide alignment and/or focus based on mapping between the design space and the measurement space. The transformation between the design space and the measurement space uses, for example, at least three fiducial markings. Certain embodiments provide accurate focusing by acquiring and analyzing a plurality of images along at least one dimension. Some embodiments of the present invention perform alignment and focusing on a microfluidic device including at least one flexible substrate. The alignment and focusing take into account the deformation of the flexible substrate. Certain embodiments improve throughput in imaging system. For example, the imaging system uses a computer system to automatically perform alignment and focusing. In another example, mapping from the design space to the measurement space increases the accuracy of stage positioning, and thereby, the efficiency of high-resolution image acquisition. Depending upon the embodiment, one or more of these benefits may exist. These and other benefits have been described throughout the present specification.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A microfluidic system, the system comprising:
   a rigid substrate material, the rigid substrate material having a surface region, the surface region being capable of acting as a handle substrate;
   a deformable fluid layer coupled to the surface region;
   one or more well regions formed in a first portion of the deformable fluid layer, the one or more well regions being capable of holding a fluid therein;
   one or more channel regions formed in a second portion of the deformable fluid layer, the one or more channel regions being coupled to one or more of the well regions;
   an active region formed in the deformable fluid layer, the active region including the one or more well regions;
   a non-active region formed in the deformable fluid layer, the non-active region being formed outside of the first portion and the second portion;
   a first fiducial marking formed within the non-active region and disposed in a spatial manner associated with at least one of the channel regions;
   a second fiducial marking formed within the non-active region and disposed in a spatial manner associated with at least one of the well regions;
   a control layer coupled to the fluid layer, the control layer including one or more control regions; and
   a third fiducial marking formed within the control layer.

2. The substrate of claim 1 wherein the second fiducial marking is a company logo and is larger than either the first fiducial marking or the second fiducial marking.

3. The substrate of claim 1 wherein the first fiducial marking comprises a first channel fiducial marking and a second channel fiducial marking, the first channel fiducial marking being spatially disposed from the second channel fiducial marking.

4. The substrate of claim 1 wherein the third fiducial marking comprises a first control fiducial marking and a second control fiducial marking, the first control fiducial marking being spatially disposed from the second control fiducial marking.

5. The substrate of claim 1 wherein the first fiducial marking, the second fiducial marking, and the third fiducial marking, being spatially disposed from each other along the surface region.

6. The substrate of claim 1 wherein the first fiducial marking is characterized by a spatial dimension of greater than 100 µm and less than 250 µm.

7. The substrate of claim 1 wherein the first fiducial marking is characterized by a depth of at least 10 µm within a thickness of the non-active region.

8. The substrate of claim 1 wherein the second fiducial marking is characterized by a depth of at least 10 µm within a thickness of the non-active region.

9. The substrate of claim 1 wherein the third fiducial marking is characterized by a depth of at least 10 µm within a thickness of the control layer.

10. A microfluidic system, the system comprising:
    a substrate comprising a surface region;
    a deformable layer coupled to the surface of the substrate, the deformable layer being made of at least a thickness of first material;
    a control layer coupled to the deformable layer to form a sandwich structure including at least the substrate, the deformable layer and the control layer, the control layer being made of at least a thickness of second material;
    at least one fiducial marking provided within either the control layer or the deformable layer or the substrate, the fiducial marking being characterized by a visual pattern provided in a volume surrounded wholly or partially by at least the substrate, the first material, or the second material; and
    a fluid disposed within the open volume of the one fiducial marking, the fluid being characterized by a refractive index.

11. The system of claim 10 wherein the refractive index is associated with air.

12. The system of claim 10 wherein the fluid comprises an air mixture.

13. The system of claim 10 wherein the fluid comprises air.

14. The system of claim 10 wherein the open volume is characterized by a recessed region.

15. The system of claim 10 wherein the refractive index is substantially different from a surrounding material, the surrounding material being either the first material or the second material or the substrate.

16. The system of claim 10 wherein the fiducial marking is characterized by edges to form the pattern.

17. The system of claim 16 wherein the edges comprises 90 degree corners.

18. The system of claim 10 wherein the fluid is non-reactive.

19. The system of claim 10 wherein the substrate is selected from silicon, quartz, glass, or rigid plastic.

* * * * *